United States Patent
Mazourik et al.

(10) Patent No.: US 10,993,842 B2
(45) Date of Patent: May 4, 2021

(54) FUNCTIONAL SOCK

(71) Applicant: Sergei Mazourik, Delémont (CH)

(72) Inventors: Sergei Mazourik, Delémont (CH);
Oksana Mazourik, Delémont (CH);
Katharina Mazourik, Delémont (CH);
Michael Mazourik, Delémont (CH)

(73) Assignee: Sergei Mazourik, Delemont (CH)

( * ) Notice: Subject to any disclaimer, the term of this patent is extended or adjusted under 35 U.S.C. 154(b) by 762 days.

(21) Appl. No.: 15/179,598

(22) Filed: Jun. 10, 2016

(65) Prior Publication Data

US 2017/0354543 A1    Dec. 14, 2017

(51) Int. Cl.
*A61F 13/08*    (2006.01)
*A61H 1/00*    (2006.01)

(52) U.S. Cl.
CPC .............. *A61F 13/08* (2013.01); *A61H 1/008* (2013.01); *A41D 2400/32* (2013.01);
(Continued)

(58) Field of Classification Search
CPC ........ A61F 13/08; A61F 13/085; A61F 13/06; A61F 13/061; A61F 13/062; A61F 13/064; A61F 5/0106; A61F 5/0109; A61F 5/0123; A61F 5/0127; A41D 1/08; A41D 13/0015; A41D 1/082; A41D 1/084; A41D 1/085;
(Continued)

(56) References Cited

U.S. PATENT DOCUMENTS 2,574,873 A * 11/1951 Jobst ...................... A61F 13/08
602/63
3,832,780 A    9/1974 Lewis
(Continued)

FOREIGN PATENT DOCUMENTS

CN    202060979 U    12/2011
CN    204951340 U    1/2016
(Continued)

OTHER PUBLICATIONS

"CompreFIT by BiaCare." <http://biacare.com/product/comprefit-knee/>. Accessed May 26, 2016.
(Continued)

*Primary Examiner* — Rachael E Bredefeld
*Assistant Examiner* — Rachel A Berezik
(74) *Attorney, Agent, or Firm* — Bryant J. Keller; Kirton McConkie

(57) ABSTRACT

Clothing and methods for providing targeted and staged compression to portions of a lower extremity, such as a leg of a human may include individual pieces of clothing such as socks and the like, or multiple-piece clothing systems functioning together to provide targeted and staged compression to the lower extremity. One or more articles of clothing individually or together have a plurality of targeted compression zones. Each of the compression zones includes a superior portion extending in a generally superior-inferior direction and an inferior portion contiguous with the superior portion and comprising a portion extending in a direction generally crosswise to the generally superior-inferior direction of the superior portion. Other implementations are also described.

20 Claims, 44 Drawing Sheets

(52) U.S. Cl.
CPC .... *A61H 2205/10* (2013.01); *A61H 2205/106* (2013.01); *A61H 2205/108* (2013.01)

(58) Field of Classification Search
CPC .......... A41D 1/086; A41D 1/089; A41D 1/22; A41D 13/0017; A41D 13/0156; A41D 13/0543; A41D 13/06; A41D 13/065; A41D 13/1254; A41D 2400/32; A41D 2400/322; A41D 2400/38; A41D 2400/80; A41D 2400/82; A41D 2600/10; A41D 2600/102; A41D 2600/104; A41D 2600/106; A41D 2600/108; A41D 2600/20; A41B 11/00; A41B 11/003; A41B 9/08; A41B 9/12; A41B 11/008; A41B 11/02; A41B 11/04; A41B 11/12; A41B 11/14; A41B 11/143; A41B 11/146; A61H 1/008; A61H 2205/10; A61H 2205/106; A61H 2205/108; A61H 2205/102; A61H 2205/104; A61H 2207/00; A61H 2209/00
USPC .................. 602/75, 23, 26; 2/239, 241, 242
See application file for complete search history.

(56) References Cited

U.S. PATENT DOCUMENTS

| | | | |
|---|---|---|---|
| 4,172,456 A | 10/1979 | Zens | |
| 5,898,948 A | 5/1999 | Kelly et al. | |
| 6,012,177 A | 1/2000 | Cortinovis | |
| 6,123,681 A | 9/2000 | Brown, III | |
| 6,311,334 B1 | 11/2001 | Reinhardt et al. | |
| 6,430,752 B1 * | 8/2002 | Bay | A41C 1/003 2/228 |
| 6,589,194 B1 | 7/2003 | Calderon et al. | |
| 6,684,412 B2 | 2/2004 | Ricci et al. | |
| 7,192,411 B2 | 3/2007 | Gobet et al. | |
| 7,942,838 B2 | 5/2011 | Farrow | |
| 8,221,340 B2 | 7/2012 | Farrow et al. | |
| 2004/0249329 A1 * | 12/2004 | Hess | A61F 5/0109 602/63 |
| 2007/0033711 A1 | 2/2007 | Achtelstetter | |
| 2008/0249454 A1 | 10/2008 | Mills | |
| 2009/0113596 A1 * | 5/2009 | Young | A41D 13/0015 2/69 |
| 2010/0137776 A1 * | 6/2010 | Virkus | A61F 13/08 602/62 |
| 2011/0131706 A1 | 6/2011 | Andersson | |
| 2013/0172926 A1 | 7/2013 | Barker | |
| 2014/0082815 A1 * | 3/2014 | Harber | A41B 11/003 2/69 |
| 2016/0338424 A1 * | 11/2016 | Kehler | A41B 11/08 |
| 2017/0013886 A1 * | 1/2017 | Towfigh | A41C 1/10 |

FOREIGN PATENT DOCUMENTS

| | | | | |
|---|---|---|---|---|
| EP | 1 086 675 A2 | 3/2001 | | |
| FR | 688378 A | * | 8/1930 | ............. A61F 13/08 |

OTHER PUBLICATIONS

"Amazon.com SAGUARO Elastic Ankle Foot Compression Wrap Strap Support Bandage Brace Protective Gear Guard for Outdoor Sports Gym Volleyball Basketball." <http://www.amazon.com/SAGUARO-Compression-Protective-Volleyball-Basketball/dp/B00UCP0AYY?>. Accessed May 26, 2016.

* cited by examiner

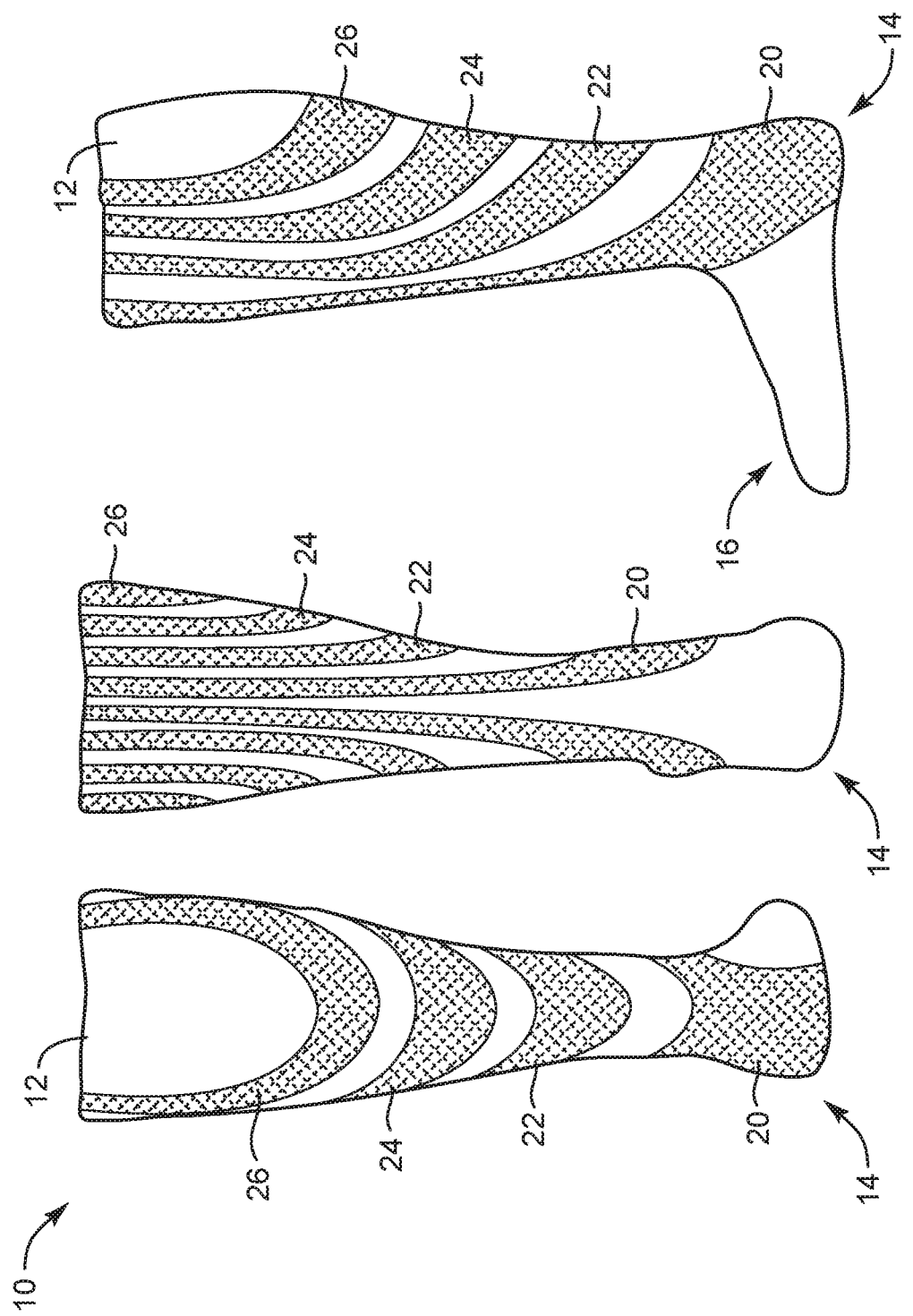

20° Arch

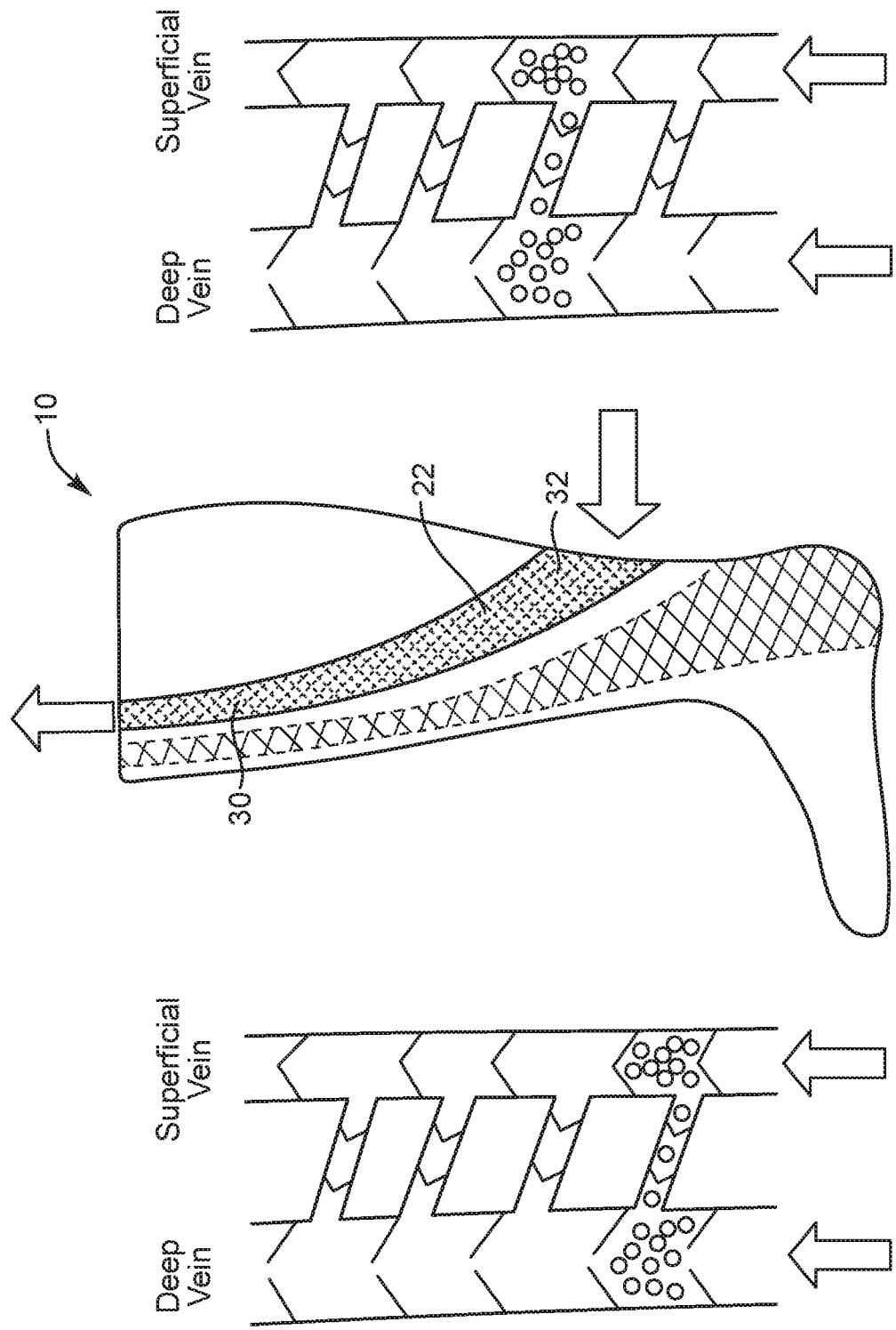

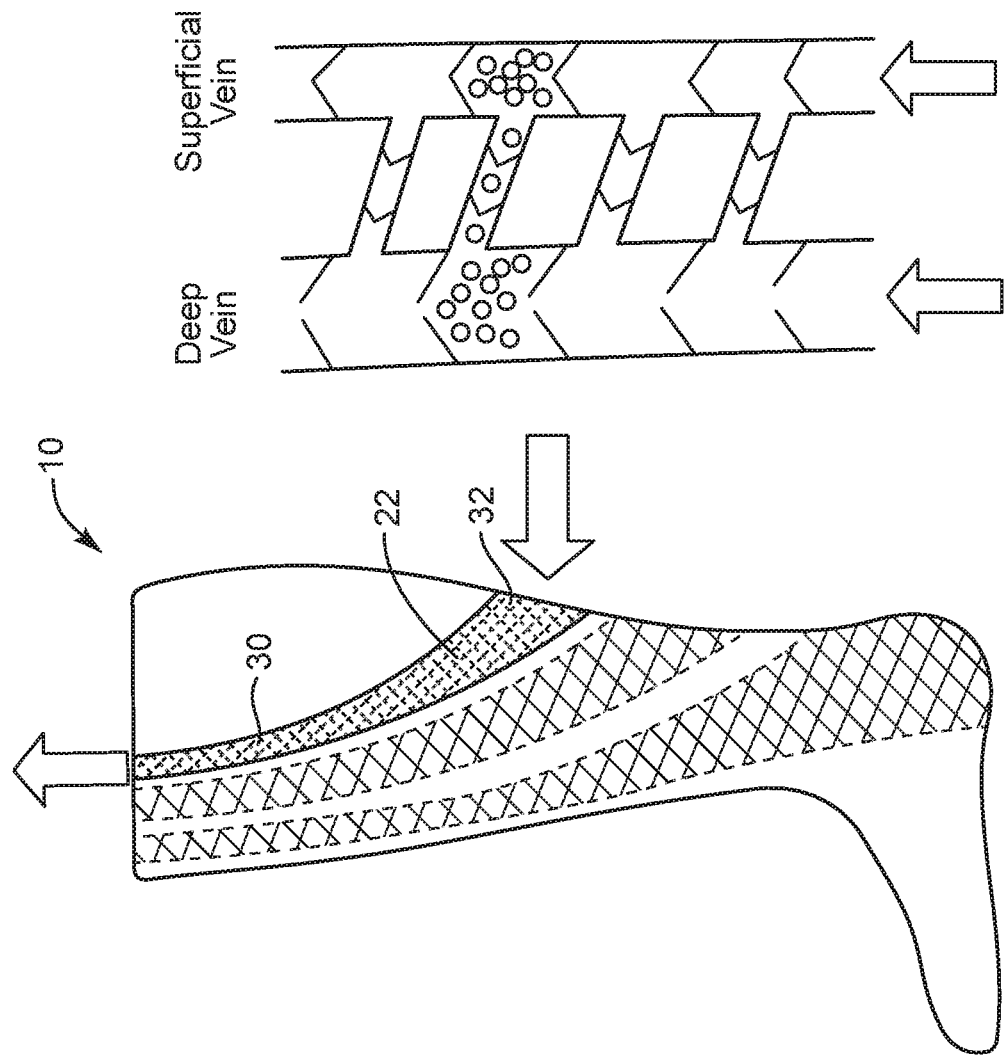
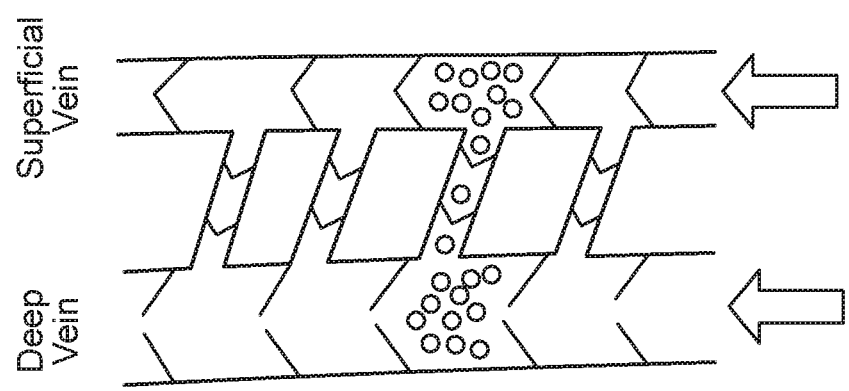
FIG. 11C
FIG. 11B
FIG. 11A

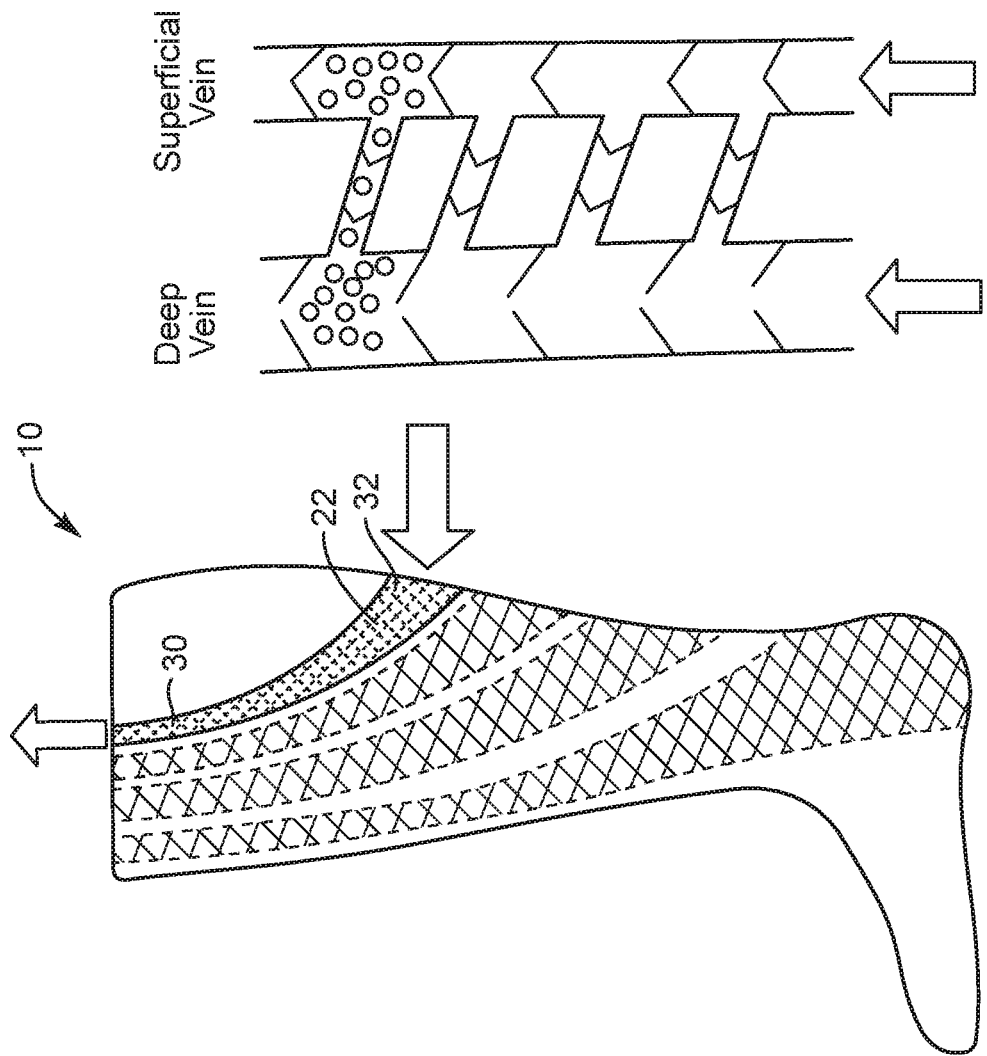
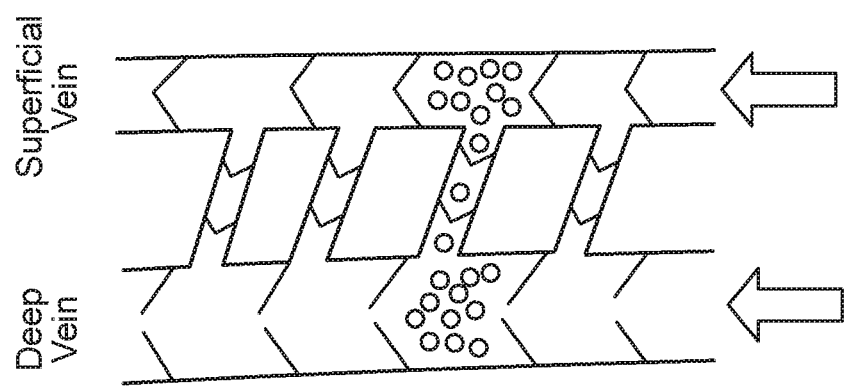
FIG. 12C
FIG. 12B
FIG. 12A

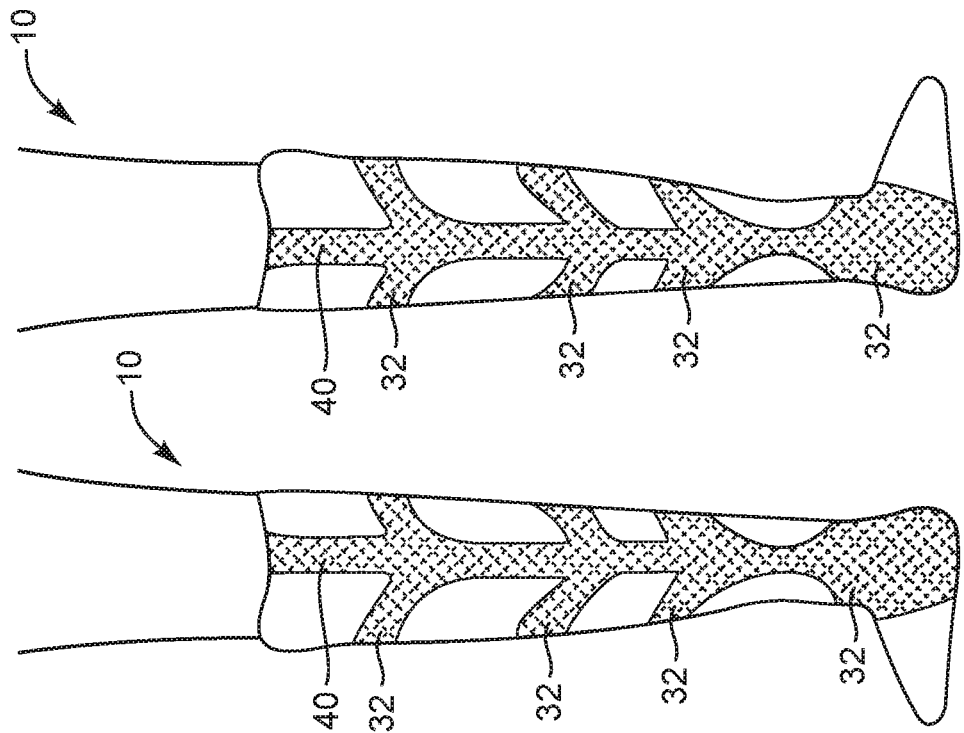
FIG. 13C
FIG. 13B
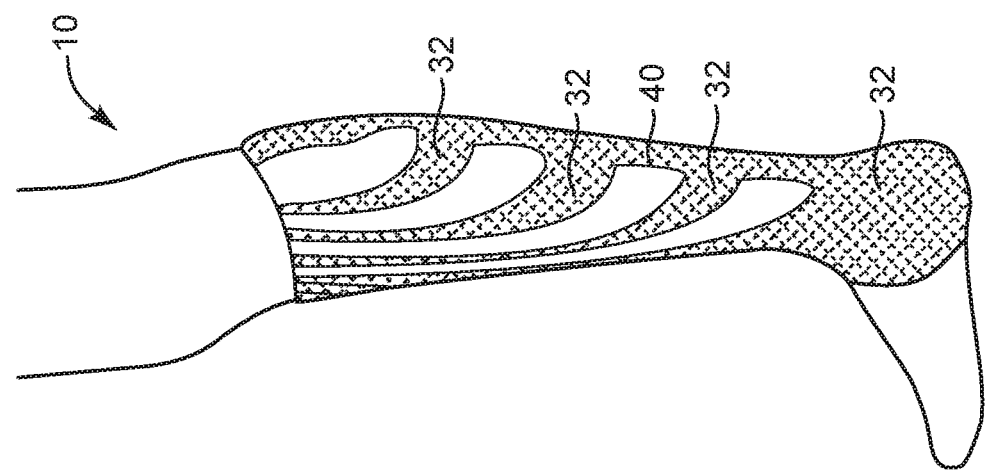
FIG. 13A

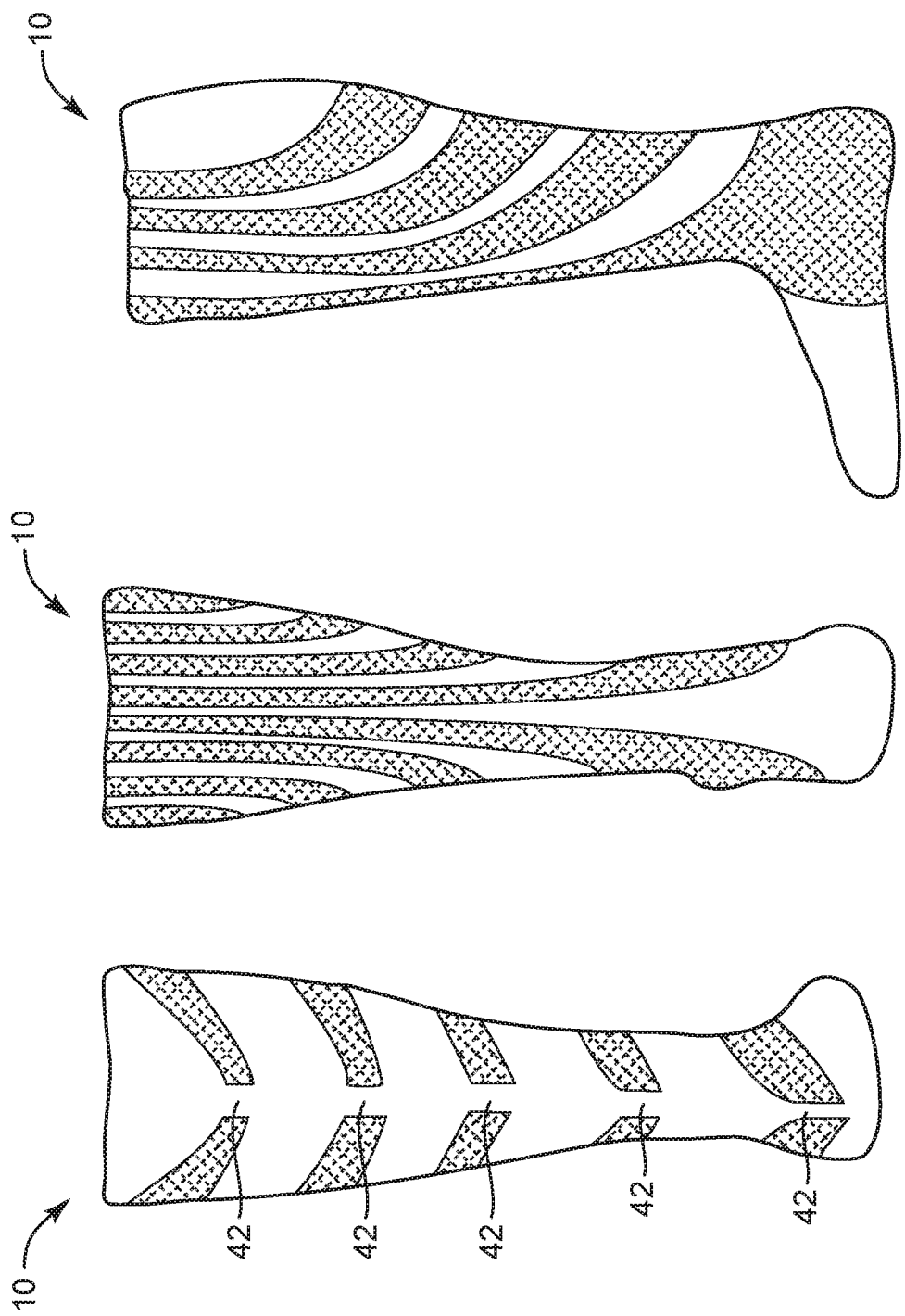

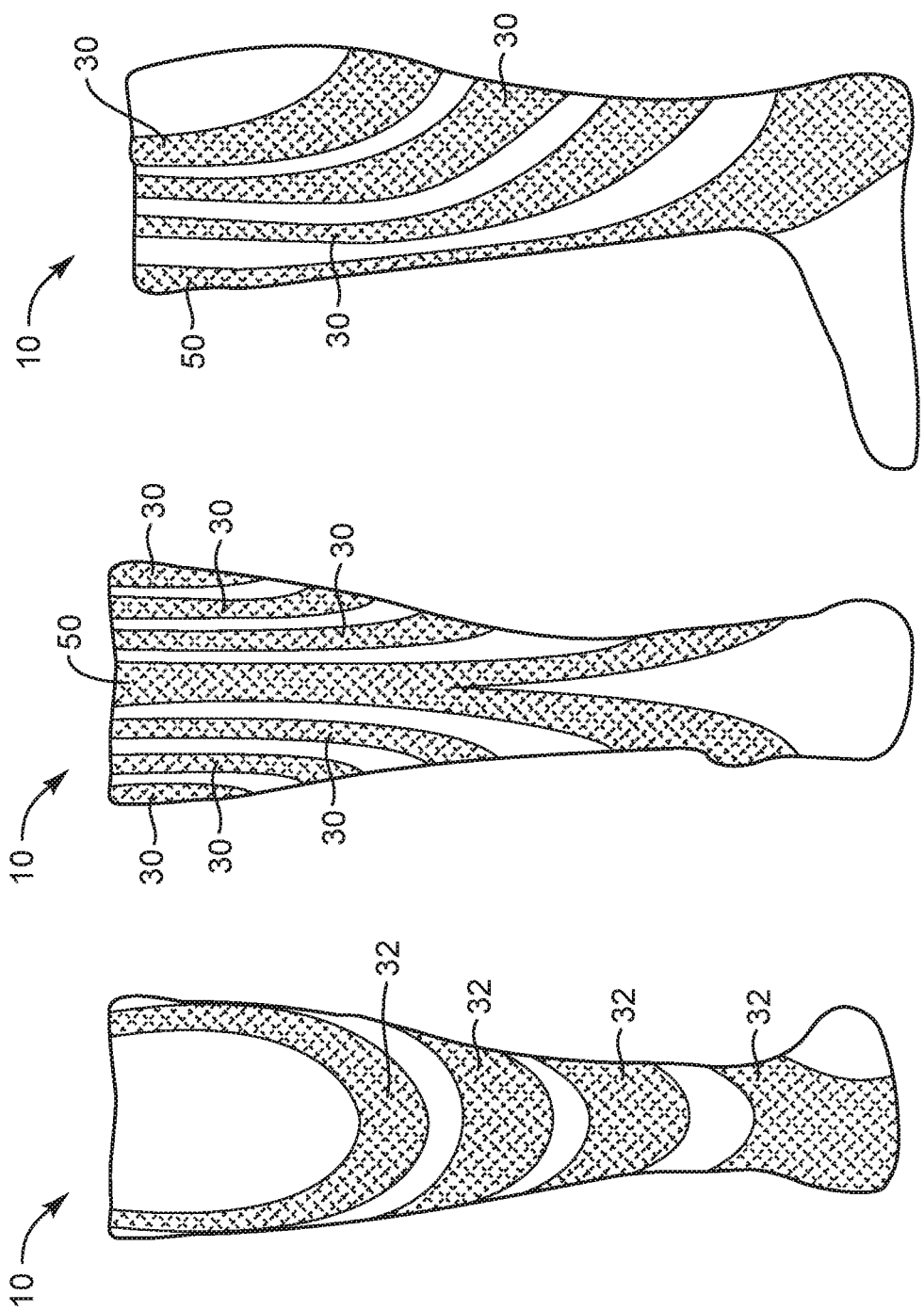

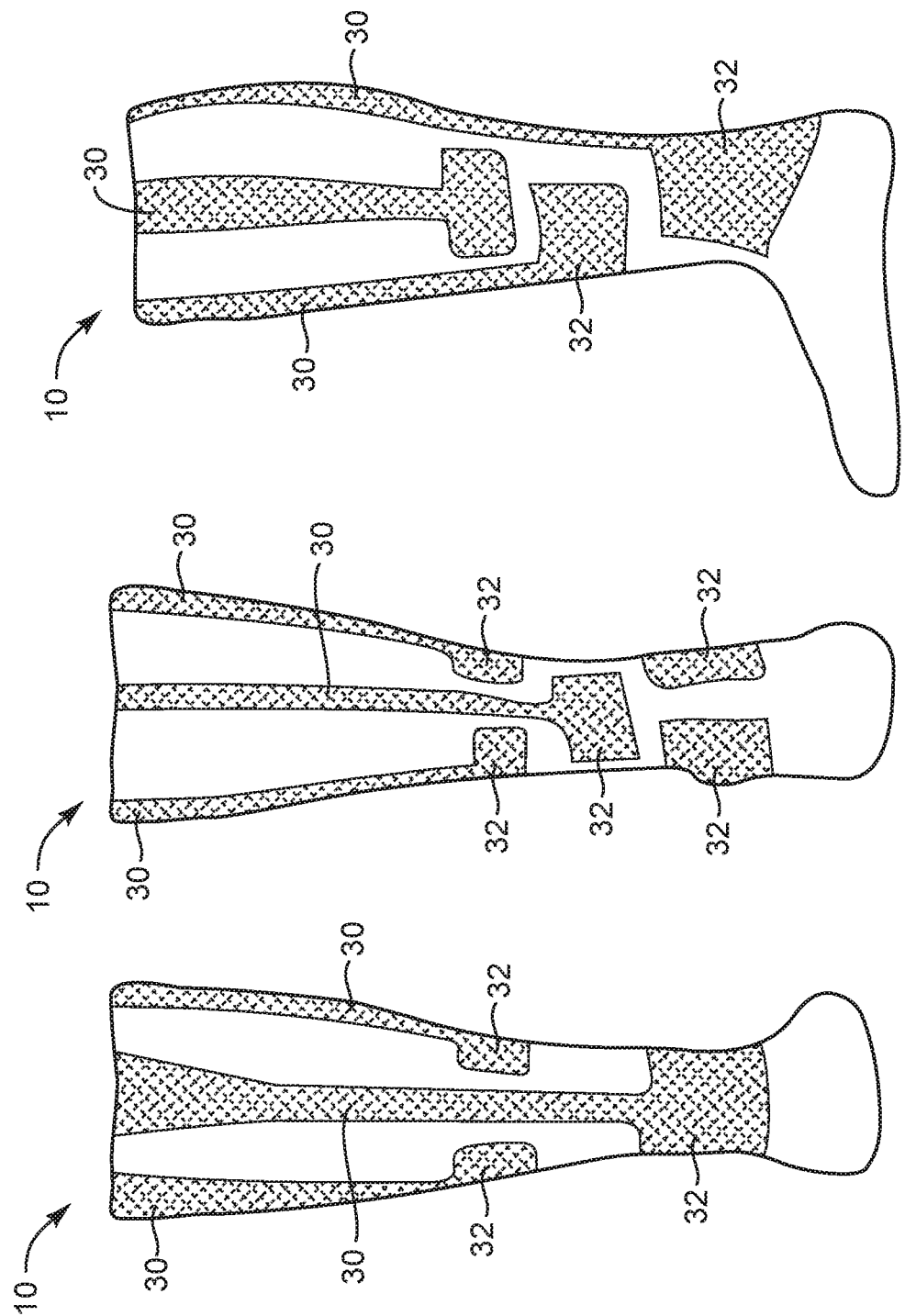

Too much compression from ordinary compression socks can cause the superficial veins to be over compressed & restrict blood flow.

"Ordinary" Compression Socks

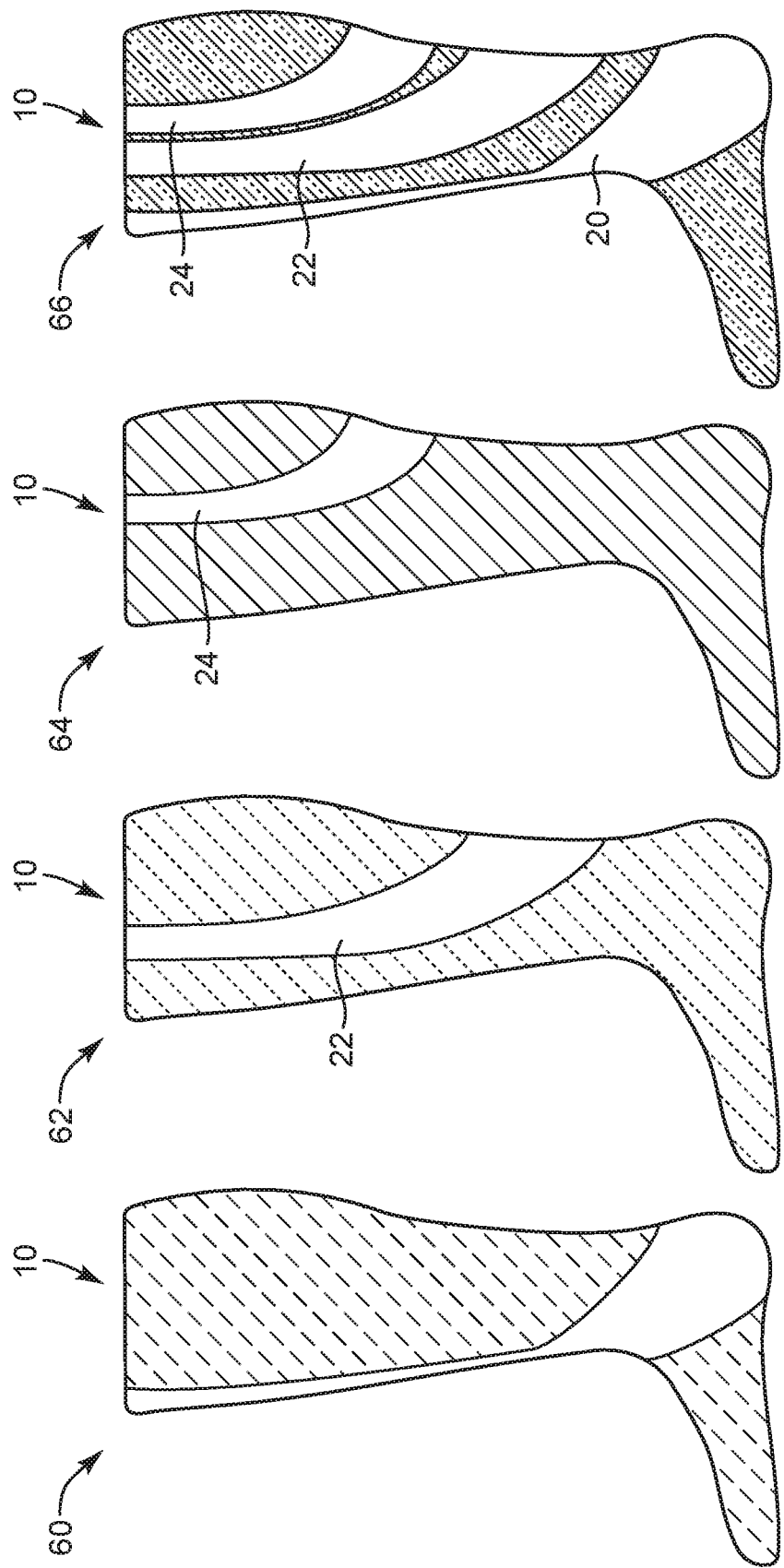

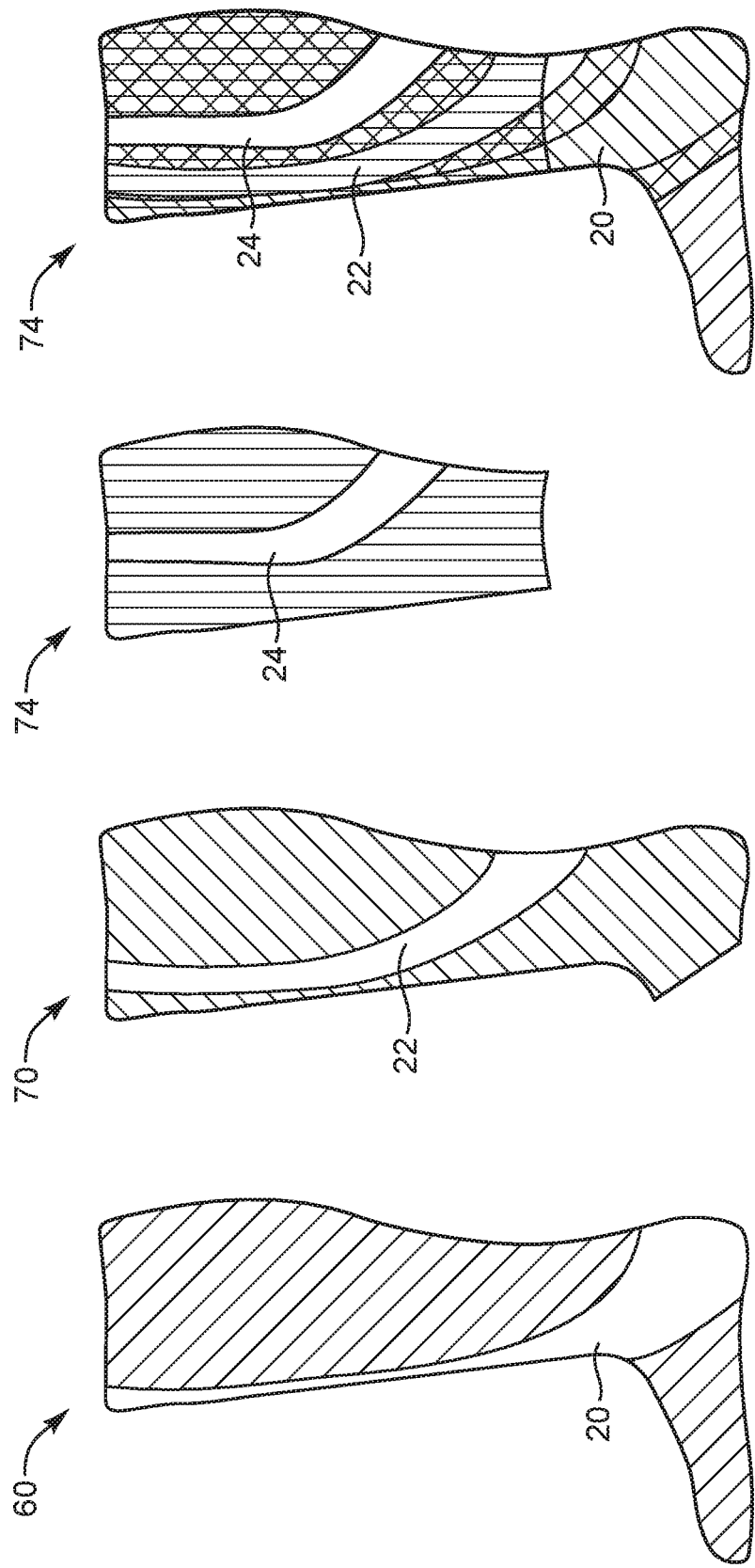

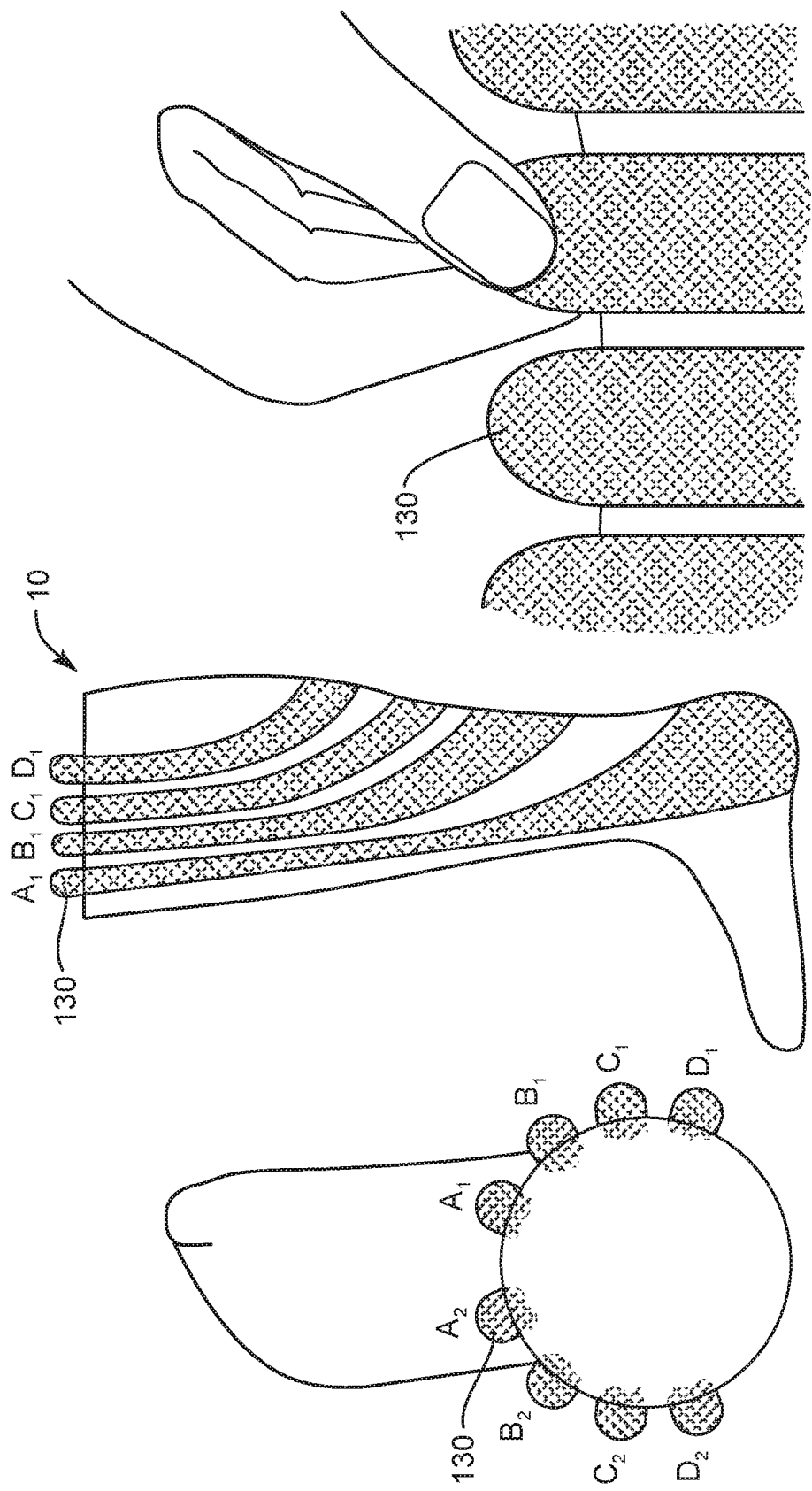

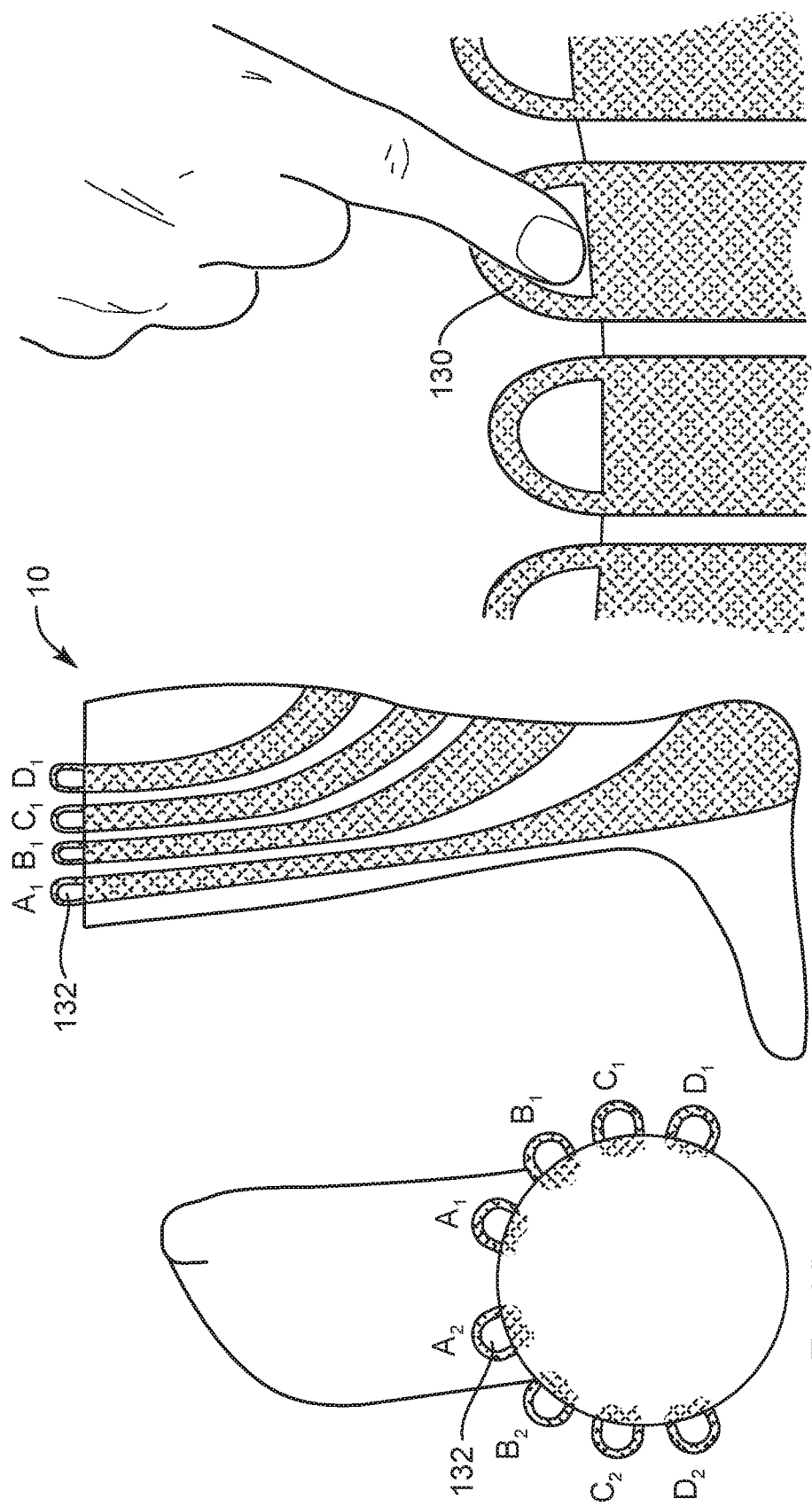

FUNCTIONAL SOCK

BACKGROUND OF THE INVENTION

1. Field of the Invention

The present invention relates to clothing, and more particularly to a functional sock with compression zones that provide or assist in removal of excess venous blood in the foot and calf.

2. Background and Related Art

Compression stockings are a type of hosiery designed to help prevent the occurrence of, and to guard against further progression of, venous disorders such as edema, phlebitis, and thrombosis. The compression stockings are elastic garments that extend around the leg, compressing the limb. In some cases, the compression reduces the diameter of distended veins in the leg, leading to increased venous blood flow velocity and valve effectiveness. Compression therapy can help decrease venous pressure, prevent venous stasis and impairments of venous walls, and relieve heavy and aching legs.

Knee-high compression stockings are often used to increase circulation and also to help prevent the formation of blood clots in the lower legs. They may also assist in the treatment of ulcers of the lower legs.

Generally, compression stockings use stronger elastics than are used in traditional socks or stockings to create significant pressure on the legs, ankles, and/or feet. Some compression stockings have graduated compression, with greater compression at the feet/ankles and becoming gradually less constrictive toward the knees.

BRIEF SUMMARY OF THE INVENTION

Some implementations of the invention provide clothing, including clothing systems, and methods for providing targeted and staged compression to portions of a lower extremity, such as a leg of a human. The clothing or clothing system may include individual pieces of clothing such as socks and the like, or multiple-piece clothing systems that function together to provide targeted and staged compression to the lower extremity.

According to certain implementations, a system providing targeted compression to portions of a lower extremity to provide improved venous return characteristics includes one or more articles of clothing individually or together having a plurality of targeted compression zones. In some such implementations, each of the compression zones includes a superior (or proximal) portion extending in a generally superior-inferior (or proximal-distal) direction (or in other words, in a generally length-wise direction) and an inferior (or distal) portion contiguous with the superior portion and comprising a portion extending in a direction generally orthogonal to the generally superior-inferior direction of the superior portion (or, in other words, generally horizontally or in a generally crosswise direction).

In some implementations, the system includes a single article of clothing such as a sock, a legging, a calf sleeve, a sleeve, an arm sleeve, a torso sleeve, a glove, a portion of hosiery, a leg of a pair of pants, a stocking, a leg of a pair of tights, tights, a pair of sweat pants, a girdle, a foundation garment, a piece of shapewear, a piece of shaping underwear, a body suit, a unitard, a control slip, a band (e.g., a band for a leg, ankle, waist, arm, wrist, torso, etc.), and/or any other suitable article of clothing. In other implementations, the system includes a plurality of articles of clothing adapted to be at least partially layered over one another. In some such systems, the articles of clothing may each include at least one of a plurality of targeted compression zones. The articles of clothing may include one or more socks, one or more leggings, one or more calf sleeves, one or more sleeves, one or more arm sleeves, one or more bands (e.g., bands for a leg, ankle, waist, arm, wrist, torso, etc.), one or more torso sleeves, one or more gloves, one or more pieces of hosiery, a leg of one or more pairs of pants, one or more stockings, a leg of one or more pairs of tights, one or more tights, one or more one or more pairs of sweat pants, one or more girdles, one or more foundation garments, one or more pieces of shapewear, one or more pieces of shaping underwear, one or more body suits, one or more unitards, one or more control slips, and/or any other suitable articles (or combination of articles) of clothing. In some implementations, the clothing system may include one or more articles of clothing for one or more lower extremities, such as a sock for each foot/leg and/or a pair of pants having compression zones in each leg.

In certain implementations, one or more of the targeted compression zones include a pair of superior (or proximal) portions extending in the generally superior-inferior direction (or proximal-distal direction). Although each of the superior portions may be non-contiguous with a corresponding inferior portion, in some other embodiments, each of the superior portions is contiguous with opposite ends of the inferior (or distal) portion. In some instances, a targeted compression zone having a most-inferiorly located inferior portion has a most-anteriorly located superior portion. Each compression zone having a subsequently more-superiorly located inferior portion may have a subsequently more-posteriorly located superior portion.

In some implementations, the superior portions of the plurality of targeted compression zones terminate, at their superior ends, at between approximately zero and approximately sixty degrees (and any sub-range thereof) around either side of the article of clothing from a most-anterior portion of the article of clothing. In some such implementations, the superior portions of the plurality of targeted compression zones terminate, at their superior ends, at between approximately zero and approximately forty-five degrees (and any subrange) around either side of the article of clothing from a most-anterior portion of the article of clothing (or, in some implementations, a portion of the article of clothing that is configured to be located most anteriorly when worn on a user).

In certain implementations, a targeted compression zone having a most-inferiorly located inferior portion may be adapted to translate a substantially superiorly directed force applied to its superior portions into a compression exerted by its inferior portion at an angle (and/or at a curve such that a portion of the inferior portion of the compression zone runs at an angle) between approximately forty degrees and approximately fifty degrees. Any targeted compression zones having more-superiorly located inferior portions may be adapted to translate a substantially superiorly directed force applied to their superior portions into compression exerted by their inferior portions at an angle between approximately fifty-five degrees and approximately sixty-five degrees.

In certain of such implementations, a targeted compression zone having a most-inferiorly located inferior portion may be adapted to translate a substantially superiorly directed force applied to its superior portions into a compression exerted by its inferior portion at an angle of approximately forty-five degrees. Any targeted compression zones having more-superiorly located inferior portions may be adapted to translate a substantially superiorly directed force applied to their superior portions into compression exerted by their inferior portions at an angle of approximately sixty degrees±five degrees.

According to some implementations, the inferior portions of the plurality of targeted compression zones extend along a portion of a lower extremity, such as from a lower portion of a foot (e.g., a pad, a sole, a plantar portion, a sural portion, a saphenous portion, one or more toes, a heel, etc.) to an upper portion of the foot (e.g., a dorsum, a side, etc.), from an arch of a foot to an ankle area, from an arch of a foot to a calf area, from an arch of a foot to a thigh area, from a heel to an ankle area, from a heel to a lower calf area, from a heel to a mid-calf area, from a heel to an upper calf area, from a heel to a lower thigh area, from a heel to a mid-thigh area, from a heel to an upper thigh area, from a lower calf area to a mid-calf area, from a lower calf area to an upper calf area, from a lower calf area to a lower thigh area, from a lower calf area to a mid-thigh area, from a lower calf area to an upper thigh area, from a mid-calf area to an upper calf area, from a mid-calf area to a lower thigh area, from a mid-calf area to a mid-thigh area, from a mid-calf area to an upper thigh area, from an upper calf area to a lower thigh area, from an upper calf area to a mid-thigh area, from an upper calf area to an upper thigh area, from a lower thigh area to a mid-thigh area, from a lower thigh area to an upper thigh area, from a mid-thigh area to an upper thigh area, and/or from any other suitable lower portion and any other suitable upper portion of a foot and/or leg.

In certain implementations, the superior portion of each of the targeted compression zones terminates at (and/or near) an upper edge of the one or more articles of clothing. The superior portion of each of the targeted compression zones may terminate at a gripping element adapted to facilitate manual application of a superiorly directed force to the superior portion. The gripping element may be formed as, for example, a hole passing through an upper border of the one or more articles of clothing, a thickened portion of the superior portion, a tab, a flap, a loop, a grip, and/or any other suitable object that allows for manual application of a superiorly directed force.

According to some implementations, the system further provides passive graduated compression. Accordingly, a targeted compression zone having a most-inferiorly located inferior portion provides a greatest amount of passive compression, and any targeted compression zones having more-superiorly located inferior portions provide increasingly smaller amounts of passive compression. In certain implementations, one or more of the plurality of targeted compression zones may include a plurality of compression levels along its inferior portion, with a greater level of compression along a more inferior segment of the inferior portion and one or more lesser levels of compression along one or more more-superior segments of the inferior portion. The plurality of compression levels may include a smooth gradient of compression levels.

In some implementations, one or more of the plurality of targeted compression zones includes a material adapted to provide additional functionality such as a cooling effect, a heating effect, a gripping effect, a lower-friction effect, and/or a massaging effect.

In some implementations, one or more of the targeted compression zones may be disposed within the one or more articles of clothing so as to overlay and align with or outline underlying muscles of the lower extremity. In some implementations, the superior portion of one or more of the targeted compression zones joins with its inferior portion to form an inverted T shape. In some implementations, the superior portions of two or more of the plurality of targeted compression zones may join into a single unified superior portion proximate a most superior portion of the respective superior portions.

In some implementations, adjacent zones of the plurality of targeted compression zones may be joined by sections of a less-compressive material. In some implementations, the plurality of targeted compression zones extend in a direction generally anterior-superior to posterior-inferior (or vice versa).

A method in accordance with some implementations of the invention provides targeted compression to portions of a lower extremity using one or more implementations of the system as discussed herein. The method may include a step of applying a superiorly directed force to the superior portion of a targeted compression zone having a most-inferiorly located inferior portion to provide increased compression in a most-inferior portion of the lower extremity. The method may further include sequentially applying superiorly directed forces to the superior portions of subsequent targeted compression zones in an order of ascending inferior portions to provide increased compression in a stepwise fashion from more-inferior to more-superior portions of the lower extremity covered by the clothing system.

A method in accordance with implementations of the invention provides targeted compression to portions of a lower extremity (and/or any other desired body part) using one or more implementations of the system as discussed herein. The method may also include a step of putting on a first item of clothing to the lower extremity (and/or other body part), whereby a superiorly directed force is applied to the superior portion of a targeted compression zone incorporated into the first item of clothing and having a most-inferiorly located inferior portion to provide increased compression in a most-inferior portion of the lower extremity. The method may further include sequentially putting on one or more additional items of clothing layered over the first item of clothing and any subsequently put-on items of clothing, whereby a superiorly directed force is applied to the superior portions of targeted compression zones incorporated into each additional item of clothing in an order of ascending inferior portions to provide increased compression in a stepwise fashion from more-inferior to more-superior portions of the lower extremity covered by the clothing system.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE SEVERAL VIEWS OF THE DRAWINGS

In order that the manner in which the above-recited and other features and advantages of the present invention are obtained, a more particular description of the invention will be rendered by reference to specific embodiments thereof, which are illustrated in the appended drawings. Understanding that the drawings are not necessarily drawn to scale or in proper proportion, and that the drawings depict only typical embodiments of the present invention and are not, therefore, to be considered as limiting the scope of the invention, the present invention will be described and explained with additional specificity and detail through the use of the accompanying drawings in which:

FIGS. 1A-1C respectively illustrate a back, front, and side view of a representative embodiment of a functional sock;

FIGS. 9A-12C illustrate various stages of an illustrative method of using an active stage-by-stage compressive item of clothing in accordance with some embodiments;

FIGS. 13A-17C illustrate various views showing alternate shapes for compression zones in accordance with some embodiments;

FIGS. 18A-19B illustrate some ways in which lengthwise areas of various compression zones may merge to from one or more unitary superior portions in accordance with some embodiments;

FIGS. 20A-26B illustrate some alternate forms for compression zones in accordance with certain compression zone embodiments;

FIGS. 29A-31D illustrate compressive layered clothing systems in accordance with some embodiments;

FIGS. 32A-35E illustrate some illustrative alternate clothing styles in which compression zones are incorporated in accordance with some embodiments;

FIGS. 36A-37C illustrate additional effects that are provided to materials in accordance with certain embodiments;

FIGS. 40A-43 illustrate various gripping elements to facilitate application of a superiorly directed force to compression zones in accordance with some embodiments.

DETAILED DESCRIPTION OF THE INVENTION

Figure 2A:
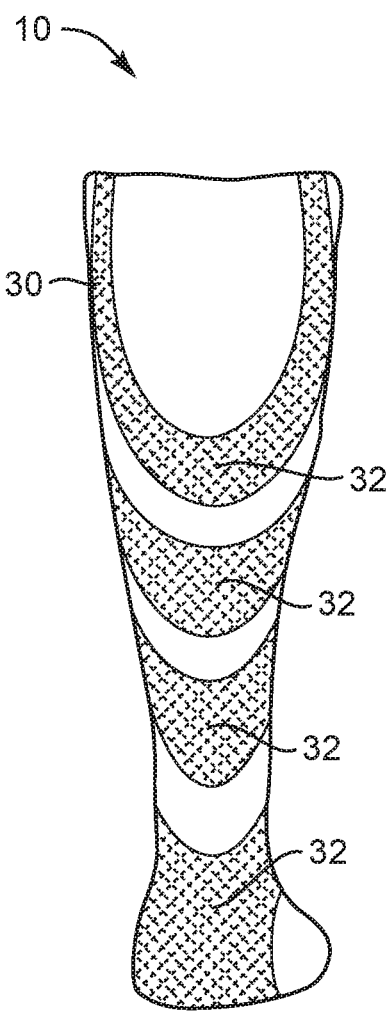
FIGS. 2A-2B respectively show a back view and a side view, showing lengthwise and crosswise areas of compressive zones of the sock in accordance with some embodiments.

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

As embodiments of the invention relate to clothing adapted for use on a lower extremity (and/or a torso, waist, bottom, arm, hand, chest, neck, and/or any other suitable portion) of a human, discussion in the description and in the claims relating to directionality is generally in reference to standard anatomical terms as the item or items of clothing would be typically worn. Thus, terms such as "superior," "superiorly," "proximal," and "proximally" may generally be understood to relate to a general direction of a person's head or body core (e.g., generally upward when a person is standing). Similarly, terms such as "inferior," "inferiorly," "distal," and "distally" may generally be understood to relate to a general direction of away from a person's head or body core (e.g., generally downward when a person is standing). Terms such as "anterior" or "anteriorly" may be understood to relate to a general direction toward the front of the person's body, and terms such as "posterior" or "posteriorly" may be understood to relate to a general direction toward the back of the person's body. Terms such as "lengthwise" may be understood to relate to a general direction along a limb, and terms such as "crosswise" may be understood to relate to a general direction across as opposed to along a limb. As individual anatomical features of individual persons may vary, terms such as those discussed above are not intended to be strictly limiting to any strictly orthogonal direction unless specifically so stated.

Embodiments of the invention provide one or more articles of clothing, including clothing systems, and methods for providing targeted and staged compression to portions of a lower extremity (and/or any other suitable portion of a body), such as a leg of a human. The clothing or clothing system may include individual pieces of clothing, such as socks, sleeves, hosiery, and the like, or multiple-piece clothing systems functioning together to provide targeted and staged compression to the lower extremity.

According to certain embodiments, a system providing targeted compression to portions of a lower extremity (and/or other desired body part) to provide improved venous return characteristics includes one or more articles of clothing individually and/or together having a plurality of targeted compression zones or straps. In some such embodiments, each of the compression zones or straps includes a superior (or proximal) portion extending in at least somewhat of a generally superior-inferior (or proximal-distal) direction (or in other words, in a generally length-wise direction) and an inferior (or distal) portion contiguous with the superior portion and comprising a portion extending in a direction generally orthogonal to the generally superior-inferior direction of the superior portion (or, in other words, generally horizontally or in a generally crosswise direction).

In some embodiments, the system includes a single article of clothing such as a sock, a legging, a calf sleeve, a sleeve, an arm sleeve, a torso sleeve, a glove, a portion of hosiery, a leg of a pair of pants, a stocking, a leg of a pair of tights, tights, a pair of sweat pants, a girdle, a foundation garment, a piece of shapewear, a piece of shaping underwear, a body suit, a unitard, a control slip, a band (e.g., a band for a leg, ankle, waist, arm, wrist, torso, etc.), and/or any other suitable article of clothing. In other embodiments, the system includes a plurality of articles of clothing adapted to be at least partially layered over one another. In such a system, the articles of clothing may each include at least one of a plurality of targeted compression zones. The articles of clothing may include one or more socks, one or more leggings, one or more calf sleeves, one or more sleeves, one or more arm sleeves, one or more bands (e.g., bands for a leg, ankle, waist, arm, wrist, torso, etc.), one or more torso sleeves, one or more gloves, one or more pieces of hosiery, a leg of one or more pairs of pants, one or more stockings, a leg of one or more pairs of tights, one or more tights, one or more one or more pairs of sweat pants, one or more girdles, one or more foundation garments, one or more pieces of shapewear, one or more pieces of shaping underwear, one or more body suits, one or more unitards, one or more control slips, and/or any other suitable articles (or combination of articles) of clothing. In some embodiments, the clothing system includes one or more articles of clothing for each lower extremity, such as a sock for each foot/leg, or a pair of pants having compression zones in each leg.

In certain embodiments, one or more of the targeted compression zones include a pair of superior (or proximal) portions extending in the generally superior-inferior direction (or proximal-distal direction). In some such embodiments, one or more of the superior portions are contiguous with opposite ends of the inferior (or distal) portion. In some instances, a targeted compression zone having a most-inferiorly located inferior portion has a most-anteriorly located superior portion. Additionally, in some embodiments, each compression zone having a subsequently more-superiorly located inferior portion also has a subsequently more-posteriorly located superior portion.

In some embodiments, the superior portions of the plurality of targeted compression zones terminate, at their superior ends, at between approximately zero and approximately eighty degrees (or any subrange thereof) around either side of the article of clothing from a most-anterior portion of the article of clothing. In some such embodiments, the superior portions of the plurality of targeted compression zones terminate, at their superior ends, at between approximately zero and approximately sixty degrees around either side of the article of clothing from a most-anterior portion of the article of clothing. In still other embodiments, the superior portions of the plurality of targeted compression zones terminate, at their superior ends, at between approximately zero and approximately forty-five degrees around either side of the article of clothing from a most-anterior portion of the article of clothing.

In certain embodiments, a targeted compression zone having a most-inferiorly located inferior portion may be adapted to translate a substantially superiorly directed force applied to its superior portions into a compression exerted by its inferior portion at an angle between approximately twenty degrees and approximately seventy degrees, or any subrange thereof (e.g., between approximately forty degrees and approximately fifty degrees). Any targeted compression zones having more-superiorly located inferior portions may be adapted to translate a substantially superiorly directed force applied to their superior portions into compression exerted by their inferior portions at an angle between approximately fifty-five degrees and approximately sixty-five degrees.

In certain of such embodiments, a targeted compression zone having a most-inferiorly located inferior portion may be adapted to translate a substantially superiorly directed force applied to its superior portions into a compression exerted by its inferior portion at an angle of approximately forty-five degrees. Any targeted compression zones having more-superiorly located inferior portions may be adapted to translate a substantially superiorly directed force applied to their superior portions into compression exerted by their inferior portions at an angle of approximately sixty degrees.

According to some embodiments, the inferior portions of the plurality of targeted compression zones extend along a portion of a lower extremity such as from a lower portion of a foot (e.g., a pad, a sole, an arch, a plantar portion, a sural portion, a saphenous portion, one or more toes, a heel, etc.) to a portion of a calf, from a lower portion of a foot, to a portion of a thigh, from a heel to a lower calf area, from a heel to a mid-calf area, from a heel to an upper calf area, from a heel to a lower thigh area, from a heel to a mid-thigh area, from a heel to an upper thigh area, from a lower calf area to a mid-calf area, from a lower calf area to an upper calf area, from a lower calf area to a lower thigh area, from a lower calf area to a mid-thigh area, from a lower calf area to an upper thigh area, from a mid-calf area to an upper calf area, from a mid-calf area to a lower thigh area, from a mid-calf area to a mid-thigh area, from a mid-calf area to an upper thigh area, from an upper calf area to a lower thigh area, from an upper calf area to a mid-thigh area, from an upper calf area to an upper thigh area, from a lower thigh area to a mid-thigh area, from a lower thigh area to an upper thigh area, or from a mid-thigh area to an upper thigh area.

In certain embodiments, the superior portion of each of the targeted compression zones terminates at an upper edge of the one or more articles of clothing. The superior portion of each of the targeted compression zones may terminate at a gripping element adapted to facilitate manual application of a superiorly directed force to the superior portion. The gripping element may be formed as, for example, a hole passing through an upper border of the one or more articles of clothing, a thickened portion of the superior portion, a tab, a flap, or a loop.

According to some embodiments, the system further provides passive graduated compression. Accordingly, a targeted compression zone having a most-inferiorly located inferior portion provides a greatest amount of passive compression, and any targeted compression zones having more-superiorly located inferior portions provide increasingly smaller amounts of passive compression. In certain embodiments, one or more of the plurality of targeted compression zones may include a plurality of compression levels along its inferior portion, with a greater level of compression along a more inferior segment of the inferior portion and one or more lesser levels of compression along one or more more-superior segments of the inferior portion. The plurality of compression levels may include a smooth gradient of compression levels.

In some embodiments, one or more of the plurality of targeted compression zones includes a material adapted to provide additional functionality such as a cooling effect, a heating effect, a gripping effect, a lower-friction effect, and/or a massaging effect.

In some embodiments, one or more of the targeted compression zones may be disposed within the one or more articles of clothing so as to overlay and align with or outline underlying muscles of the lower extremity. In some embodiments, the superior portion of one or more of the targeted compression zones joins with its inferior portion to form an inverted T shape. In some embodiments, the superior portions of two or more of the plurality of targeted compression zones may join into a single unified superior portion proximate a most superior portion of the respective superior portions.

In some embodiments, adjacent zones of the plurality of targeted compression zones may be joined by sections of a less-compressive material. In some embodiments, the plurality of targeted compression zones extend in a direction generally anterior-superior to posterior-inferior.

A method in accordance with embodiments of the invention provides targeted compression to portions of a lower extremity using one or more embodiments of the system as discussed herein. The method may include a step of applying a superiorly directed force to the superior portion of a targeted compression zone having a most-inferiorly located inferior portion to provide increased compression in a most-inferior portion of the lower extremity. The method may further include sequentially applying superiorly directed forces to the superior portions of subsequent targeted compression zones in an order of ascending inferior portions to provide increased compression in stepwise fashion from more-inferior to more-superior portions of the lower extremity covered by the clothing system.

A method in accordance with embodiments of the invention provides targeted compression to portions of a lower extremity using one or more implementations of the system as discussed herein the method may include a step of putting on a first item of clothing to the lower extremity, whereby a superiorly directed force is applied to the superior portion of a targeted compression zone incorporated into the first item of clothing and having a most-inferiorly located inferior portion to provide increased compression in a most-inferior portion of the lower extremity. The method may further include sequentially putting on one or more additional items of clothing layered over the first item of clothing and any subsequently put-on items of clothing, whereby a superiorly directed force is applied to the superior portions of targeted compression zones incorporated into each additional item of clothing in an order of ascending inferior portions to provide increased compression in stepwise fashion from more-inferior to more-superior portions of the lower extremity covered by the clothing system.

FIGS. 1A-1C show various views (e.g., a back view, front view, and side view, respectively) of a representative embodiment of a sock 10. The sock 10 is one example of an item of clothing that may serve as a clothing system or as a part of a clothing system providing staged compression. While the sock 10 is illustrated in FIGS. 1A-1C as an example of such an item of clothing, it should be understood that other items of clothing capable of providing the functionality discussed below with respect to the sock 10 are equally embraced within the scope of the embodiments of the invention and are not in any way disclaimed by the discussion relative to the sock 10.

The sock 10 has a conventional overall shape, and as illustrated is an over-the-calf sock intended to cover the wearer's foot and some to all of the wearer's calf. The sock generally has a cuff region 12 having an edge defining an opening through which the wearer's foot may be inserted into the sock 10, a heel region 14 adapted to be located proximate the wearer's heel when the wearer's foot is fully inserted into the sock 10, an arch region 11 adapted to contact an arch portion of the wearer's foot, and a toe region 16 adapted to be located proximate the wearer's toes when the wearer's foot is fully inserted into the sock 10. As shown, the sock 10 is constructed to join the cuff region 12 to the heel region 14 and the heel region 14 to the toe region 16 to form a single contiguous construct. The area of the sock 10 generally between the cuff region 12 and the heel region 14 generally defines a calf region of the sock 10. Similarly, the area of the sock 10 generally between the heel region 14 and the toe region 16 generally defines a foot region of the sock. The sock may thus be viewed as generally having a calf region or part and a foot region or part.

FIGS. 1A-1C show one embodiment of the sock 10 having a certain pre-defined shape that generally comports with the general shape of the foot and calf of a human. It should be understood that socks 10 may differ in any suitable manner in size, shape, and/or form from that shown in FIGS. 1A-1C: differing socks 10 may have differing amounts of pre-definition in the selected shape, and may also be variously sized to comport with varying anatomies of wearers (e.g., to fit persons having a larger or smaller foot, to fit persons having a larger or smaller calf diameter, to fit persons having a larger or smaller foot-to-knee height, having a defined heel, being a tube sock, having one or more open toes, having one or more closed toes, etc.).

The embodiment of the sock 10 of FIGS. 1A-1C has four strengthened compression zones, straps, or lines (hereafter "zones") that provide active stage-by-stage or level-by-level removal of excess venous blood in the foot and calf in overlying sections of the blood system. While FIGS. 1A-1C illustrate four strengthened compression zones, there could be any suitable number greater or fewer than four compression zones, depending on the desired effect and/or form of the sock 10. As may be seen in FIGS. 1A-1C, a first compression zone 20 begins near the anterior or front of the sock 10 at the edge of the cuff region 12, extends generally downward toward a portion of the sock 10 corresponding to the ankle (a heel, an arch of a foot, and/or another inferior portion of the leg), extends below and/or behind a portion of the sock 10 corresponding to the heel, and then extends generally upward again to terminate at (and/or inferior and/or superior to) the edge of the cuff region 12 adjacent where the first compression zone 20 began. The first compression zone 20 generally has a narrower width proximate both ends near the cuff region 12, and has a broader width proximate the ankle and heel portions of the sock 10. As the first compression zone 20 passes over the heel, it may be termed a compression zone for the calcaneal area.

As may also be seen in FIGS. 1A-1C, in some embodiments, a second compression zone 22 begins at the edge of the cuff region 12 near the front of the sock 10, slightly posterior to the location of the first compression zone 20, extends generally downward, then generally downward and rearward to wrap around the back of the sock 10 slightly above a portion of the sock corresponding to the ankle, and then extends generally forward and upward again to terminate at the edge of the cuff region 12, again slightly posterior to the other location of the first compression zone 20. As with the first compression zone 20, the second compression zone 22 generally has a narrower width proximate both ends near the cuff region 12, and has a broader width in the region where the second compression zone 22 wraps around the back of the sock 10. As the second compression zone 22 passes over a lower portion of the calf, it may be termed a compression zone for the lower third of the calf.

As may also be seen in FIGS. 1A-1C, in some embodiments, a third compression zone 24 begins at the edge of the cuff region 12 moderately near the front of the sock 10, but slightly posterior to the location of the second compression zone 22, extends generally downward, then generally downward and rearward to wrap around the back of the sock 10 slightly above the location where the second compression zone 22 wrapped around the back of the sock 10, and then extends generally forward and upward again to terminate at the edge of the cuff region 12, again slightly posterior to the other location of the second compression zone 22. As with the first compression zone 20 and the second compression zone 22, the third compression zone 24 generally has a narrower width proximate both ends near the cuff region 12, and has a broader width in the region where the third compression zone 24 wraps around the back of the sock 10. As the third compression zone 24 passes over a mid-portion of the calf, it may be termed a compression zone for the middle third of the calf.

As may also be seen in FIGS. 1A-1C, in some embodiments, a fourth compression zone 26 begins at the edge of the cuff region 12 approximately near one lateral edge of the sock 10, again slightly posterior to the location of the third compression zone 24, extends generally downward, then generally downward and rearward to wrap around the back of the sock 10 slightly above the location where the third compression zone 24 wrapped around the back of the sock 10, and then extends generally forward and upward again to terminate at the edge of the cuff region 12, again slightly posterior to the other location of the third compression zone 24 and approximately near the other lateral edge of the sock. As with the other compression zones 20, 22, and 24, the fourth compression zone 26 generally has a narrower width proximate both ends near the cuff region 12, and has a broader width in the region where the fourth compression zone 26 wraps around the back of the sock 10. As the fourth compression zone 26 passes over an upper portion of the calf, such as just below an upper third of the calf, it may be termed a compression zone for the upper third of the calf.

The various compression zones 20, 22, 24, and 26 (and/or fewer or more zones) are formed of a strengthened and more-compressive material than is another portion of the sock. In accordance with some embodiments, the various compression zones 20, 22, 24, and 26 do not directly touch each other and do not cross each other. Indeed, in some embodiments, the various compression zones 20, 22, 24, and 26 are joined or indirectly connected to each other by means of a more elastic (less compressive) connecting material located between them.

Figure 2B:
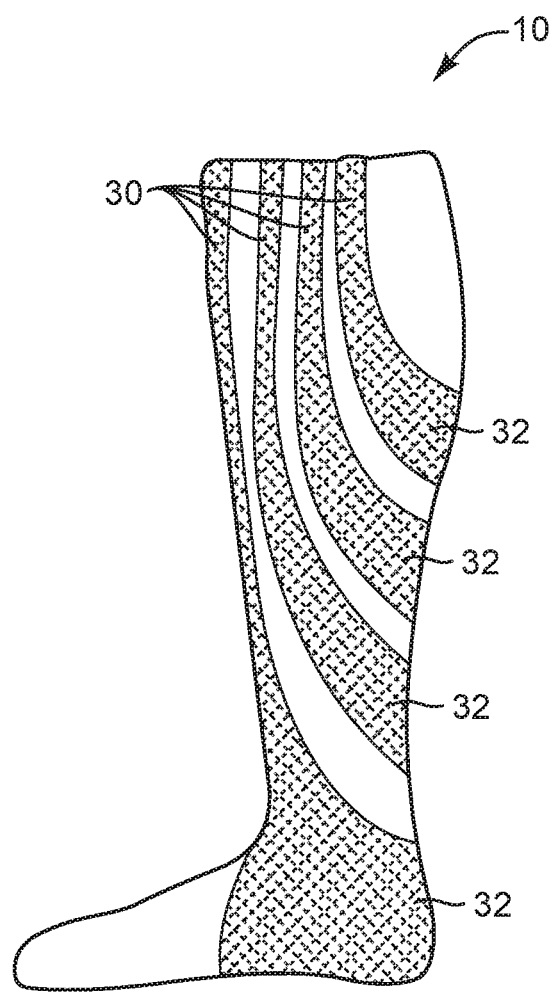

In accordance with some embodiments, the various compression zones 20, 22, 24, and 26 are made of a more-dense and less-elastic material. As shown in FIGS. 2A-2B, the various compression zones 20, 22, 24, and 26 may each be viewed as having two lengthwise areas 30 that reach to the top border of the sock at the cuff region 12. The two lengthwise areas 30 of each of the various compression zones 20, 22, 24, and 26 may be viewed as being joined by a crosswise area 32 (e.g., a transverse, curved, and/or other connecting area) proximate a distal most extent of the various compression zones 20, 22, 24, and 26. As shown in FIGS. 2A-2B, in accordance with some embodiments, the crosswise areas 32 are generally broader than the narrower lengthwise areas 30.

Figure 3A:
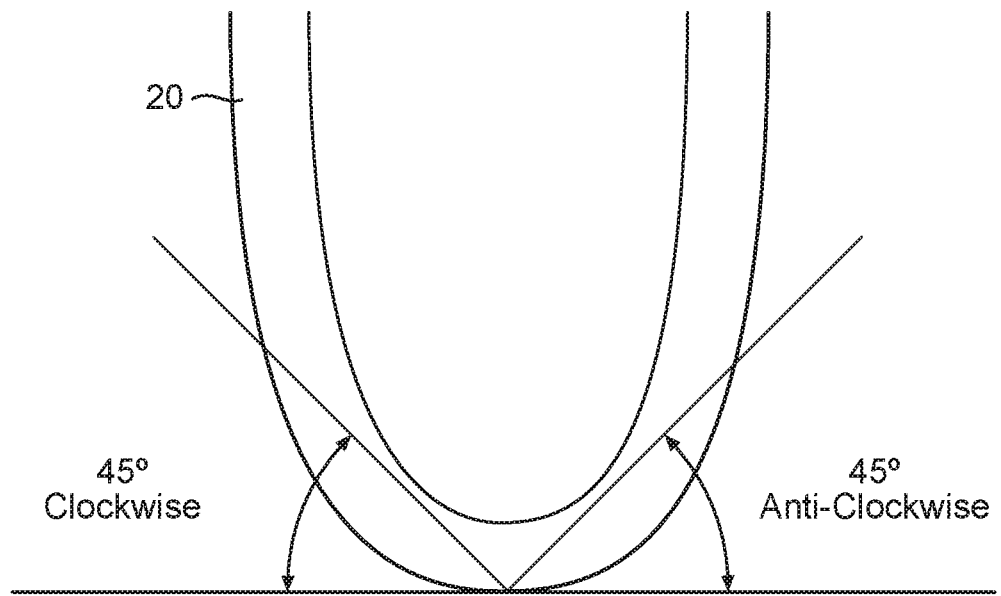
FIGS. 3A-3B show varying angles at which compressive force can be applied by compressive zones in accordance with some embodiments.
Figure 3B:
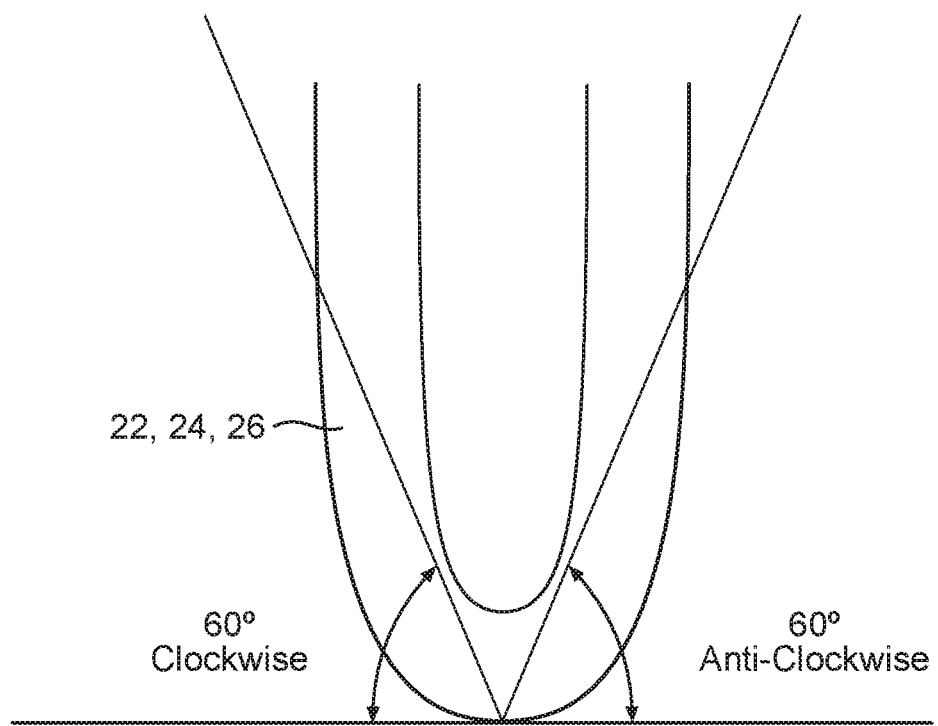

In some implementations, the various compression zones 20, 22, 24, and 26 are made in such a way that by vertical pulling of the lengthwise areas 30 (e.g., at the cuff region 12), a compression is exerted by the various crosswise areas 32. For example, as shown in FIG. 3A, the compression exerted by the crosswise area 32 of the first compression zone 20 is, in accordance with some embodiments, exerted at an angle of between about 30° and about 90° (e.g., about 45°) clockwise and anti-clockwise in relation to the horizontal axis. As is also shown in FIG. 3B, the compression exerted by the crosswise areas 30 of the other compression zones 22, 24, and 26 is exerted at an angle of between about 30° and about 90° (e.g., approximately 60°) clockwise and anti-clockwise in relation to the horizontal axis.

Figure 4:
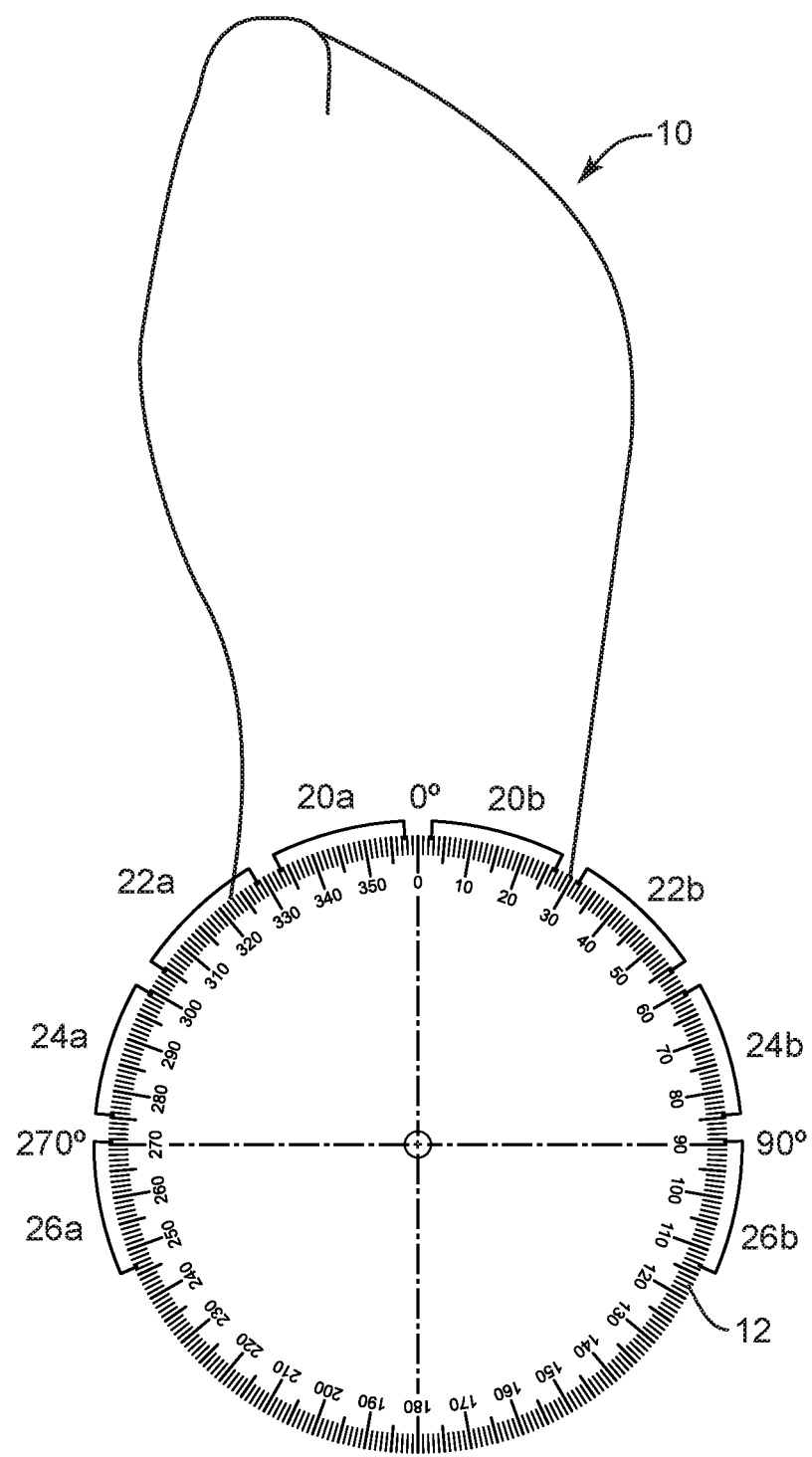
FIGS. 4-8 illustrate top-down views of representative socks having compressive zones terminating near an opening of the socks.

As discussed, the various compression zones 20, 22, 24, and 26 each terminate (in at least some embodiments, twice at the upper edge of the sock 10 in the cuff region 12. To better illustrate this, FIG. 4 shows a top-down view of a representative embodiment of the sock 10. For purposes of the discussion of FIG. 4, the thickness of the sock 10 has been exaggerated. The first compression zone 20 terminates at the cuff region 12 at 20a and 20b, which are both located near an anterior portion of the cuff region 12. The second compression zone 22 terminates at the cuff region 12 at 22a and 22b, which are posterior of 20a and 20b, respectively. The third compression zone 24 terminates at the cuff region 12 at 24a and 24b, which are posterior of 22a and 22b, respectively, and which are slightly anterior of a lateral midline of the sock 10 at the cuff region 12. The fourth compression zone 26 terminates at the cuff region 12 at 26a and 26b, which are posterior of 24a and 24b, respectively, and which are slightly posterior of the lateral midline of the sock 12 at the cuff region 12.

If the cuff region 12 of the sock is viewed as approximating a circle when looked at from top down and taking the most anterior portion of the sock as being zero degrees, each of the various compression zones 20, 22, 24, and 26 has a range of degrees in which it might end. In other words, a limited section or arch may be allocated for the endings of each of the various compression zones 20, 22, 24, and 26. The length of one section or arch can vary, as can the distance between them and their relative positions.

Figure 5:
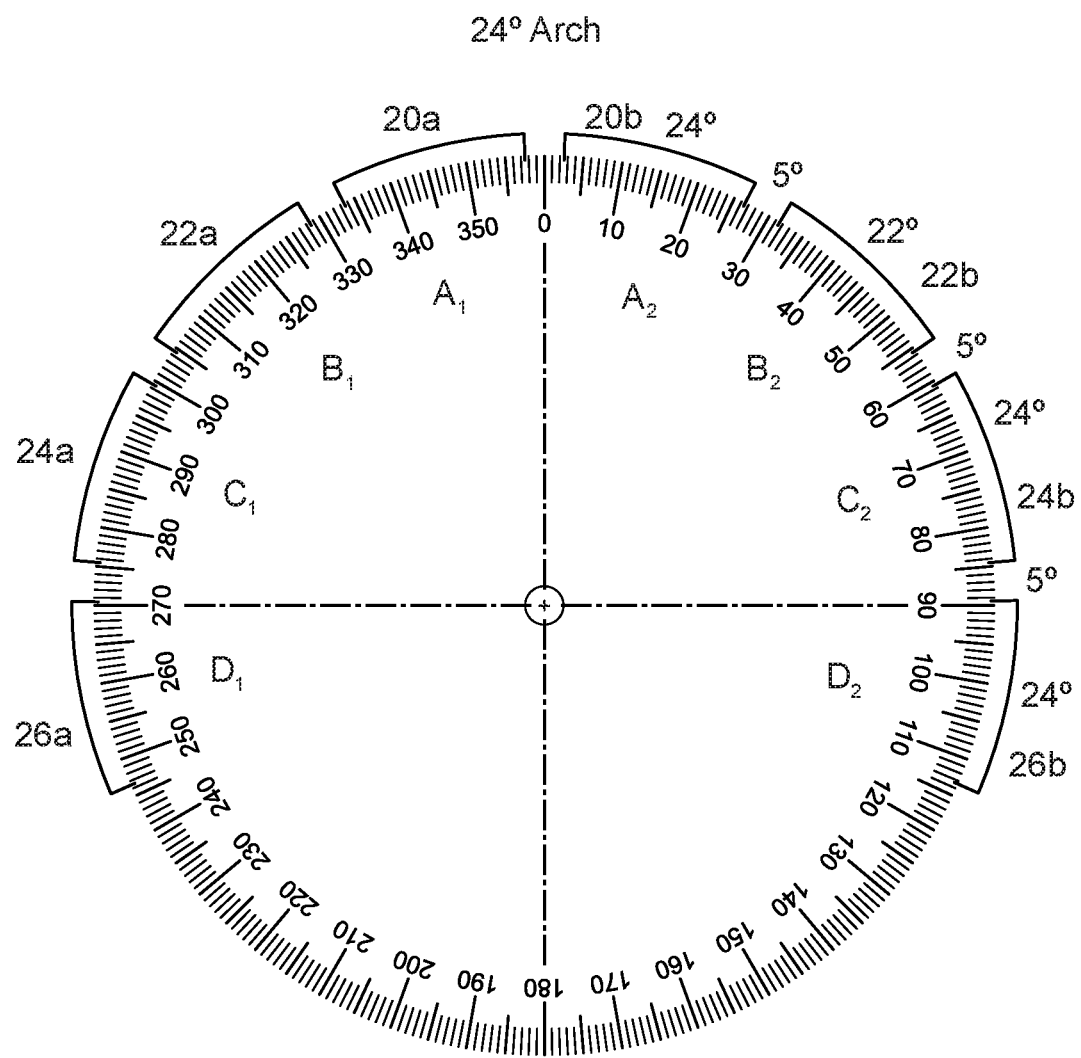

FIG. 5 shows a first example of assigning sections or arches to the ends of the various compression zones 20, 22, 24, and 26. In this example, the length of each section is any suitable length between about 1° and about 90° (e.g., about 24°) and the distance between each section is any suitable length between about 0.1° and about 60° (e.g., about 5°). Thus, in at least some embodiments, when the sock 10 is viewed from the top down, the most anterior approximately 5° of the cuff region 12 will be formed of the more-elastic, less-compressive material, and then the next 24° of the cuff region 12 on either side will be formed of the more-compressive, less-elastic material of the first compression zone 20. Thus, in some embodiments, the termination 20a of the first compression zone 20 will be at a location corresponding to approximately 333° to approximately 357° of the circle, and the termination 20b of the first compression zone 20 will be at a location corresponding to approximately 3° to approximately 27° of the illustrated circle.

As discussed, approximately 5° (or any other suitable length) of the more-elastic, less-compressive material is adjacent to each region of the more-compressive, less-elastic material. Thus, in some embodiments, the termination 22a of the second compression zone 22 will be at a location corresponding to approximately 304° to approximately 328° of the circle, and the termination 22b of the second compression zone 22 will be at a location corresponding to approximately 32° to approximately 56° of the illustrated circle. Similarly, in some embodiments, the termination 24a of the third compression zone 24 will be at a location corresponding to approximately 275° to approximately 299° of the circle, and the termination 24b of the third compression zone 24 will be at a location corresponding to approximately 61° to approximately 85° of the illustrated circle. Also similarly, the termination 26a of the fourth compression zone 26 will be at a location corresponding to approximately 246° to approximately 270° of the circle, and the termination 26b of the fourth compression zone 26 will be at a location corresponding to approximately 90° to approximately 114° of the illustrated circle.

Figures 6A, 6B:
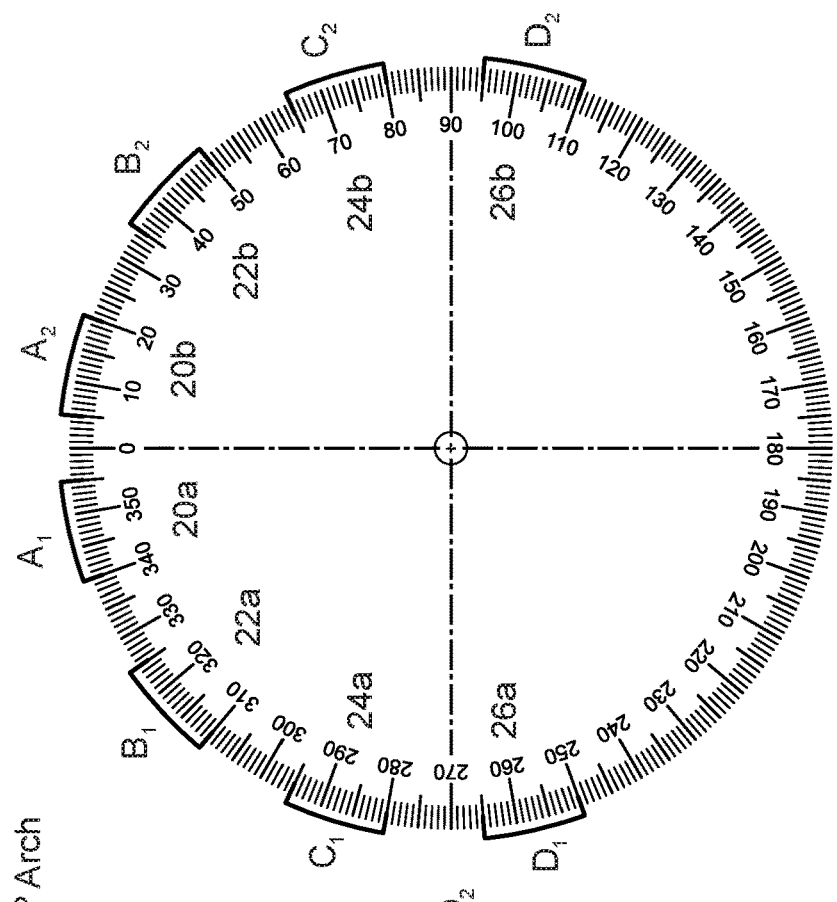

As mentioned above, the length of each arch at the top of the sock 10, the position of each arch at the top of the sock 10, and the distance between them can vary from sock 10 to sock 10. For example, FIGS. 6A-6B illustrates two non-limiting examples in which each arch where the various compression zones 20, 22, 24, and 26 terminate is approximately 15°. In the first, left, example, approximately 10° separates each arch, except approximately 20° separates the two most anterior arches, the terminations 20a and 20b of the first compression zone 20. In the second, right, example, approximately 15° separates each arch except approximately 10° separates the two most anterior arches, the terminations 20a and 20b of the first compression zone 20.

Figure 7B:
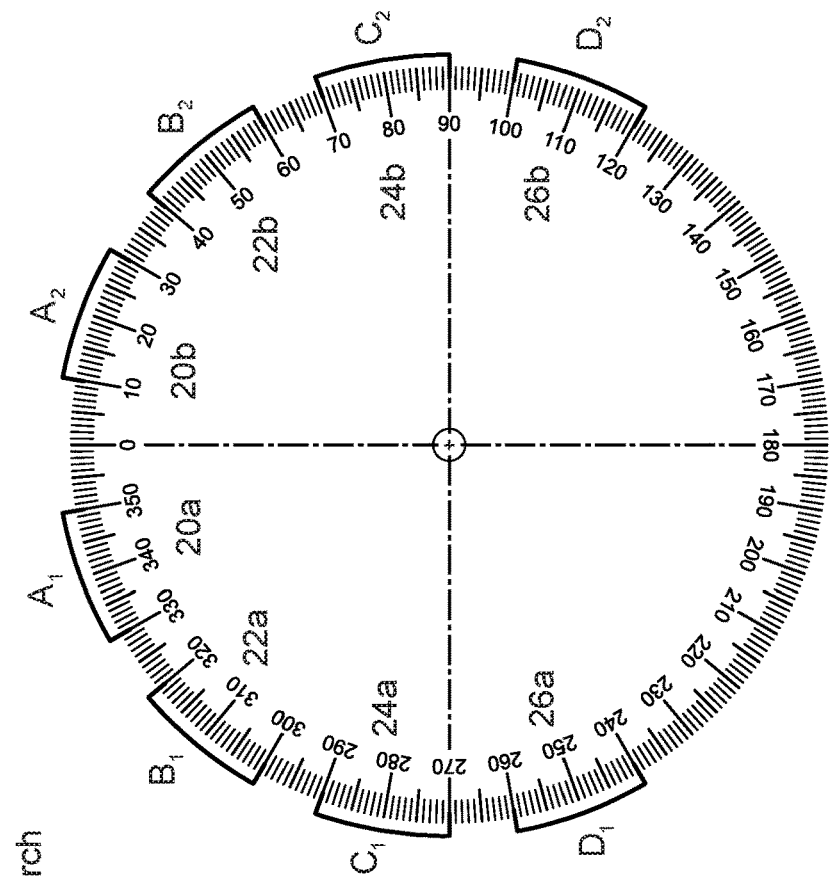

FIGS. 7A-7B illustrates another two non-limiting examples in which each arch where the various compression zones 20, 22, 24, and 26 terminate is approximately 20°. In the first, left, example, approximately 5° separates each arch, except approximately 10° separates the two most anterior arches, the terminations 20*a* and 20*b* of the first compression zone 20. In the second, right, example, approximately 10° separates each arch except approximately 20° separates the two most anterior arches, the terminations 20*a* and 20*b* of the first compression zone 20.

Figure 8B:
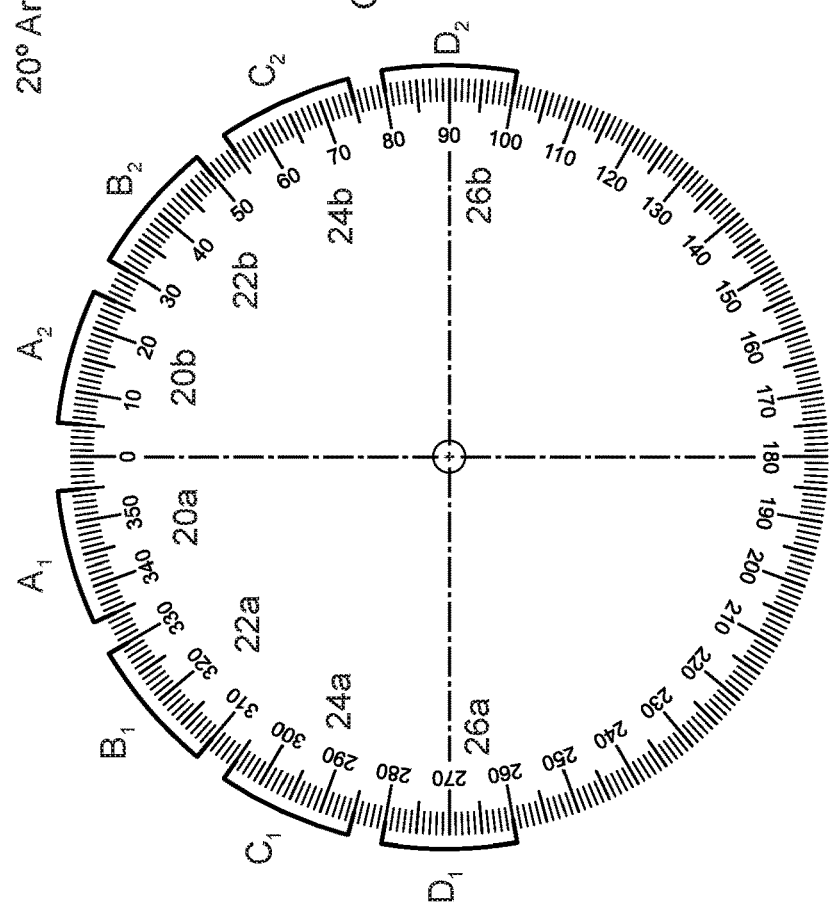
Figure 8:
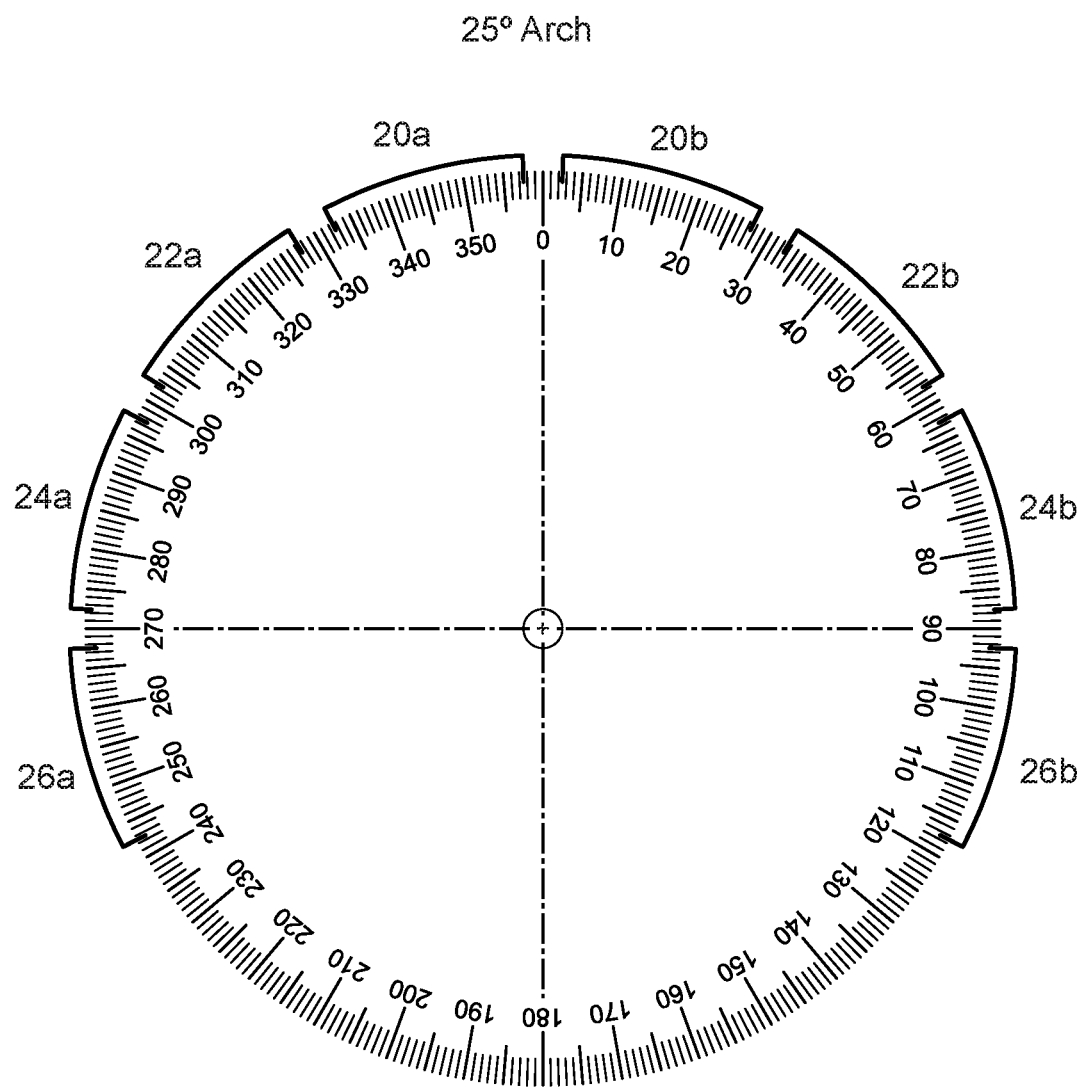

FIG. 8 illustrates one additional non-limiting example in which each arch where the various compression zones 20, 22, 24, and 26 terminate is approximately 25°. In this example, the various arches are separated by approximately 5°.

The size of each arch and the separation between each arch may vary between sock 10 to sock 10, and within each sock 10, as desired and appropriate to provide the desired compressive characteristics to the sock 10. In some embodiments, the arches assigned to the terminations of the various compression zones 20, 22, 24, and 26 fit within the following parameters: 0°≥arch 20*a*≥325°; 0°≥arch 20*b*≥35°; 335°≥arch 22*a*≥295°; 25°≥arch 22*b*≥65°; 305°≥arch 24*a*≥265°; 55°≥arch 24*b*≥95°; 280°≥arch 26*a*≥230°; and 80°≥arch 26*b*≥130° (i.e., in any subrange of the foregoing). Of course, it will be appreciated that these defining characteristics may be varied as appropriate when more or fewer compression zones are present, and that other embodiments may be realized while providing functionality equivalent to or similar to that discussed herein. For example, in some embodiments, as discussed further below, there may be no separation between certain of the arches.

In use, the sock 10 illustrated with respect to FIGS. 1A-8 may be used to provide active, stage-by-stage or level-by-level compression or stimulation for improved venous return in the foot and calf. In other words, the sock 10 may be used to provide staged and targeted compression along each of the various compression zones 20, 22, 24, and 26 in turn. One way this may be achieved is by first putting the sock 10 on, and then pulling and tightening each of the lengthwise areas 30 of the various compression zones 20, 22, 24, and 26 in turn, as is illustrated in FIGS. 9A-12C.

Figure 9C:
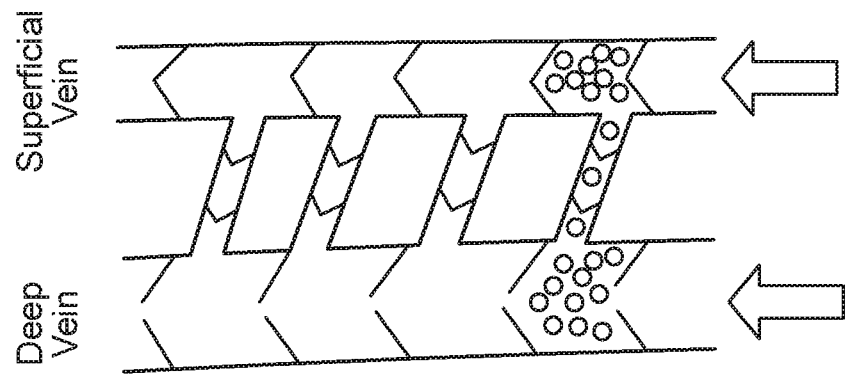
Figure 9B:
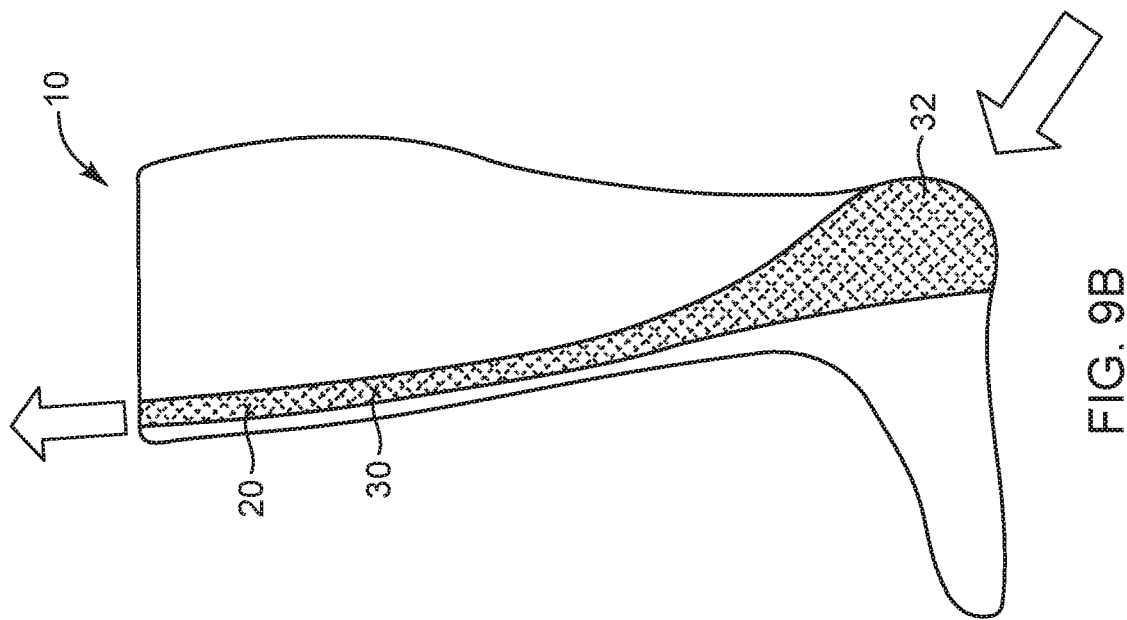
Figure 9A:
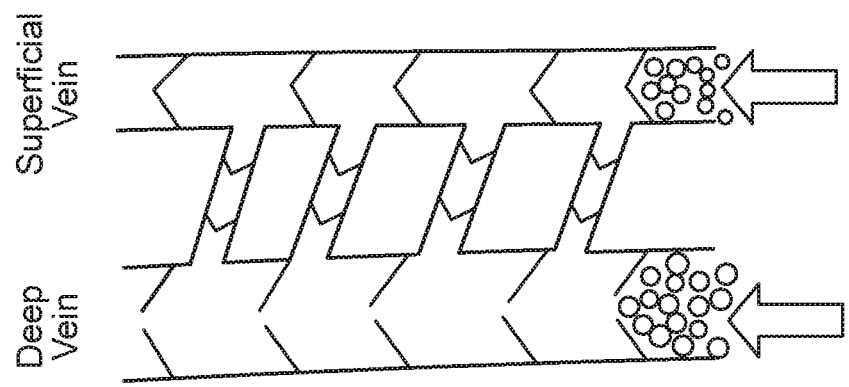

Thus, for example, as is illustrated in FIGS. 9A-9C, once the sock 10 is in place on the wearer's foot and calf, the lengthwise areas 30 of the first compression zone 20 may be manually tightened by pulling them in the vertical direction. This tightening of the lengthwise areas 30 exerts a targeted pressure on the crosswise area 32 of the first compression zone 20. As discussed with respect to FIG. 3A, this targeted pressure may be exerted at any suitable angle (e.g., at an angle of approximately 45° clockwise and anti-clockwise) in relation to the horizontal axis on the calcaneal area. As a result, the venous blood, in accordance with some embodiments, is pushed out from the calcaneal area into the lower third of the calf, as illustrated in FIGS. 9A and 9C. The valves of the venous system prevent the evacuated blood from re-accumulating in the calcaneal area.

Next, the lengthwise areas 30 of the second compression zone 22 may be manually tightened by pulling them in the vertical direction as illustrated in FIG. 10B. This tightening of the lengthwise areas 30 exerts a targeted pressure on the crosswise area 32 of the second compression zone 22. As discussed with respect to FIG. 3B, this targeted pressure may be exerted at any suitable angle (e.g., at an angle of approximately 60° clockwise and anti-clockwise) in relation to the horizontal axis on a lower third of the calf. As a result, the venous blood in the lower third of the calf is pushed out from this area, again upward as illustrated in FIGS. 10A and 10C. The valves of the venous system prevent the evacuated blood from re-accumulating in the lower third of the calf.

Next, the lengthwise areas 30 of the third compression zone 24 may be manually tightened by pulling them in the vertical direction as illustrated in FIG. 11B. This tightening of the lengthwise areas 30 exerts a targeted pressure on the crosswise area 32 of the third compression zone 24. As discussed with respect to FIG. 3B, this targeted pressure may be exerted at any suitable angle (e.g., at an angle of approximately 60° clockwise and anti-clockwise) in relation to the horizontal axis on a middle third of the calf. As a result, the venous blood in the middle third of the calf is pushed out from this area, again upward as illustrated in FIGS. 11A and 11C. The valves of the venous system prevent the evacuated blood from re-accumulating in the middle third of the calf.

Finally, the lengthwise areas 30 of the fourth compression zone 26 may be manually tightened by pulling them in the vertical direction as illustrated in FIG. 12B. This tightening of the lengthwise areas 30 exerts a targeted pressure on the crosswise area 32 of the fourth compression zone 26. As discussed with respect to FIG. 3B, this targeted pressure may be exerted at any suitable angle (e.g., at an angle of approximately 60° clockwise and anti-clockwise) in relation to the horizontal axis on an upper third of the calf. As a result, the venous blood in the upper third of the calf is pushed out from this area, again upward as illustrated in FIGS. 12A and 12C. The valves of the venous system prevent the evacuated blood from re-accumulating in the upper third of the calf.

In this way, by means of periodic and consecutive pulling up on the various compression zones 20, 22, 24, and 26, an active and targeted evacuation of venous blood from the foot and calf is achieved. This targeted evacuation pushes the venous blood upward in a stage-by-stage, level-by-level fashion into the upper blood system. This evacuation considerably improves the venous return of the foot and calf, both from superficial and from deep veins of the lower extremities.

Figure 14A:
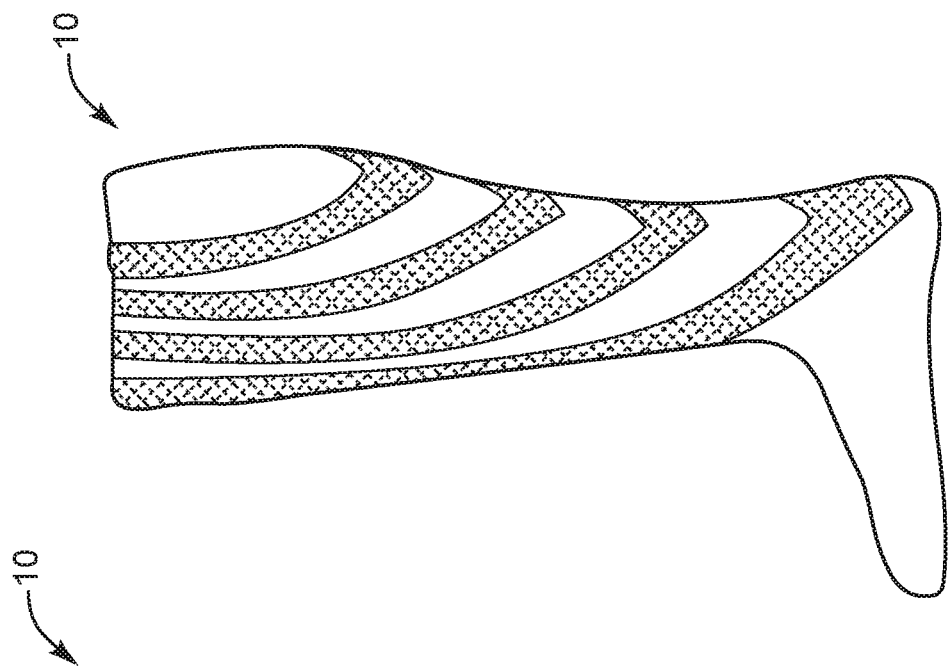
Figure 14B:
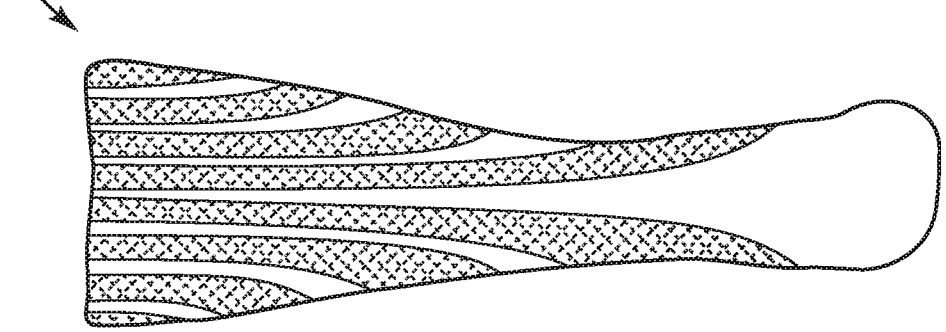
Figure 14C:
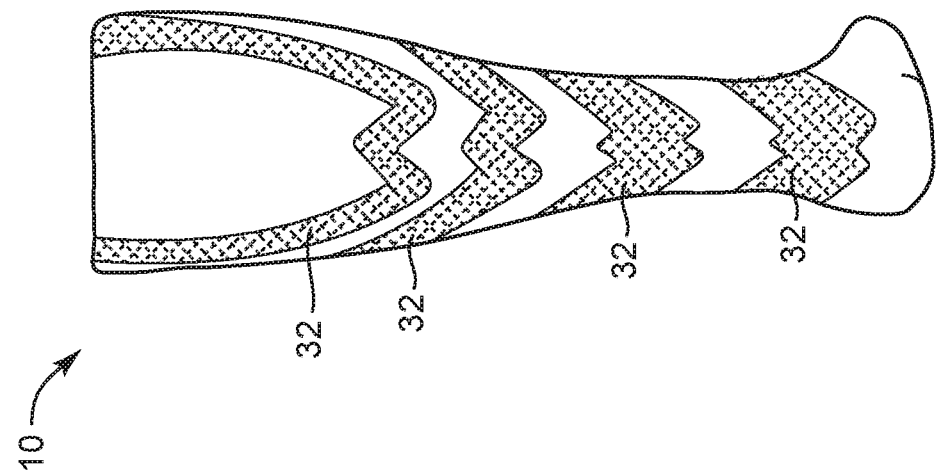
Figures 15A, 15B, 15C:
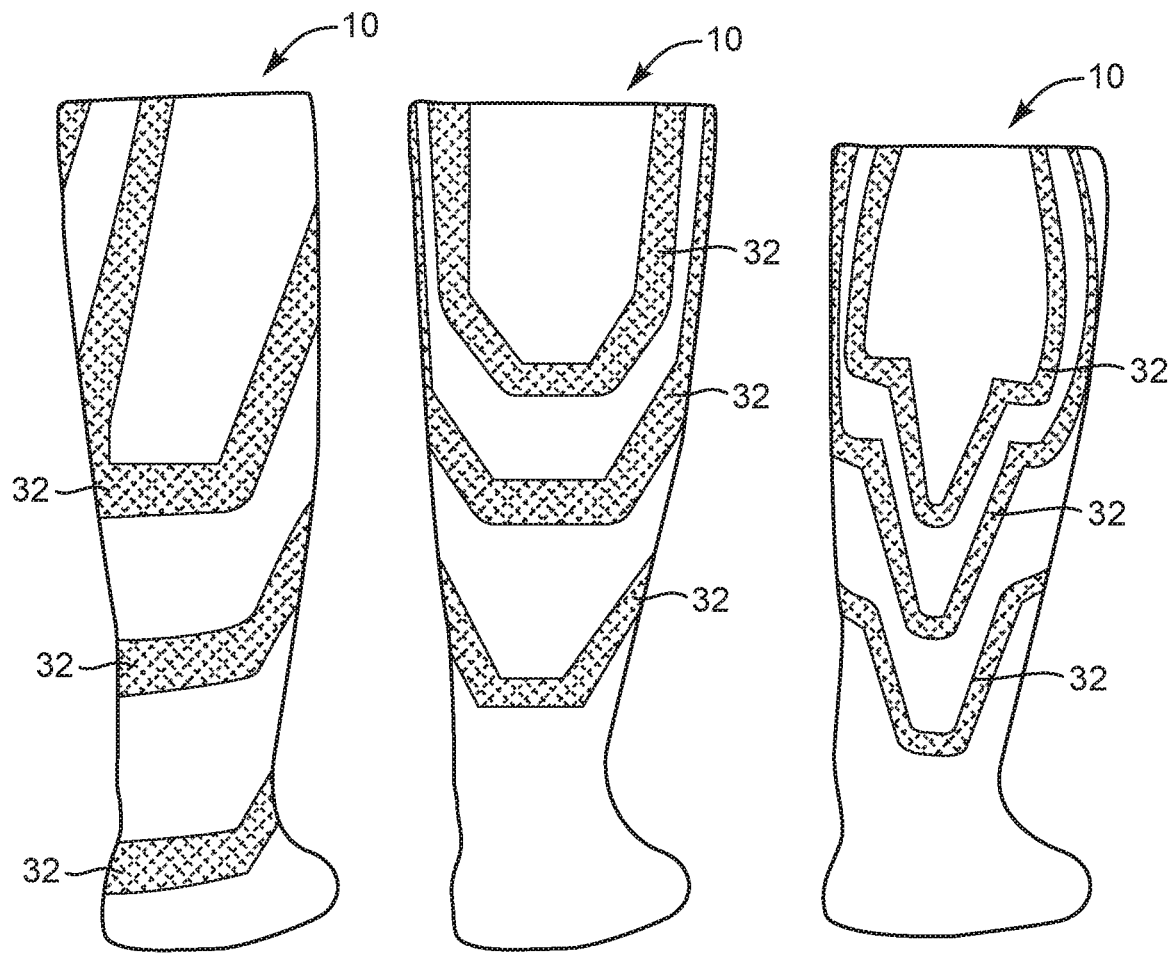
Figures 16A, 16B, 16C:
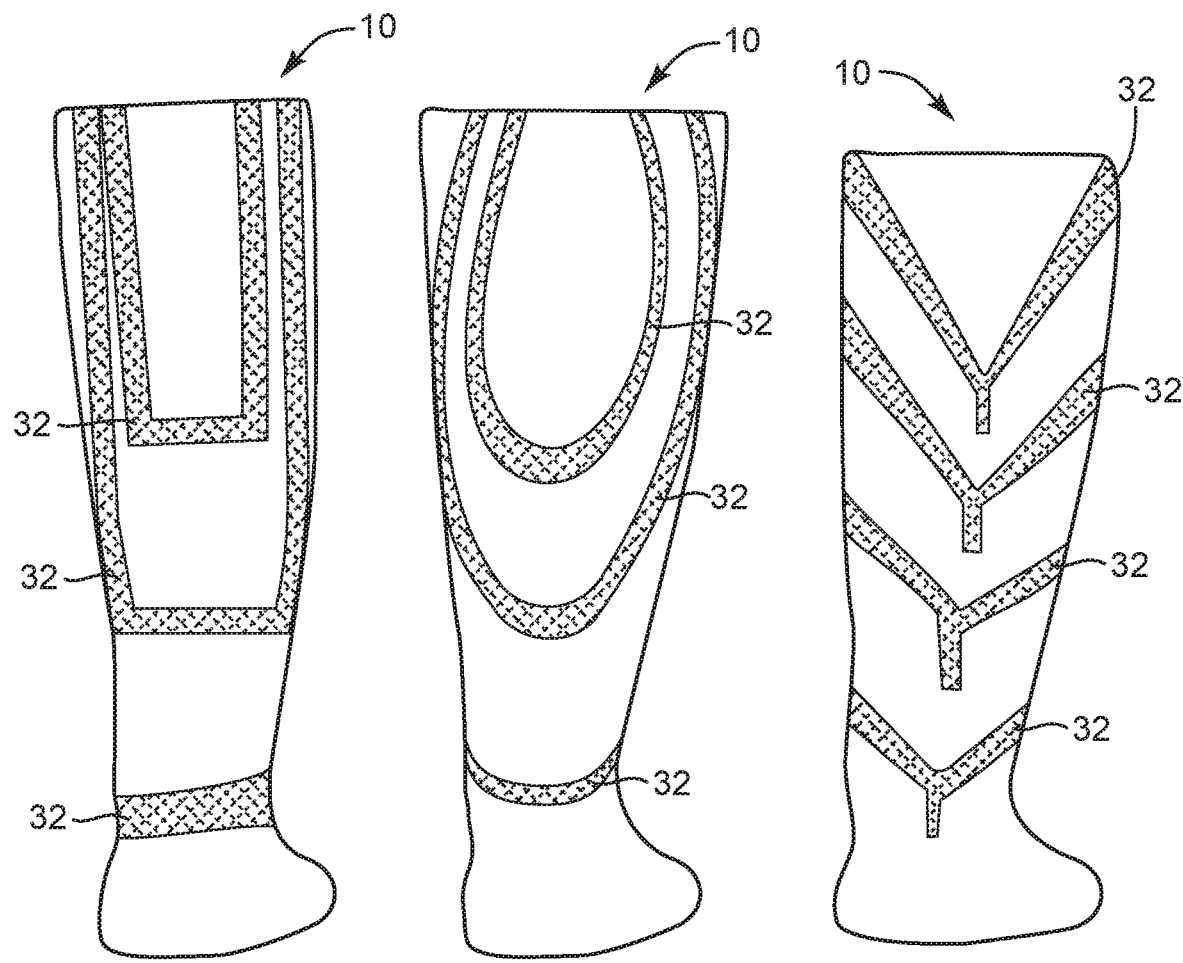

While FIGS. 1A-3B and 9A-12C illustrate some embodiments of the sock 10 having compression zones with crosswise areas 32 that generally represent a gradual curve extending between the lengthwise areas 30, embodiments of the invention are not limited to crosswise areas 32 having such a shape. In that regard, FIGS. 13A-16C illustrate some alternative embodiments having a crosswise area 32 in a non-limiting variety of additional shapes or curves. In the embodiment of FIGS. 13A-13C, the crosswise areas 32 of the various compression zones are bisected by a vertical posterior compression zone 40. In the embodiment of FIGS. 14A-14C, the crosswise areas 32 have a generally W-shaped posterior region. FIGS. 15A-15C illustrate three different embodiments as rear views, the leftmost embodiment having crosswise areas 32 having a trapeze shape, the center embodiment having hexagonal-shaped crosswise areas 32, and the rightmost embodiment having complex-shaped crosswise areas 32. FIGS. 16A-16C illustrate three additional different embodiments with rear views, the leftmost embodiment having crosswise areas 32 having a substantially rectangular shape, the center embodiment having a substantially oval-shaped crosswise areas 32, and the rightmost embodiment having a substantially Y-shaped crosswise areas 32.

While the embodiments illustrated discussed above with respect to FIGS. 1A-3B and 9A-16C all have contiguous compression zones extending from one lengthwise area 30, through the crosswise area 32 to another lengthwise area 30, some embodiments of the invention include and embrace non-contiguous compression zones having one or more interruptions in the various compression zones. By way of non-limiting example, FIGS. 17A-17C illustrate some embodiments of socks 10 having a posterior interruption 42 in some or all of the various compression zones. The posterior interruption 42 may be formed of a similar or identical more-elastic and less-compressive material as the material separating the various compression zones.

Additionally, while the embodiments discussed above with respect to FIGS. 1A-17C each have compression zones with individual lengthwise areas 30 that are separated by, for example, the more-elastic and less-compressive material throughout their superior portions, such separation is not strictly required in all embodiments of the invention. For example, FIGS. 18A-18C illustrate some embodiments where the compression zone having the most-inferior crosswise area 32 (and thus the most anterior lengthwise areas 30) has lengthwise areas that join in their superior portions as a unitary superior portion 50. In this example, the unitary superior portion 50 is centrally and anteriorly positioned, though it need not be in all embodiments. By way of contrast, in this embodiment the other lengthwise areas 30 remain separate throughout their superior portions.

Figure 19A:
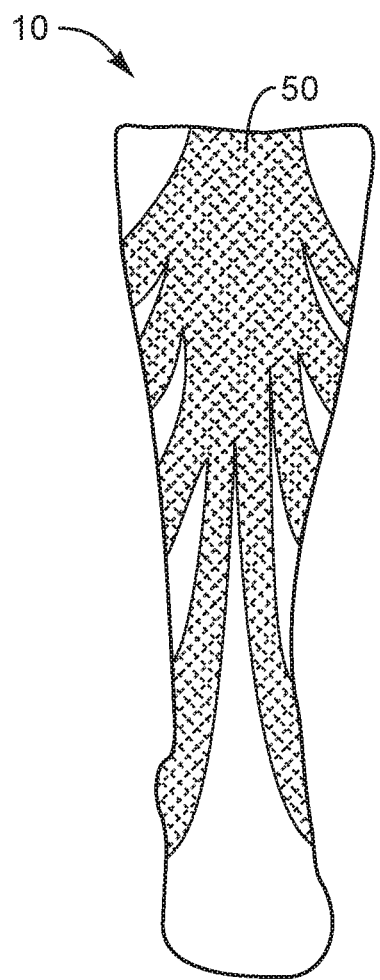
Figure 19B:
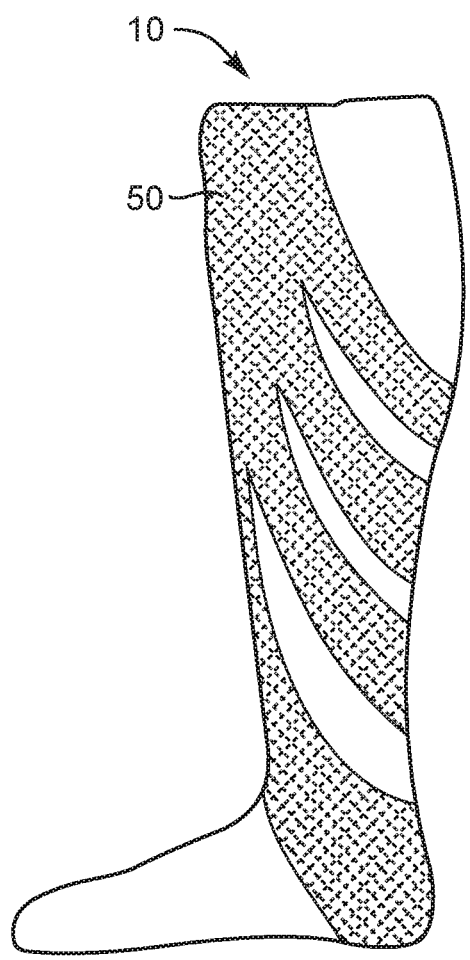
Figure 21C:
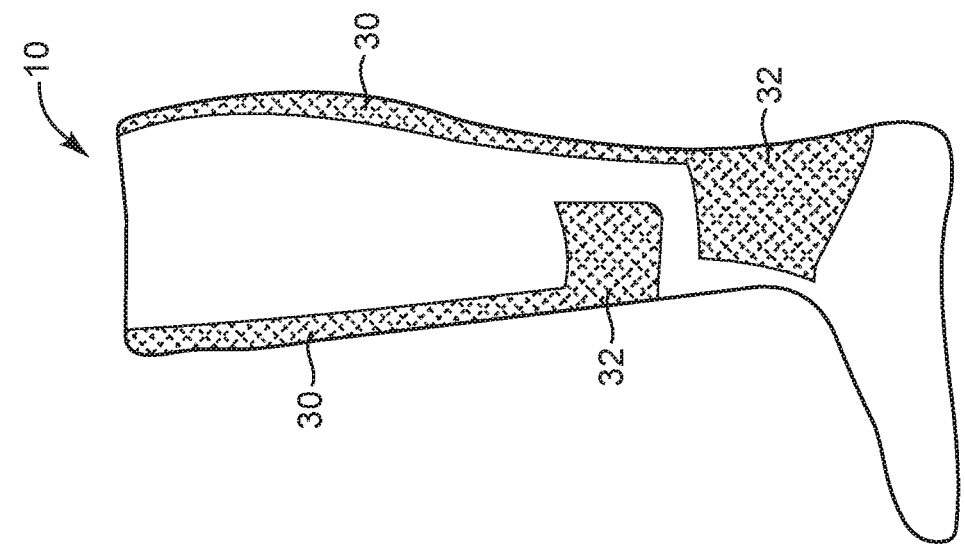
Figure 21B:
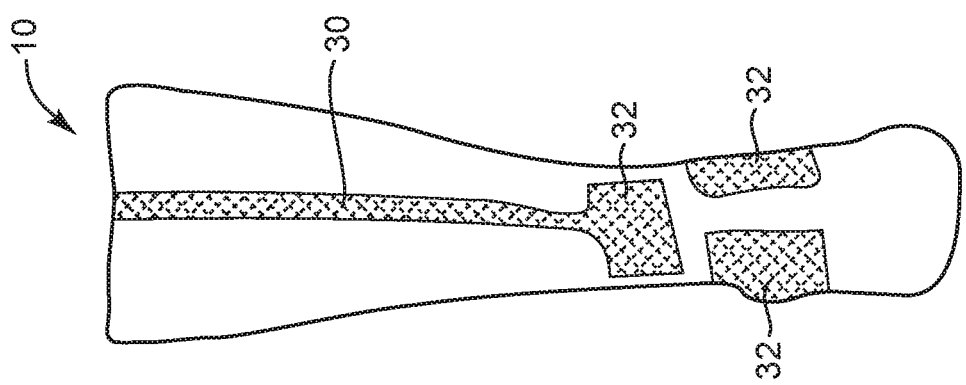
Figure 21A:
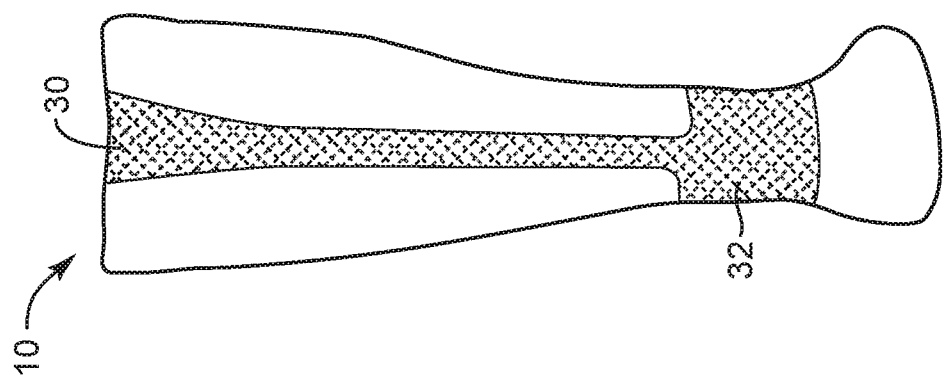
Figure 22C:
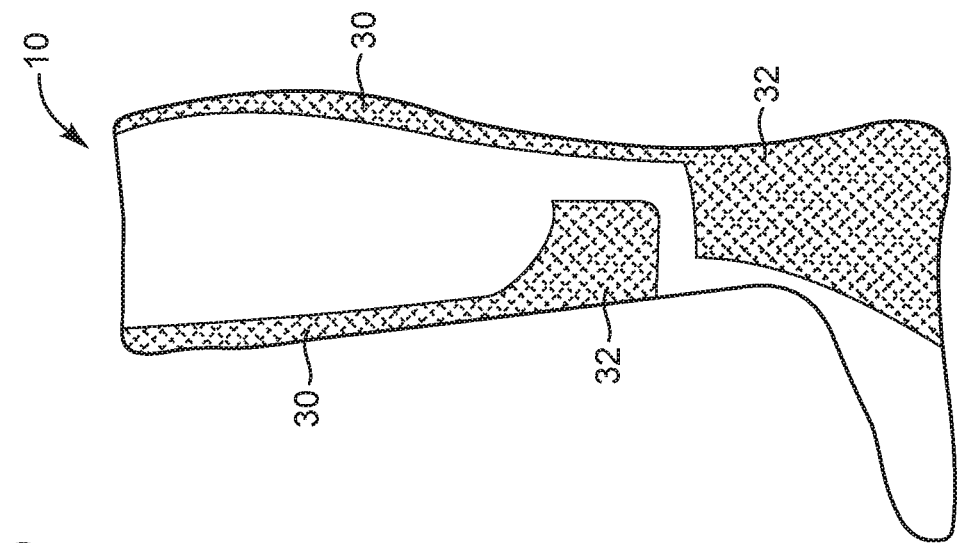
Figure 22B:
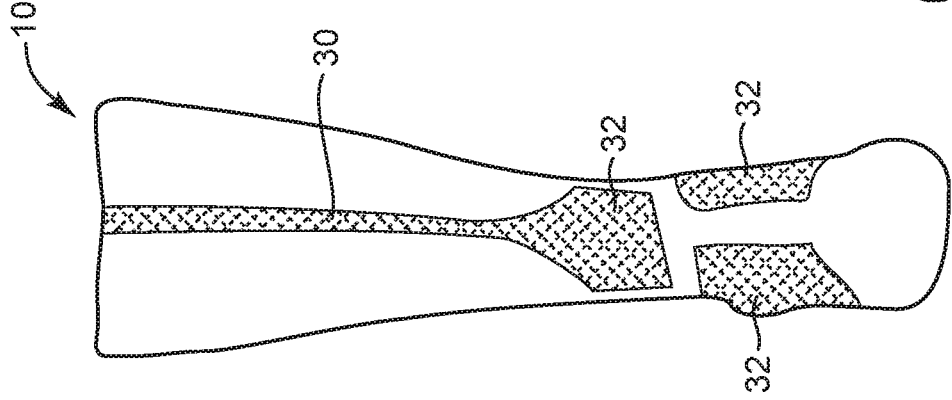
Figure 22A:
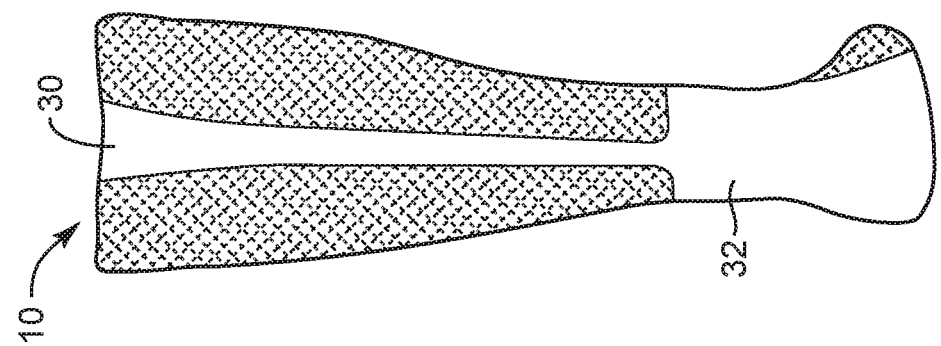
Figure 23:
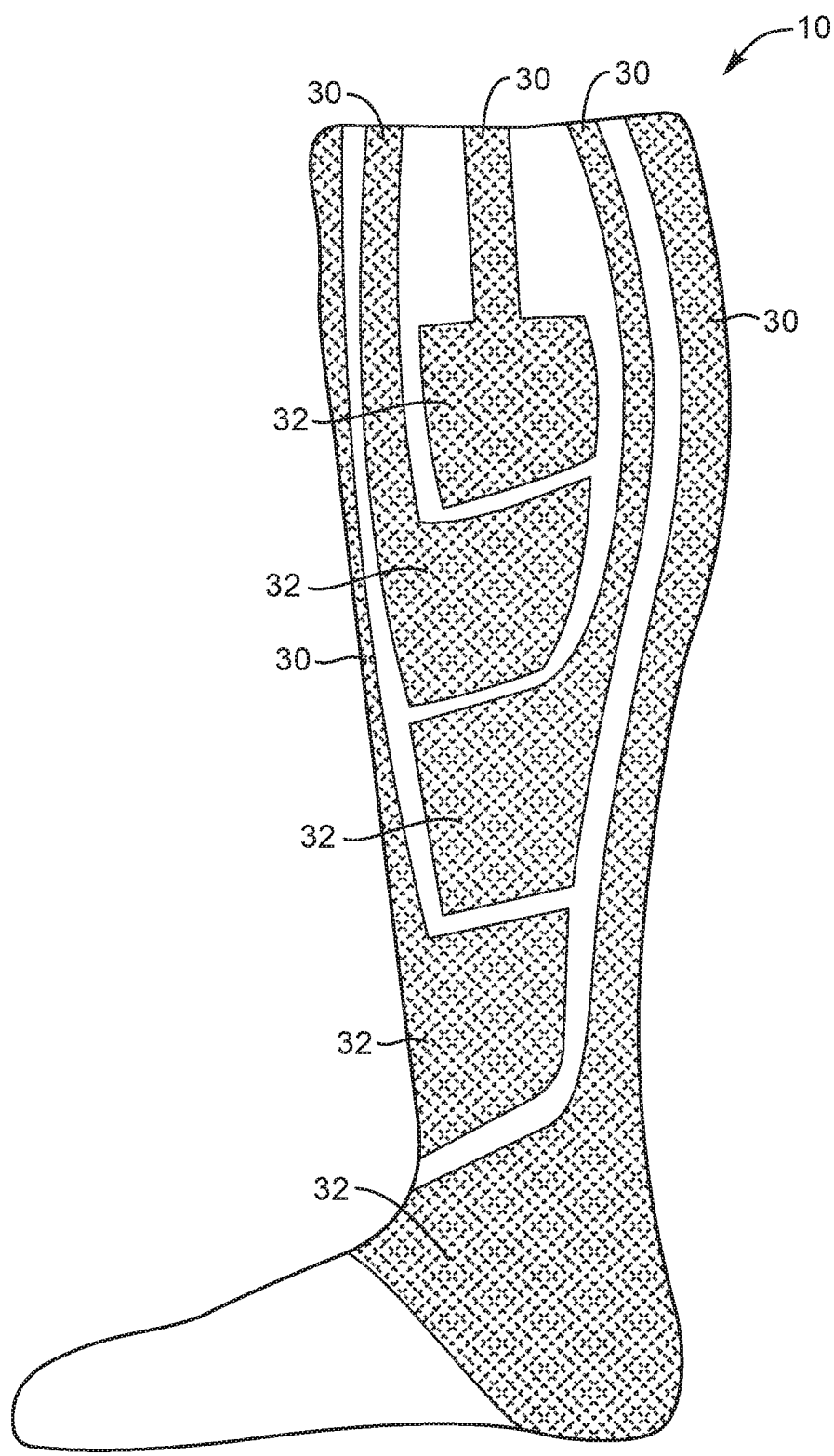

FIGS. 19A-19B, however, illustrate some alternative embodiments in which the superior portions of all the lengthwise areas 30 of all compression zones join together at the unitary superior portion 50. As may be seen from FIGS. 19A-19B, the various compression zones in these embodiments join the unitary superior portion 50 at different superior-inferior locations (heights) near the anterior portion of the sock 10, but in an alternate embodiment, some or all of the various compression zones may join the unitary superior portion 50 at a same superior-inferior location or height. While FIGS. 18A-19B illustrate situations where only one pair of compression zones or where all pairs of compression zones join the unitary superior portion 50, it should be understood that any intermediate number of compression zones may join the unitary superior portion 50, and that any intermediate number of compression zones may remain separate. Additionally, while FIGS. 18A-19B illustrate a single unitary superior portion 50, it should also be understood that embodiments of the invention may have multiple unitary superior portions 50, such as unitary superior portions 50 on each side of the sock 10.

While embodiments of the sock 10 have been illustrated as generally having a single crosswise area 32 extending contiguously or in an interrupted fashion between two lengthwise areas 30, other embodiments of the sock may have a differing relationship between the lengthwise areas 30 and the crosswise areas 32 of the various compression zones. In other words, the lengthwise areas 30 and the crosswise areas 32 of the various compression zones may assume any of a variety of shapes, including shapes having the crosswise area 32 contiguous with a single one of the lengthwise areas 30. By way of example, FIGS. 20A-23 illustrate some non-limiting examples in which many of the compression zones each assume a generally inverted-T shape, and in which certain of the compression zones assume an inverted flag shape. In each of these examples, the crosswise areas 32 extend laterally to one or both sides of a generally vertical (having a generally superior-inferior direction) lengthwise area 30.

While the embodiments discussed above with respect to FIGS. 1A-19B (crosswise areas 32 extending between two lengthwise areas 30) and with respect to FIGS. 20A-23 (crosswise areas 32 each depending from a single lengthwise area 30) have been illustrated as separate and distinct embodiments, other embodiments are envisioned. Thus, embodiments in which certain of the compression zones are provided as crosswise areas 32 extending between two lengthwise areas 30 and other of the compression zones are provided as crosswise areas 32 each depending from a single lengthwise area 30 are intended to fall within the scope of the various embodiments of the invention described herein.

Figure 24:
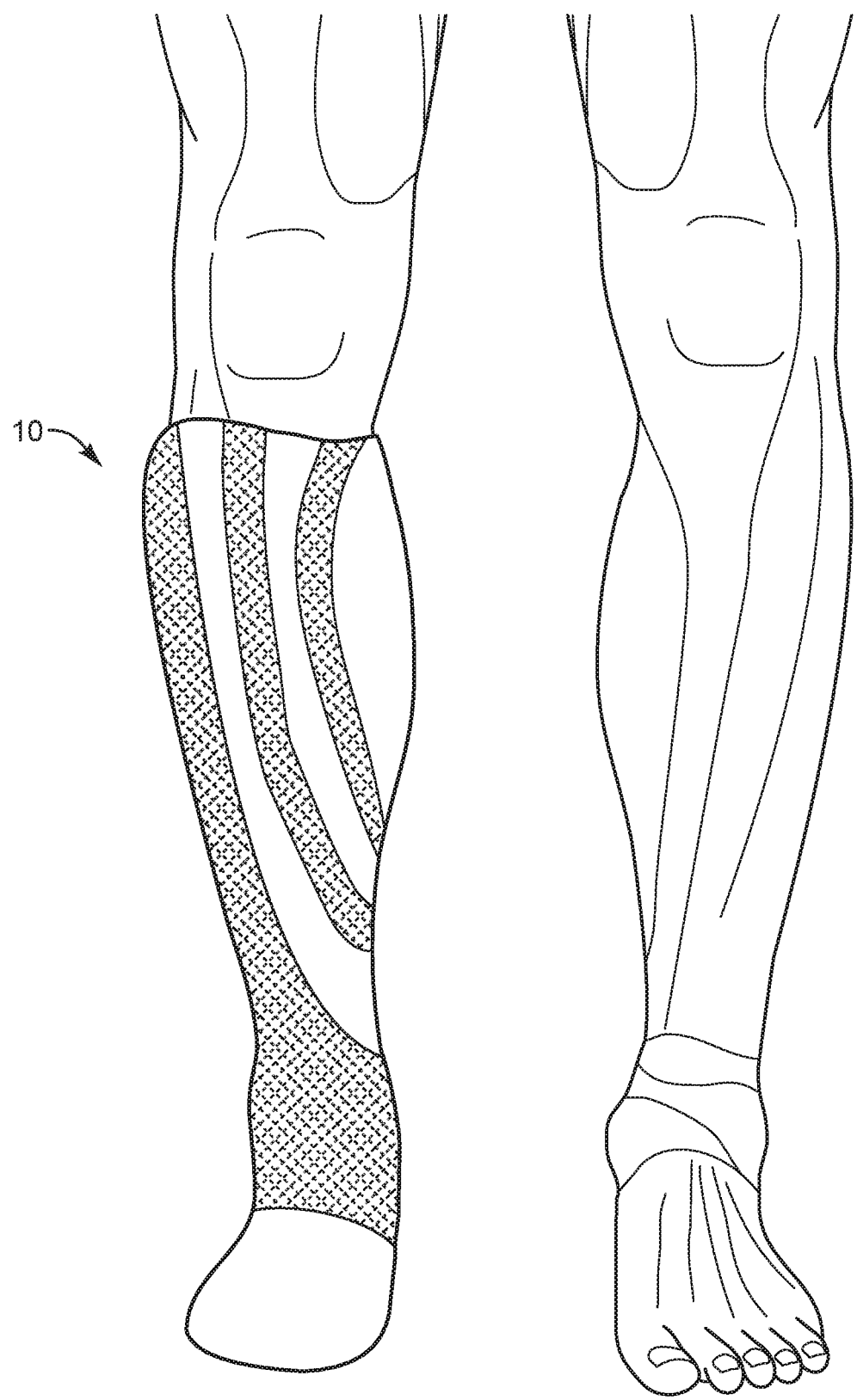
Figure 25:
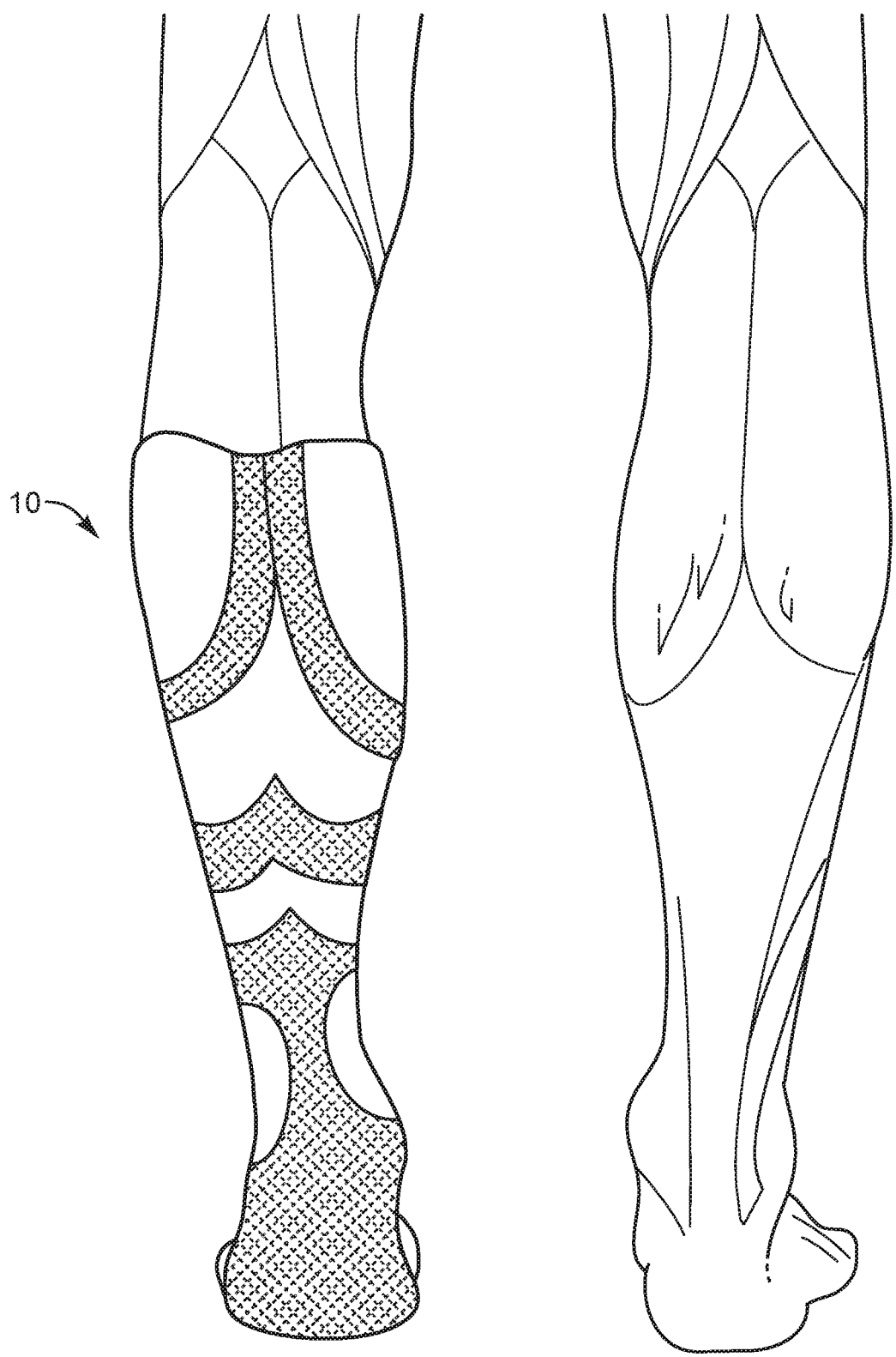
Figure 26A:
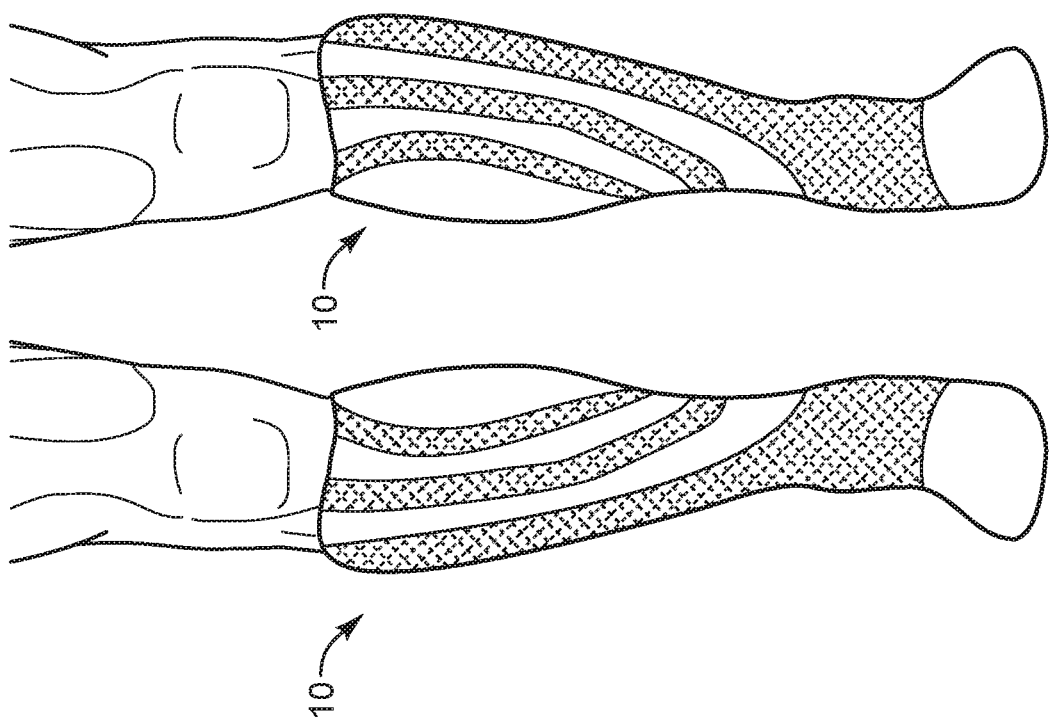
Figure 26B:
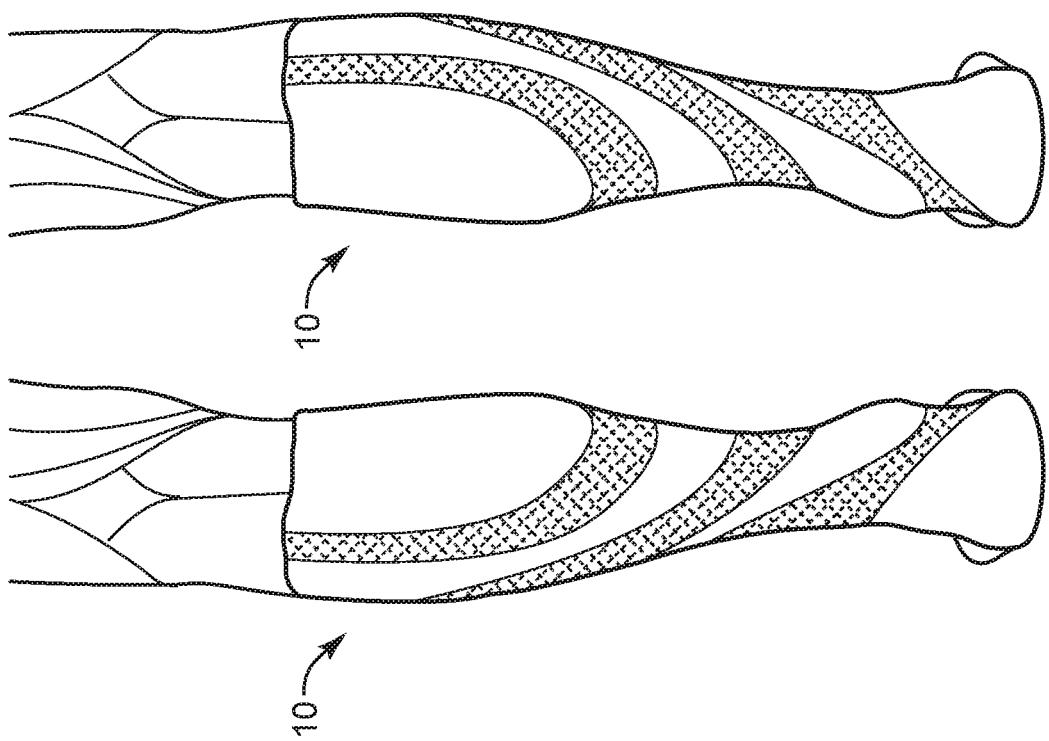

Still other embodiments of the invention provide compression zones that generally correspond to the shape of muscles of the lower extremity. For example, FIGS. 24 and 25 illustrate anterior and posterior views, respectively, of an embodiment of the sock 10 in which the compression zones are shaped to generally correspond to the shape of the calf muscle group gastrocnemius. As another example, FIGS. 26A-26B illustrate anterior and posterior views of an embodiment of the sock 10 in which the compression zones are shaped to generally correspond to the shape of each of the two main calf muscles (M. Flexor Digitorum Longus and M. Flexor Hallucis Longus) separately. In such embodiments, as may be appreciated from FIGS. 24-26B, each sock 10 may thus have compression zones that may be inclined toward the inner part of the calf, and left and right socks 10 may be symmetrical mirror images of each other.

Figure 27C:
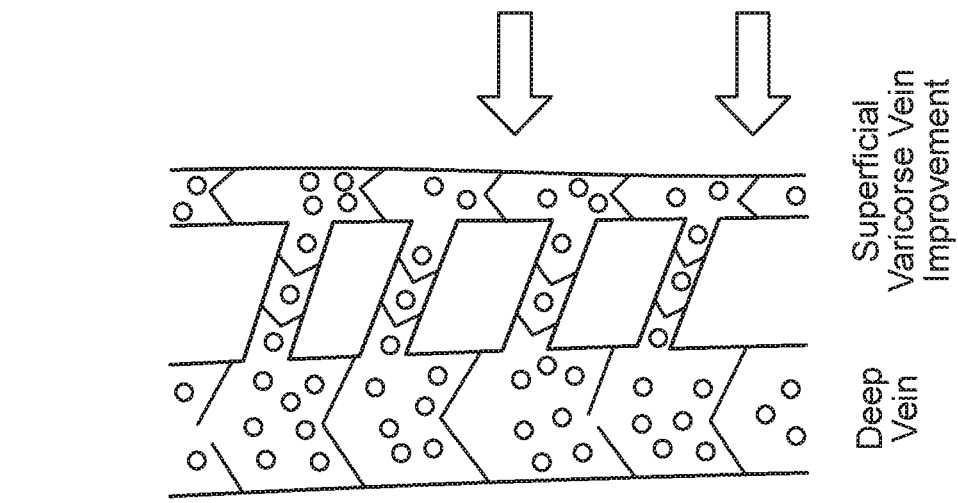
FIGS. 27A-28C illustrate some possible difficulties encountered with use of some traditional circular compression socks.
Figure 27B:
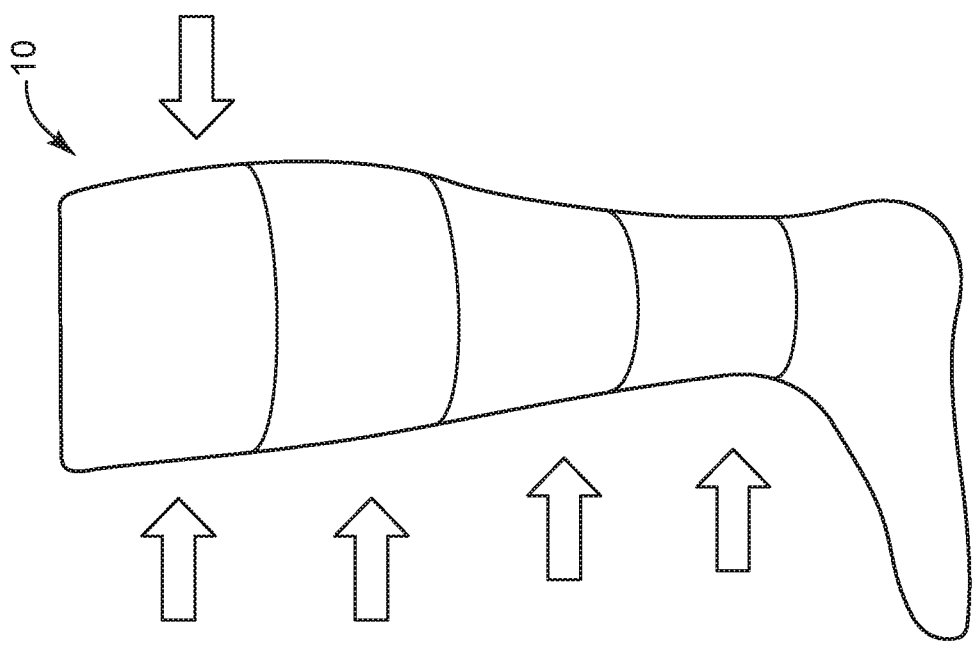
Figure 27A:
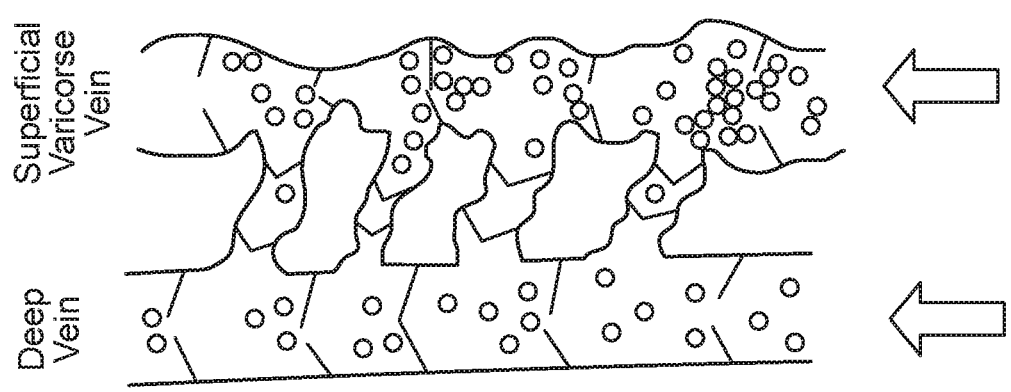

Unlike prior art compression socks providing simple constant circular compression, embodiments of the invention provide lengthwise compression of the lower extremity (e.g., the calf). Traditional compression socks generally squeeze the superficial veins of the calf and partially cause them to cease carrying blood supply. In the case of varicose veins, such action by the compression socks may be justified due to the failure of the varicose vein to function properly; the circular compression sock helps reduce excess blood in the lower leg. Thus, with traditional compression socks, the reduction of venous blood stagnation and buildup is achieved through partial switching off of superficial veins of the calf from blood flow (see FIGS. 27A-27B).

Figure 28C:
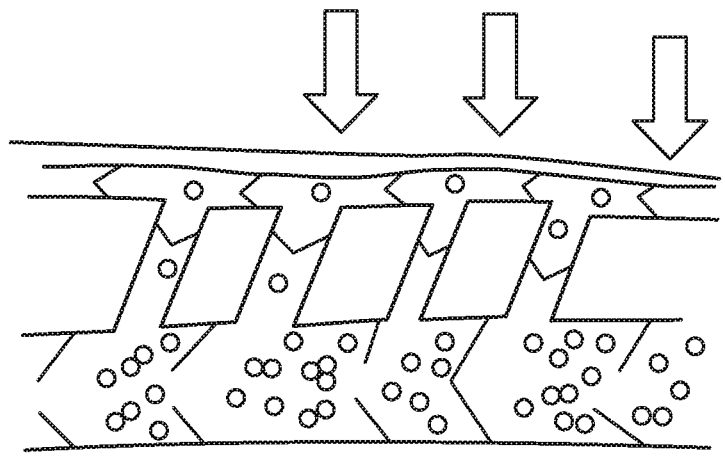
Figure 28B:
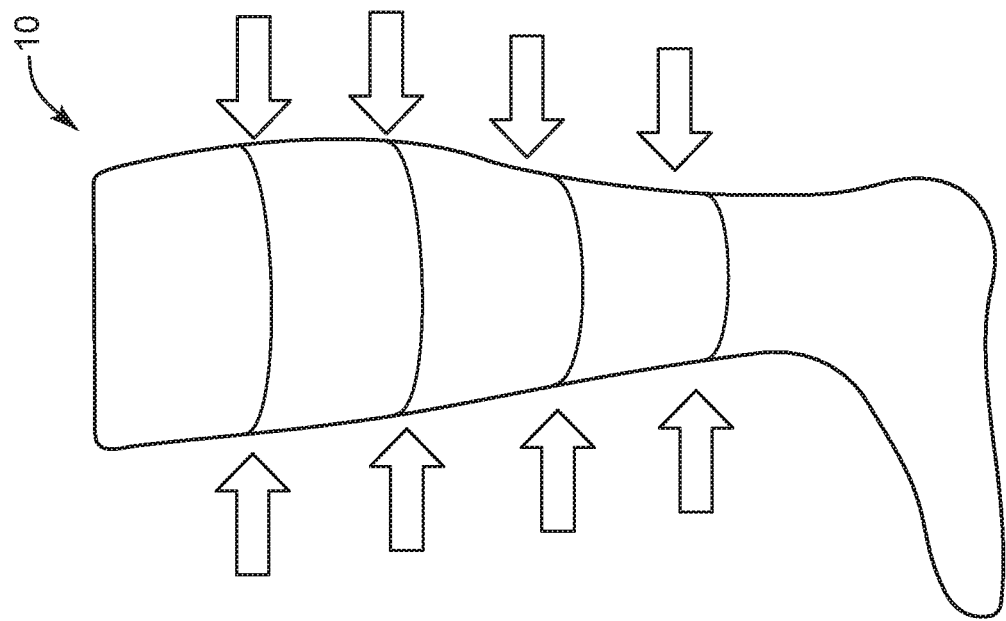
Figure 28A:
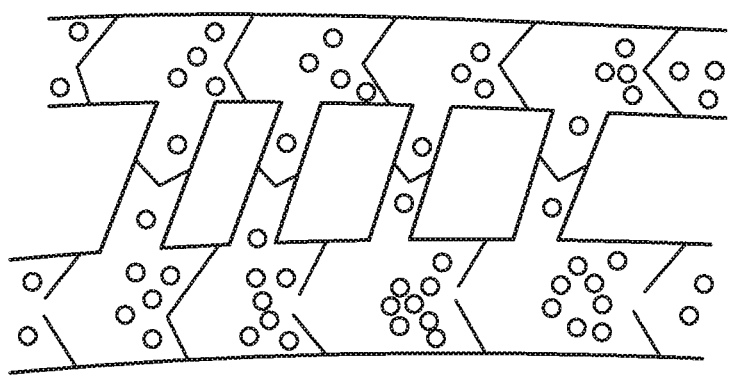

It is common practice, however, to use traditional circular compression socks in a variety of situations where the traditional circular compression may not provide desired results or may even result in harm to the wearer. For example, users of traditional circular compression socks may wear them to protect the veins of the lower extremities while carrying heavy loads, carrying or lifting weights, during exercise or other fitness activities, during flights, during pregnancy, etc. High constant circular compression as provided by traditional compression socks used on lower legs having healthy veins can cause harm to the veins, as is illustrated in FIGS. 28A-28C (e.g., FIG. 28C). Too much compression from ordinary circular compression socks can cause the superficial veins to be over-compressed, restricting blood flow.

For prophylactic prevention and improvement of venous return from healthy veins (not varicose veins) the calf should be exposed to periodic longitudinal compression, but not fixed circular compression as in the traditional compression sock. The calves are sometimes called the "soleus pump" or the peripheral (second) heart, due to their unique ability to pump venous blood back to the heart. When walking, the contracting muscles of the foot and the calf carry out the function of a pump which pushes the venous blood from the lower leg back to heart through deep and superficial veins of the calf. This system works at optimal efficiency when the venous blood can flow in a joint coordinated matter through both deep and superficial veins of the calf. Wearing regular constant circular compression socks on healthy superficial veins, causes the superficial veins to over-compress, resulting in restricted blood flow.

The constant switching off of superficial veins of a calf from work of the "peripheral heart" by means of traditional compression socks worsens operation of the venous pump of a healthy calf. If the socks are worn regularly, once the sock is removed the superficial veins do not return to their maximum efficiency. This use of traditional compression socks is usually more harmful than not on healthy calves and from a medical view it is not reasonable to use circular compression socks for the preventive purposes in which they are often used.

Additionally, the use of traditional compression socks has quite broad medical contraindications: diabetes, atherosclerosis, warm and pulmonary insufficiency, etc. Also after wearing compression socks there could arise issues related to the lack of oxygen that the muscle tissue receives and other complications which are described in detail in published medical literature.

In contrast, embodiments of the sock 10 described herein provides targeted periodic longitudinal compression, but not fixed circular compression. The targeted periodic longitudinal compression provided by embodiments of the invention improves blood outflow from a calf (see FIGS. 9A-12C) without damaging or over-compressing the veins, especially the superficial veins.

In some embodiments of the invention, all of the various compression zones are formed as part of a single item of clothing, such as within a single sock 10, as described in detail above. In other embodiments of the invention, different compression zones may optionally be provided as parts of multiple items of clothing configured to be worn in layers. In some embodiments, the different items of clothing are all similar items of clothing (e.g., are all socks 10 having different compression zones), and in other embodiments, the different items of clothing are more dissimilar items of clothing (e.g. one or more items of clothing are socks 10, but other items of clothing making up the staged compression system include other items of clothing such as leggings, pants, calf sleeves, or the like).

FIGS. 29A-29D shows one example of a layering system for providing targeted periodic longitudinal compression. In this example, the layering system includes three sock layers, a first sock layer 60, a second sock layer 62, and a third sock layer 64. The first sock layer 60 incorporates the first compression zone 20, which may be configured in any of the fashions discussed herein. The second sock layer 62 incorporates the second compression zone 22, which may also be configured in any of the fashions discussed herein. The third sock layer 64 incorporates the third compression zone 24, which may also be configured in any of the fashions discussed herein. In this embodiment, there are only three compression zones 20, 22, and 24 and three sock layers 60, 62, and 64. In other embodiments, there may be more or fewer compression zones and more or fewer sock layers. In some such embodiments, one or more sock layers may include more than one compression zone, such as a two-layer system having four compression zones in total, such as with two compression zones in each sock layer.

When the wearer of the system of FIGS. 29A-29D wishes to use the system to provide targeted periodic longitudinal compression, the wearer first puts on the first sock layer 60 (e.g. by pulling the first sock layer 60 over the wearer's foot and calf). The act of putting on the first sock layer 60 may involve applying a superiorly directed force to the first compression region 20, thereby achieving the effect discussed above with respect to FIGS. 9A-9C, which may occur simultaneously with putting on the first sock layer 60 or subsequently to putting on the first sock layer 60. The wearer then puts on the second sock layer 62 over the first sock layer 60. The act of putting on the second sock layer 62 may involve applying a superiorly directed force to the second compression region 22, thereby achieving the effect discussed above with respect to FIGS. 10A-10C, which may also occur simultaneously with putting on the second sock layer 62 or subsequently to putting on the second sock layer 62.

Next, the wearer puts on the third sock layer 64 over the first sock layer 60 and the second sock layer 62. The act of putting on the third sock layer 64 may involve applying a superiorly directed force to the third compression region 24, thereby achieving the effect discussed above with respect to FIGS. 11A-11C, which may also occur simultaneously with putting on the third sock layer 64 or subsequently to putting on the third sock layer 64. Once all sock layers 60, 62, and 64 are in place, and superiorly directed forces have been applied to the various compression zones 20, 22, and 24 in a staged order from most-inferior to most-superior, the various sock layers 60, 62, and 64 form a completed layered sock system 66, as further shown in FIG. 29. Alternatively to applying the superiorly directed forces as part of the act of putting on the various sock layers 60, 62, and 64, the wearer could first put on all the sock layers 60, 62, and 64, and could then perform steps similar to those discussed above with respect to FIGS. 9A-12C; the final effect is the same.

Where multiple compression zones are located on each sock layer, the method may be slightly modified. If the superiorly directed forces are not applied until all sock layers are in place, the method may proceed as discussed above with respect to FIGS. 9A-12C. If, however, the superiorly directed forces are applied to the lengthwise areas 30 of the compression zones as the sock layers are put on, the superiorly directed forces may be applied first to the lengthwise areas 30 of the compression zone that has a most-inferior crosswise area 32 within the particular sock layer, followed by application of superiorly directed forces to the lengthwise areas 30 of the compression zone having the next-most-inferior crosswise area 32, and so forth until appropriate superiorly directed forces have been applied to all compression zones of the particular sock layer.

Figure 30C:
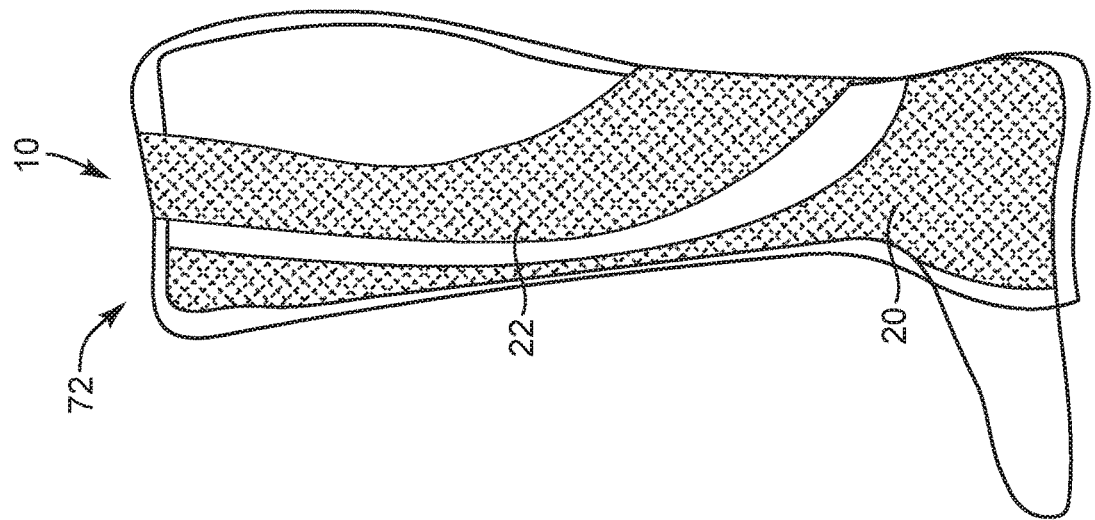
Figure 30B:
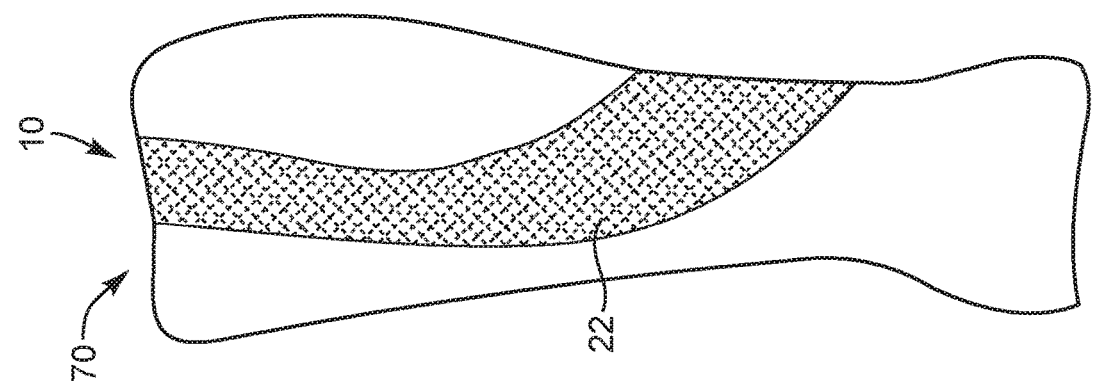
Figure 30A:
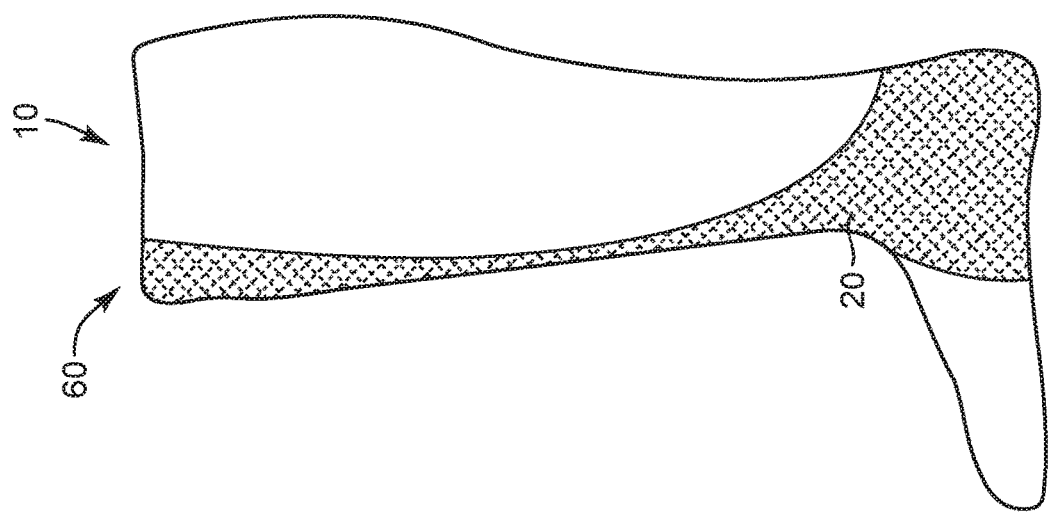
Figure 32B:
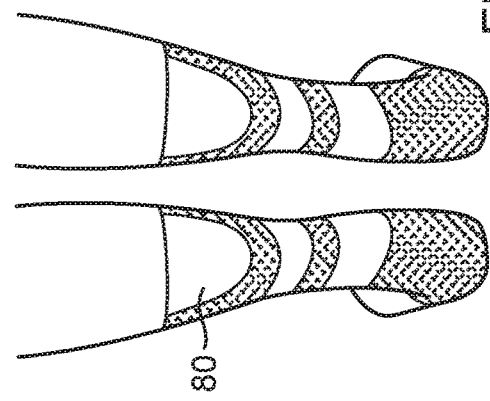
Figure 32D:
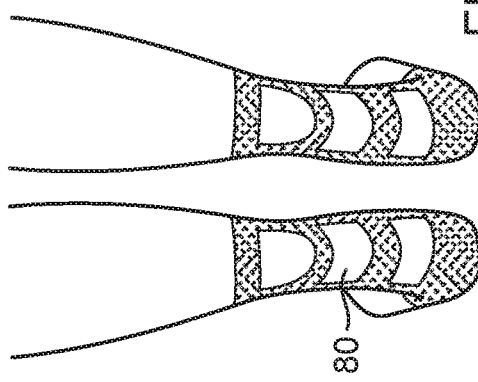
Figure 32A:
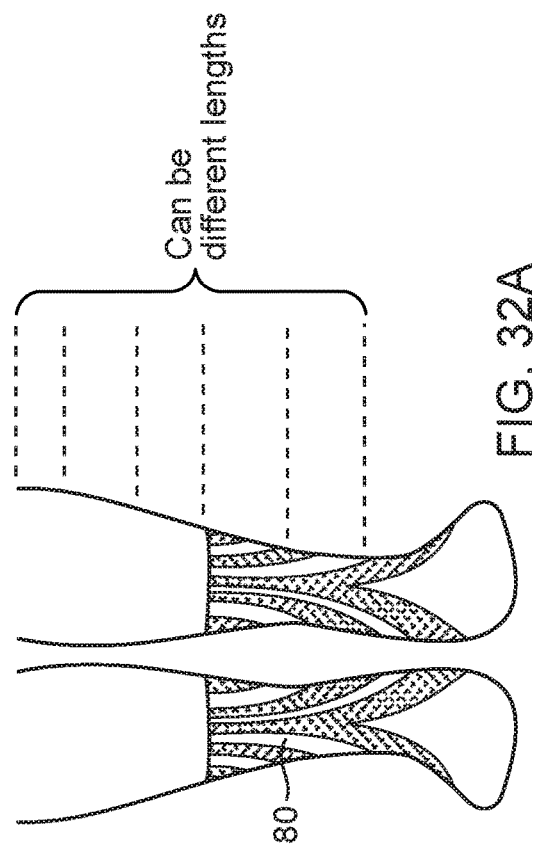
Figure 32C:
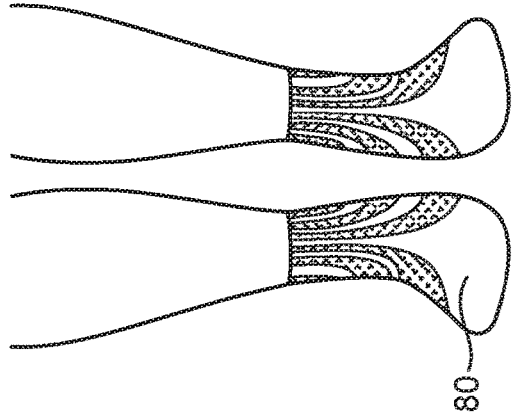
Figure 33A:
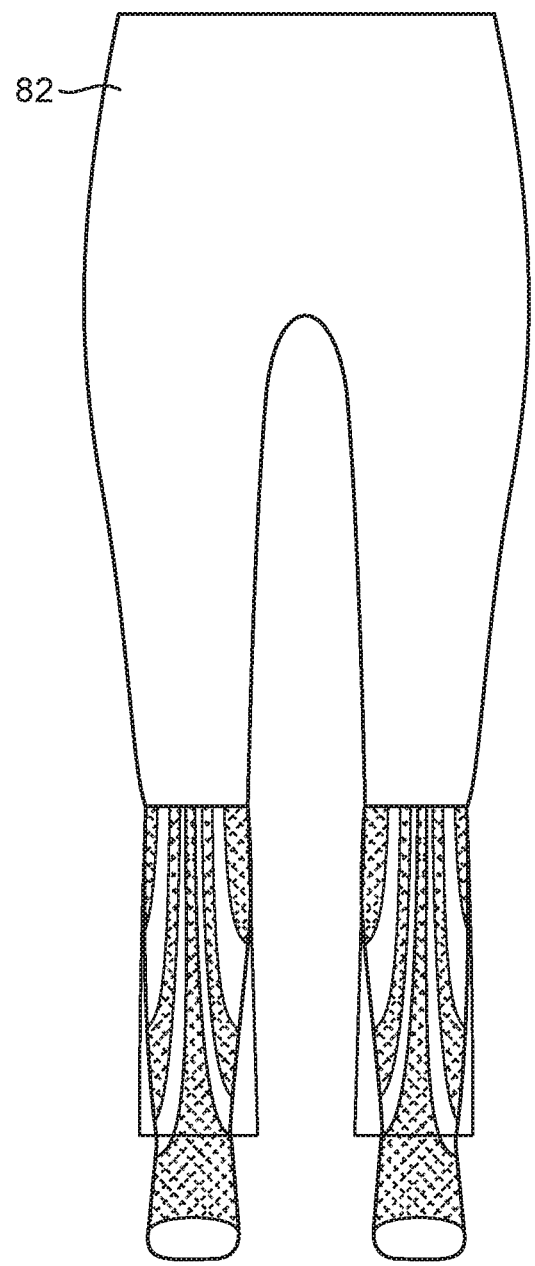
Figure 33B:
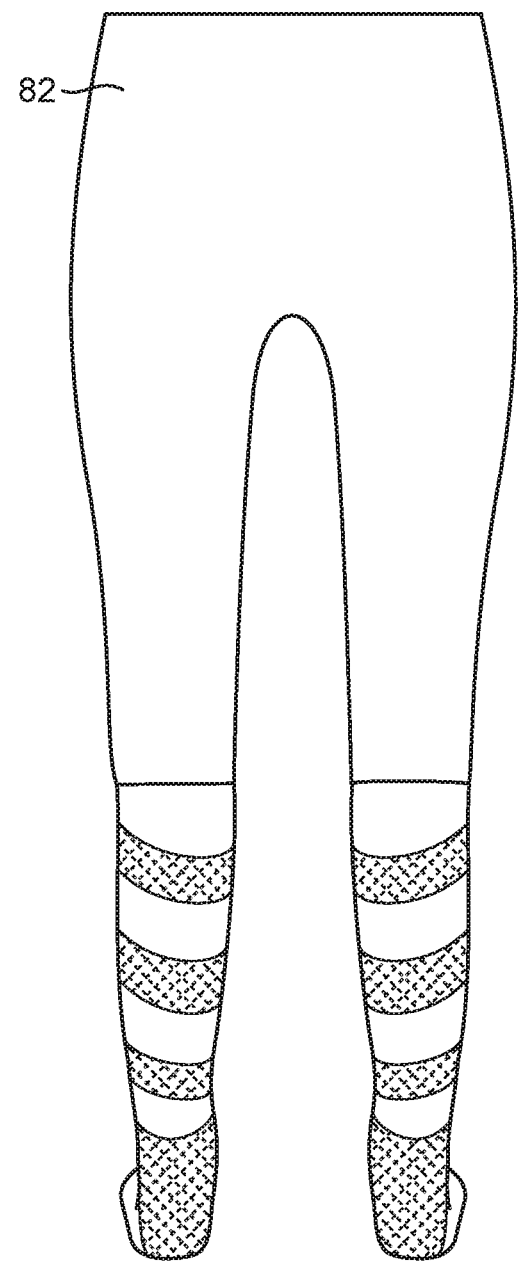

While FIGS. 29A-29D shows an embodiment of the layered sock system 66 in which each of the sock layers 60, 62, and 64 has the form of a complete formed sock, other embodiments may include sock layers that do not have the form of a complete formed sock. FIGS. 30A-31D illustrate two such examples. In the examples of FIGS. 30A-30C, the system includes the first sock layer 60 substantially similarly to the examples of FIGS. 29A-29D, the first sock layer 60 including the first compression zone 20. In this embodiment, a second layer is formed as a footless sock layer 70 in which the footless sock layer 70 omits material that would normally surround a forward portion of the foot forward of the wearer's shin. The omission of material may serve to improve comfort of the system, such as to reduce pressure around the forward part of the foot and/or to improve cooling around the forward part of the foot. Additionally or alternatively, the omission of material may make it easier to put on the footless sock layer 70. Regardless, the footless sock layer 70 includes the second compression zone 22. The system is formed as a complete layered sock system 72 after the wearer puts on the first sock layer 60 and the footless sock layer 70 and either simultaneously or subsequently applies superiorly directed forces to the first compression zone 20 and the second compression zone 22 (note that this layered sock system 72 only includes two compression zones).

FIGS. 31A-31D show another embodiment of a multi-layer system. In this embodiment, the system includes the first sock layer 60 as discussed above with respect to FIGS. 29A-29D, and the footless sock layer 70 as discussed above with respect to FIGS. 30A-30C. The system also includes a calf sleeve layer 74 that includes the third compression zone 24. The calf sleeve layer 74 omits material below approximately the wearer's ankle, which may be done for comfort and/or ease-of-use reasons such as those discussed above with respect to the footless sock layer 70. The system is formed as a complete layered sock system 74 after the wearer puts on the first sock layer 60, the footless sock layer 70, and the calf sleeve layer 74 and either simultaneously or subsequently applies superiorly directed forces to the first compression zone 20, the second compression zone 22, and the third compression zone 24.

While FIGS. 29A-31D illustrate providing various compression zones in various layers or items of clothing, similar or identical compression zones may be provided in other types of clothing as well. The features and benefits discussed herein may be achieved using other types of clothes such as short socks (socks that do not reach as high on the calf), stockings, leggings (including leggings reaching above the knees), trousers, tights, clothes for yoga or other exercises, pants, sleeves, tubes, and the like. Furthermore, layered systems may utilize any combination of such items of clothing as well as any combination including any layers discussed with respect to FIGS. 29A-31D.

For example, the first compression zone 20 might be on the first sock layer 60. The second compression zone 22 might be on the footless sock layer 70. The third compression zone 24 might be on a pair of leggings, etc., until all compression zones are provided. As another example, the first compression zone 20 and the second compression zone 22 might be on the first sock layer 60. The third compression zone 24 and the fourth compression zone 26 might be on a pair of trousers. As another example, the first compression zone 20 might be on a short sock layer while the second and subsequent compression zones 22, 24, etc. might be on a pair of leggings. Regardless of the item(s) of clothing bearing the various compression zones 20, 22, 24, and 26, etc., the various compression zones work together as a common system to provide active step-by-step, level-by-level compression and venous return from the foot and the calf (or other applicable portions of the lower extremity) back to the heart.

Figure 34A:
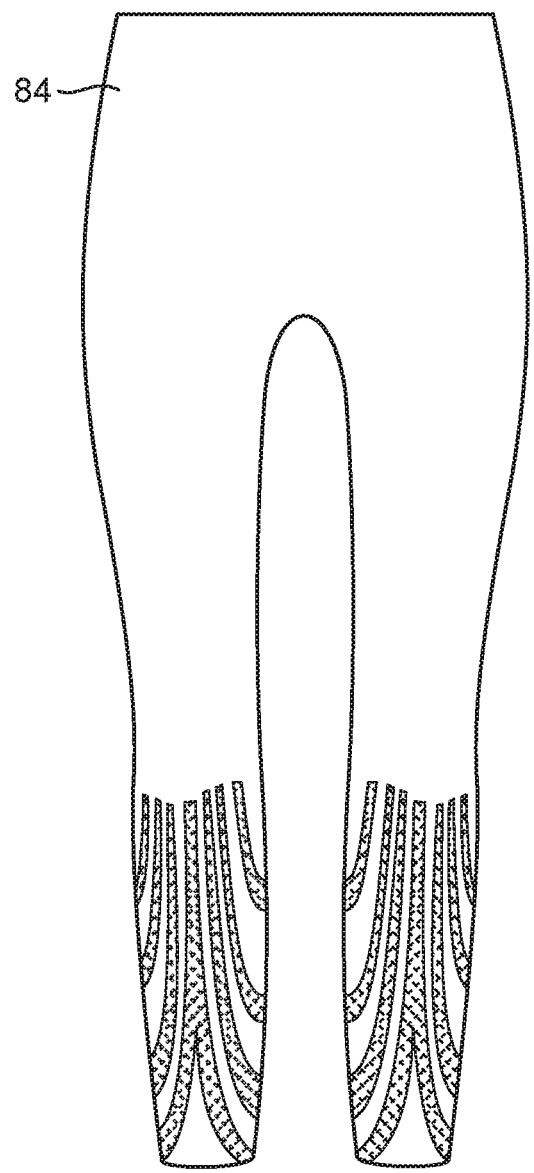
Figure 34B:
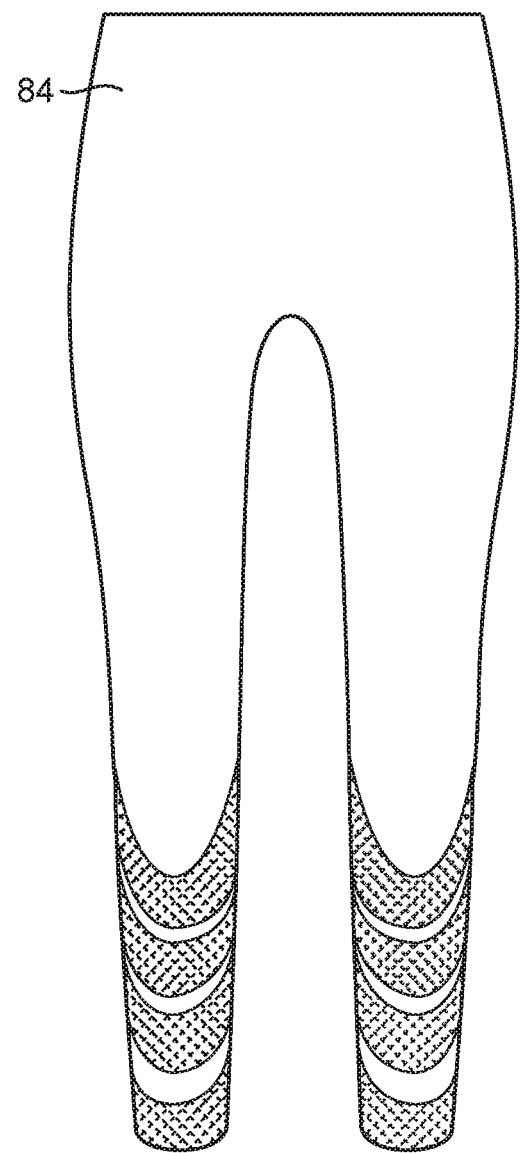
Figures 35A, 35B, 35C, 35D, 35E:
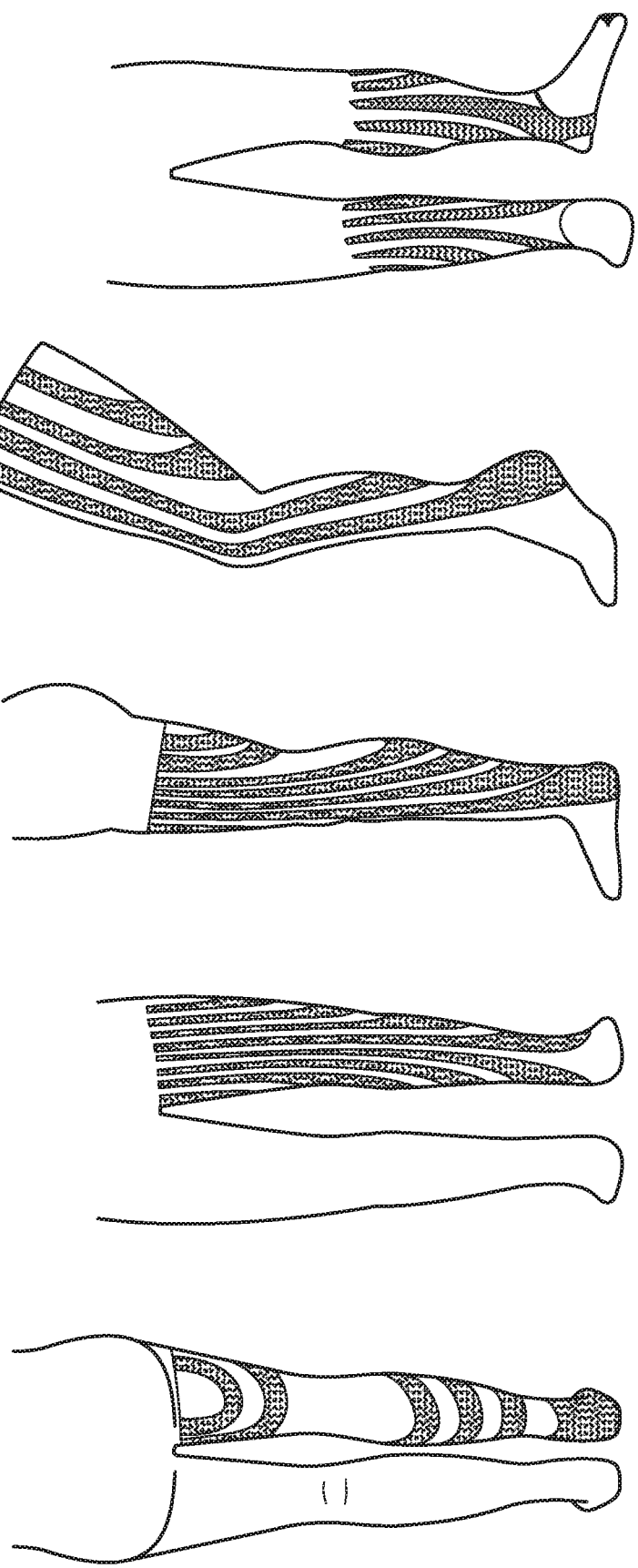

FIGS. 32A-34B illustrate some embodiments including the incorporation of various compression zones into various other items of clothing and/or clothing systems other than an over-the-calf sock 10 such as discussed previously. FIGS. 32A-32D shows front and back views of various exemplary short socks 80, and illustrates that the short socks 80 may be made of different lengths and/or numbers of compression zones as desired. FIGS. 33A-33B show front and back views of a pair of exercise pants incorporating one embodiment of a set of compression zones as discussed herein. Similarly, FIGS. 34A-34B show front and back views of a pair of leggings incorporating one embodiment of a set of compression zones as discussed herein.

With the extension of compression zones into items of clothing beyond socks, an opportunity is provided to provide compression zones to areas of the lower extremity (leg) beyond the region between the wearer's heel and the wearer's calf. For example, compression zones may be provided to any region of the lower extremity between the heel and the upper thigh, as is illustrated in FIGS. 35A-35E. FIGS. 35A-35E show various views of compression zones in accordance with some embodiments, including as many as six compression zones, along varying regions of a user's legs. Embodiments of the invention may be utilized to provide compression along essentially any region of the wearer's lower extremities, including extending between any two points along the lower extremities between the heel to the upper thigh, including any point selected from the heel, the lower calf, the mid-calf, the upper calf, the lower thigh, the mid-thigh, and the upper thigh.

Regardless of the item of clothing in which the various compression zones are incorporated, the compression zones and/or any material extending between the compression zones can be made of various structures, densities, materials and fabrics, and such structures, densities, materials, and fabrics can be selected to provide or achieve different secondary effects to the compression zones, the material extending between the compression zones, and/or the item of clothing. For example, the compression zones may be knitted with various structures of fabric to provide a micro massage effect. As another example, the compression zones may be knitted with different yarns to provide a cooling effect or a heating effect. Silicone strips may be added for better grip, etc.

Figure 36C:
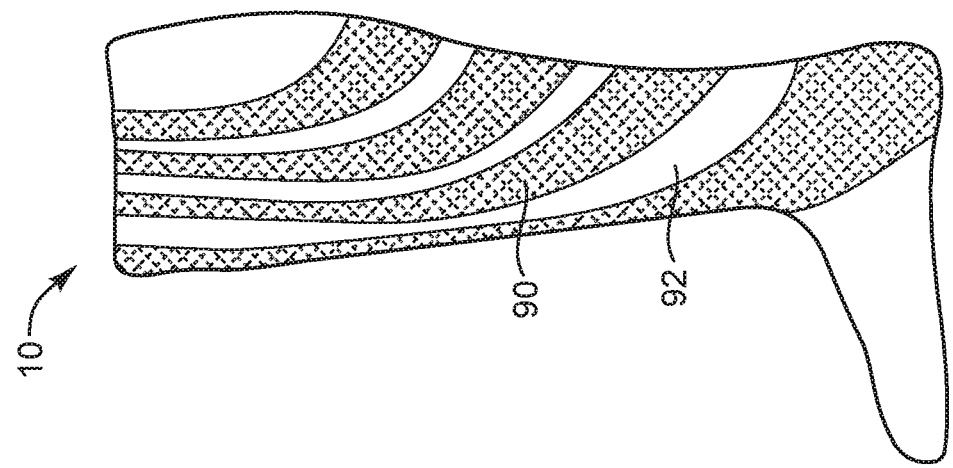
Figure 36B:
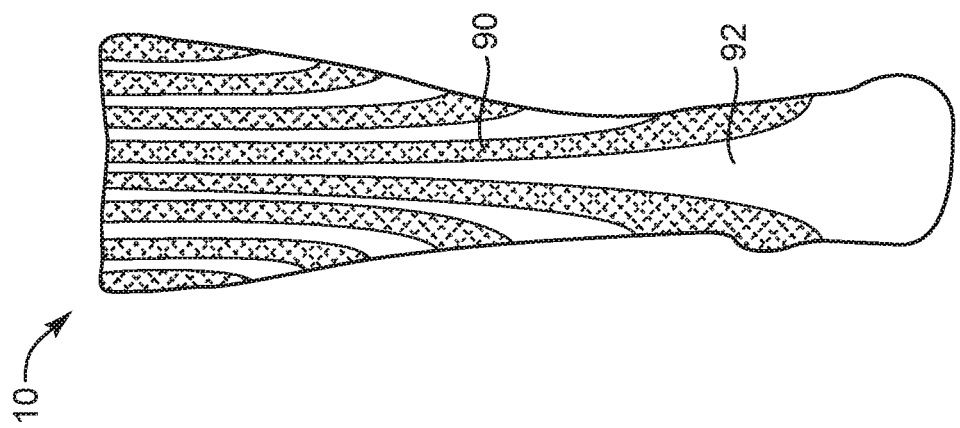
Figure 36A:
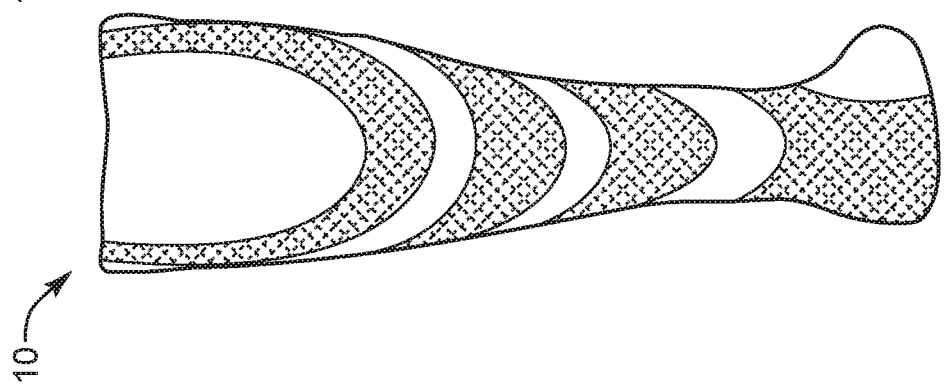
Figures 37A, 37B, 37C:
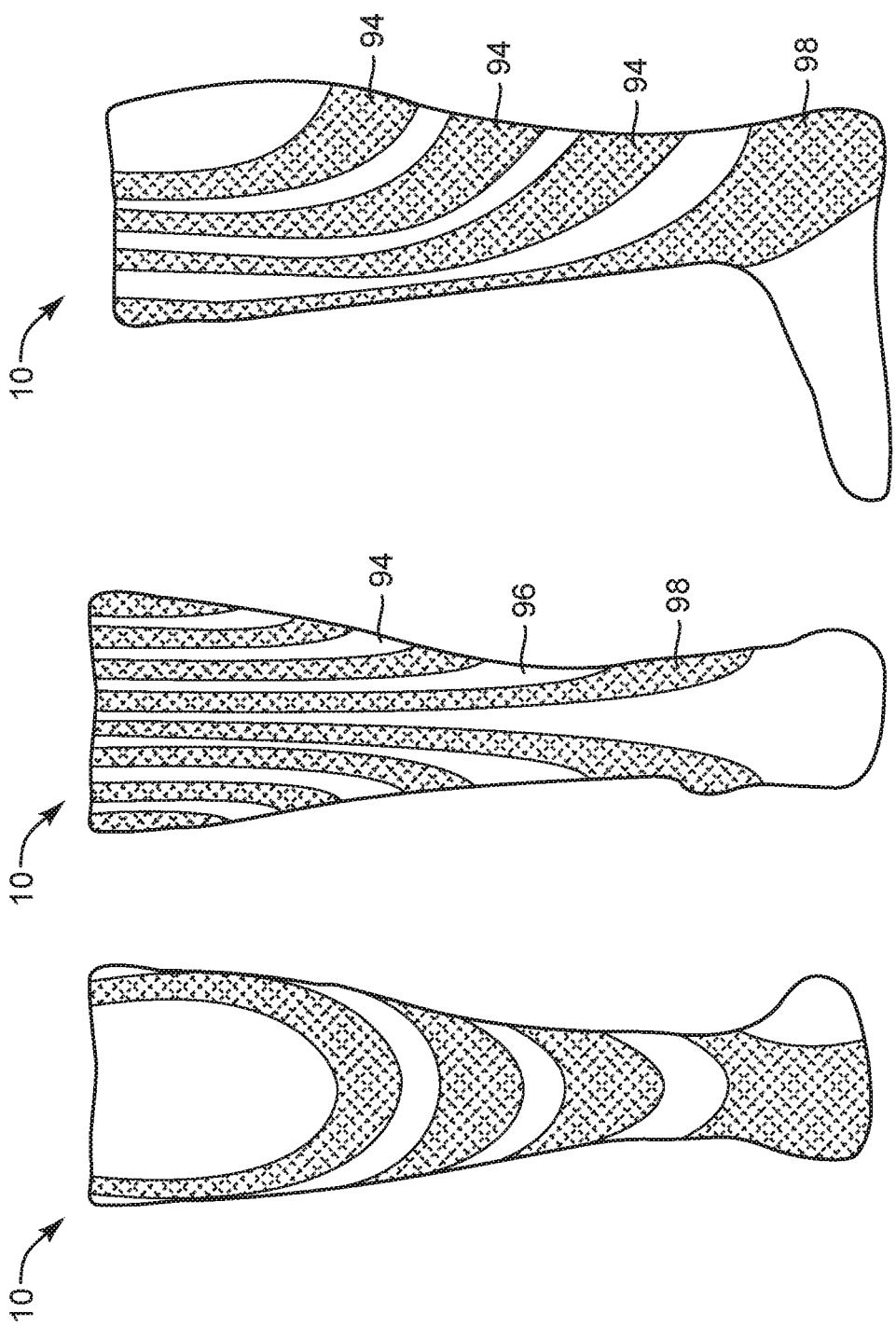

As another example, compression zones manufactured to have a smooth surface 90, as illustrated in FIGS. 36A-36C, may be more convenient for pulling up on the lengthwise areas 30 of the compression zones. The smooth surface might alternate with a textured surface 92 in between the compression zones to provide a massage effect, as also illustrated in FIGS. 36A-36C. As another example compression zones corresponding to the calf area might be formed of a cooling material 94, as shown in FIGS. 37A-37C, to provide a cooling effect, with a normal material 96 interspersed between the compression zones. In contrast, the compression zone corresponding to the foot or heel area might be formed of a heating material 98 to provide a heating effect.

As discussed, embodiments of the invention may provide active step-by-step or level-by-level active, longitudinally activated compression via the active consecutive manual pulling up of the various compression zones beginning with the most inferior compression zone and progressing to the most superior compression zone. In certain embodiments of the various clothing items in which the compression zones may be incorporated, improvement of venous return may be further enhanced by providing passive graduated compression.

Passive graduated compression may be provided, for example, by having the more-inferior compression zones have a higher compression amount than the compression amount of more-superior compression zones. Returning to the illustration of FIGS. 1A-1C, in a passive graduated compression embodiment, the compression level of the first compression zone 20 is greater than the compression level of the second compression zone 22. Similarly, the compression level of the second compression zone 22 is greater than the compression level of the third compression zone 24. The compression level of the third compression zone 24 is also greater than the compression level of the fourth compression zone 26.

In certain graduated compression embodiments, the compression amounts may be selected to comply with various established standards. As a first example, the item of clothing might comply with a standard (e.g., Quality Assurance RAL-GZ 387/1) that constitutes compression between about 18 and about 21 mmHg. In some such embodiments, the first compression zone 20 (e.g., corresponding to the calcaneal zone) has a compression strength of about 21 mmHg, the second compression zone 22 (e.g., corresponding to the lower part of the calf) has a compression strength of about 20 mmHg, the third compression zone 24 (e.g., corresponding to the middle part of the calf) has a compression strength of about 19 mmHg, and the fourth compression zone 26 (e.g., corresponding to the upper part of the calf) has a compression strength of about 18 mmHg.

As a second example, some embodiments of the item of clothing provide a compression between about 23 and about 32 mmHg. In such some such embodiments, the first compression zone 20 has a compression strength of about 32 mmHg, the second compression zone 22 has a compression strength of about 29 mmHg, the third compression zone 24 has a compression strength of about 26 mmHg, and the fourth compression zone 26 might has a compression strength of about 23 mmHg.

As a third example, the item of clothing provides compression between about 34 and about 46 mmHg (or in any other suitable range). In some such embodiments, the first compression zone 20 has a compression strength of about 46 mmHg, the second compression zone 22 has a compression strength of about 42 mmHg, the third compression zone 24 has a compression strength of about 38 mmHg, and the fourth compression zone 26 has a compression strength of about 34 mmHg.

As a fourth example, the item of clothing provides compression between about 49 and about 61 mmHg (or any other suitable range). In some such embodiments, the first compression zone 20 has a compression strength of about 61 mmHg, the second compression zone 22 has a compression strength of about 57 mmHg, the third compression zone 24 has a compression strength of about 53 mmHg, and the fourth compression zone 26 has a compression strength of about 49 mmHg.

Of course, other distributions of compression strengths are possible and are embraced as alternate embodiments of the invention, as the foregoing examples are intended in all respects as illustrative only. For example, the foregoing examples provide roughly equal distributions of changes in compression strength. Alternate embodiments might provide for greater or lesser decreases in compressive strength between more-inferior compression zones or alternatively between more-superior compression zones, as desired. In certain embodiments, the selected compression levels recited above or elsewise might be measured at the respective crosswise portions 32 of each compression zone.

In addition or alternatively to providing passive graduated compression as discussed above, embodiments of the invention also provide active compression zones having differing compressive strengths through two or more parts or levels, as may be illustrated with reference to FIGS. 38 and 39. The differing compressive strengths may be provided along all portions of the various compression zones, or may be provided more or less solely along the respective crosswise areas 32 such that the lengthwise areas 30 are not divided into portions of different compressive strengths, at least at their more-superior extents. The differing compressive strengths of the subparts of the compression zones may be provided with or without passive graduated compression.

Figure 38:
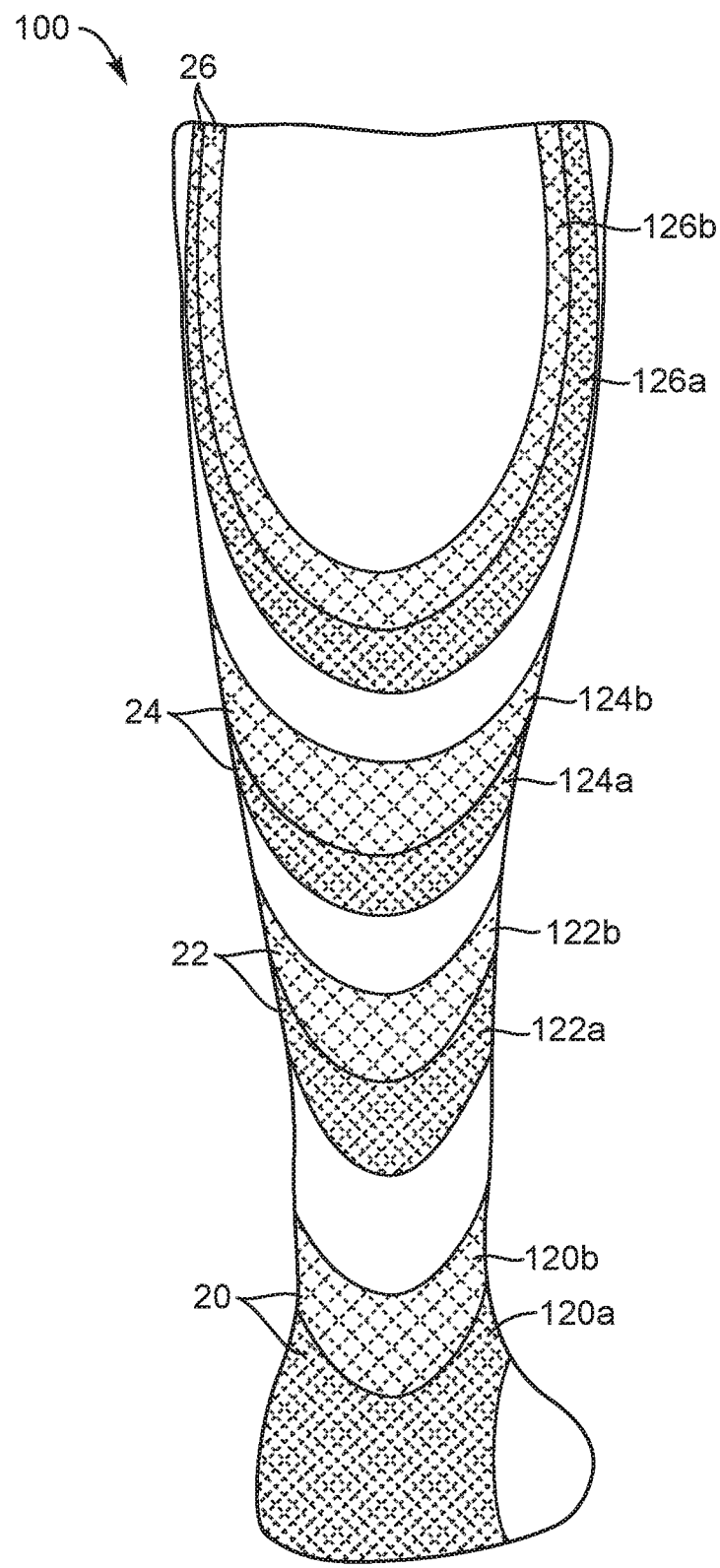
FIGS. 38-39 illustrate subdivided compression zones having different compressive strengths.

FIG. 38 illustrates a back view an exemplary sock 100 in which each of the various compression zones 20, 22, 24, and 26 discussed with respect to previously discussed embodiments are subdivided into a higher-compressive-strength inferior compression zone and a lower-compressive-strength superior compression zone. Thus in the sock 100 having four compression zones (other embodiments may have more or fewer compression zones as discussed previously), there are four inferior compression zones each paired with and immediately adjacent to one of four superior compression zones.

In a first type of such an embodiment, each of the inferior compression zones has a similar compressive strength, and each of the superior compression zones has a similar compressive strength. In other words, such an example of the sock 100 does not have the passive graduated compression.

In a second type of such an embodiment, the more-inferior of the inferior compression zones generally have a greater compressive strength (at least in the crosswise portions 32 thereof) than the more-superior of the inferior compression zones. Similarly, the more inferior of the superior compression zones generally have a greater compressive strength (at least in the crosswise portions 32 thereof) than the more-superior of the superior compression zones. In other words, such an example of the sock 100 has the passive graduated compression discussed previously.

Turning specifically to FIG. 38, the first compression zone 20 in this example is divided into two parts, a first inferior compression zone 120a and a first superior compression zone 120b. Similarly, the second compression zone 22 is divided into two parts, a second inferior compression zone 122a and a second superior compression zone 122b. The third compression zone 24 is also divided into two parts, a third inferior compression zone 124a and a third superior compression zone 124b. Also, the fourth compression zone 26 is divided into two parts, a fourth inferior compression zone 126a and a fourth superior compression zone 126b. As is most visible in FIG. 38 with respect to the fourth inferior compression zone 126a and the fourth superior compression zone 12b, the separation between the various inferior and superior compression zones may be maintained throughout the crosswise areas 32 and the entirety of the lengthwise areas 30 in this example.

Figure 39:
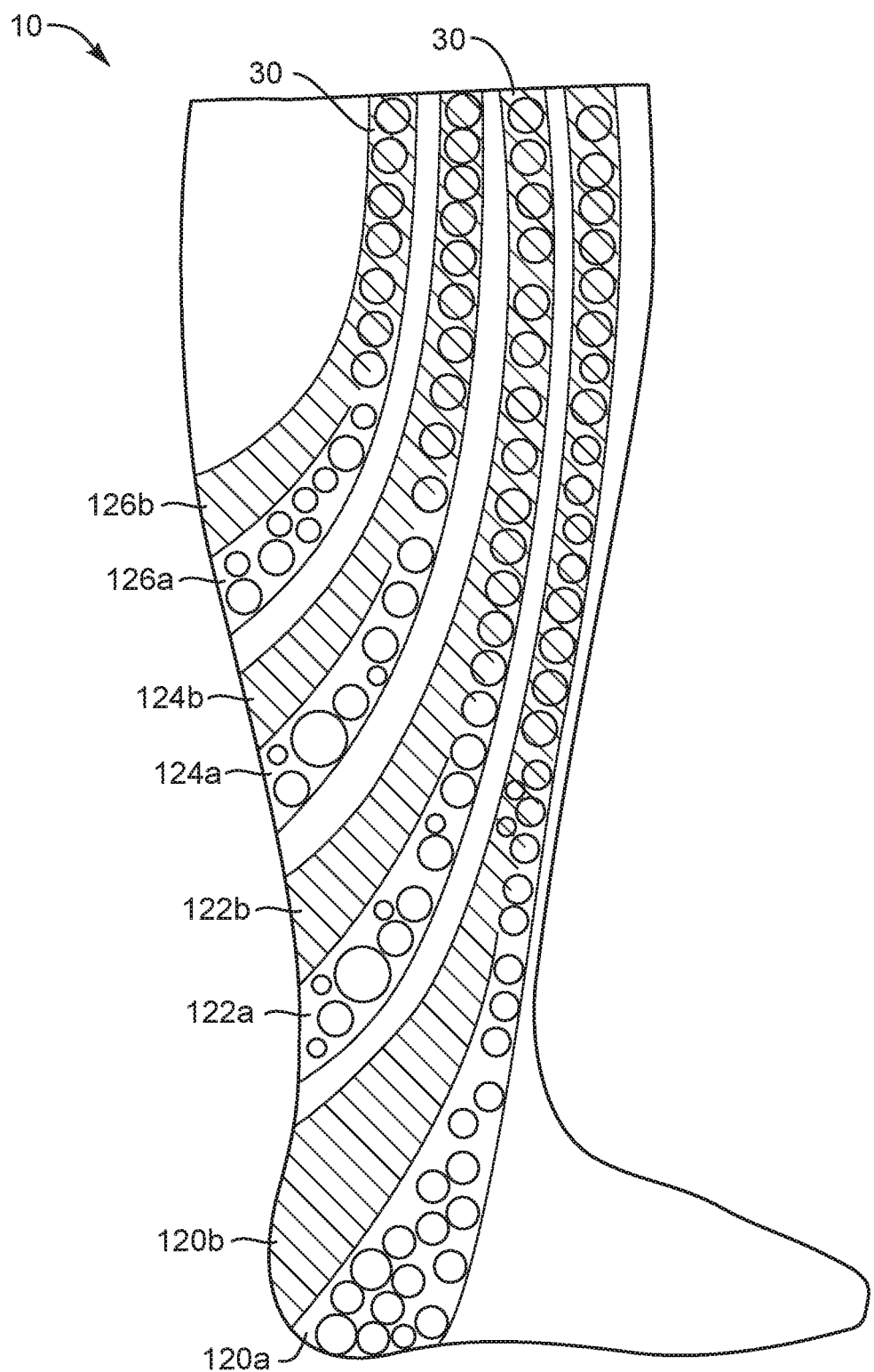

FIG. 39 illustrates a side view of an alternate embodiment in which the separation between the various inferior and superior compression zones is not maintained throughout the entirety of the lengthwise areas 30. Instead, the separation between the various inferior and superior compression zones is most prominent at the respective crosswise areas 32, and the pairs of inferior and superior compression zones merge or fuse at some point along the lengthwise areas to form a unitary, single-compressive-strength member.

While FIGS. 38 and 39 illustrate examples in which each of the compression zones 20, 22, 24, and 26 separate into pairs of zones of different strengths (the respective inferior and superior compression zones), this example should not be deemed limiting on the number of layers or strengths that could be incorporated into each compression zone. Other exemplary embodiments have three or four layers of compression strength in each compression zone, and still other exemplary embodiments include a smooth gradient of compressive strength across the superior-to-inferior breadth of each compression zone.

As mentioned, the sock 100 may also incorporate passive graduated compression. By way of illustration only, one specific example will be provided with reference to FIG. 38, but it should be understood that embodiments of the invention are not limited to the specific strengths discussed herein. In the illustrated example, the strength of the various compression zones is to vary between approximately 17 mmHg to approximately 20.5 mmHg (and/or any other suitable range). The material making up the portions of the sock 100 between and around the various compression zones might have a compressive strength of about 15 mmHg.

In accordance with some embodiments, the first inferior compressive zone 120*a* has a compressive strength of about 20.5 mmHg while the first superior compressive zone 120*b* has a compressive strength of about 20 mmHg. In some such embodiments, the second inferior compressive zone 122*a* has a compressive strength of about 19.5 mmHg while the second superior compressive zone 122*b* has a compressive strength of about 19 mmHg. In some such embodiments, the third inferior compressive zone 124*a* has a compressive strength of about 18.5 mmHg while the third superior compressive zone 124*b* has a compressive strength of about 18 mmHg. In some such embodiments, the fourth inferior compressive zone 126*a* has a compressive strength of about 17.5 mmHg while the fourth superior compressive zone 126*b* has a compressive strength of about 17 mmHg. The specific strength of compression for each zone or material can vary depending on the desired degree of compression and the desired effect for the sock 100 or other article of clothing.

As various embodiments of the invention are intended to allow for manual application of force in a generally superior direction to the lengthwise areas 30 (or at least the superior ends thereof) to provide for active stage-by-stage or level-by-level compression and evacuation of blood, certain embodiments of the socks or other items of clothing may be provided with one or more gripping elements to facilitate grasping of the individual lengthwise areas 30 of the various compression zones. The gripping elements may take any form that facilitates in grasping, securing, and pulling up on the lengthwise area 30 of each compression zone in a more-convenient fashion. In at least some embodiments, at least one gripping element is provided for each lengthwise area terminating proximal the top (superior) end of the item of clothing. In some embodiments the gripping element is generally provided at or near the superior end of the item of clothing.

Figure 42C:
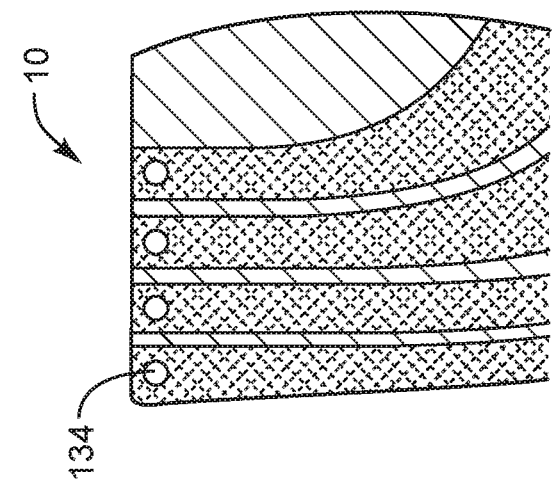
Figure 42B:
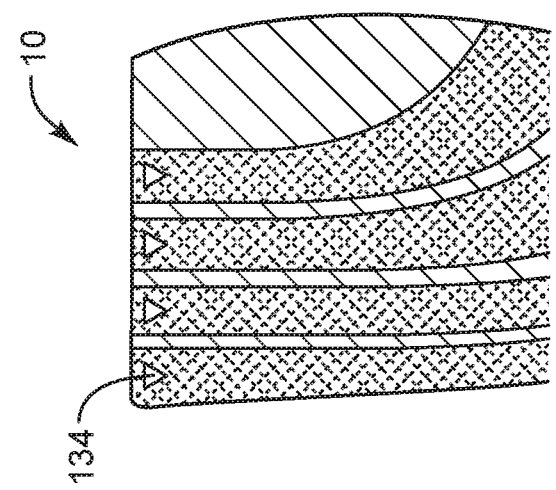
Figure 42A:
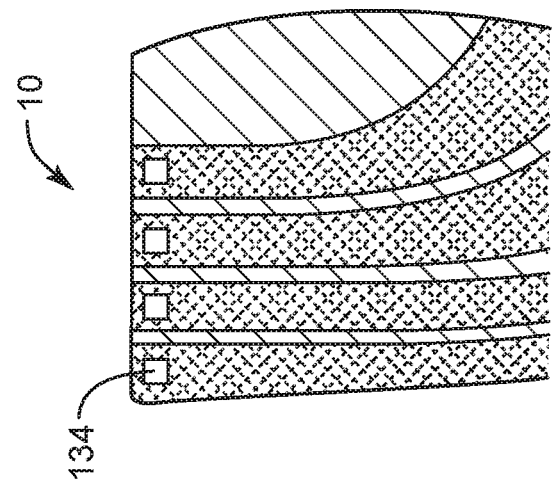
Figure 43:
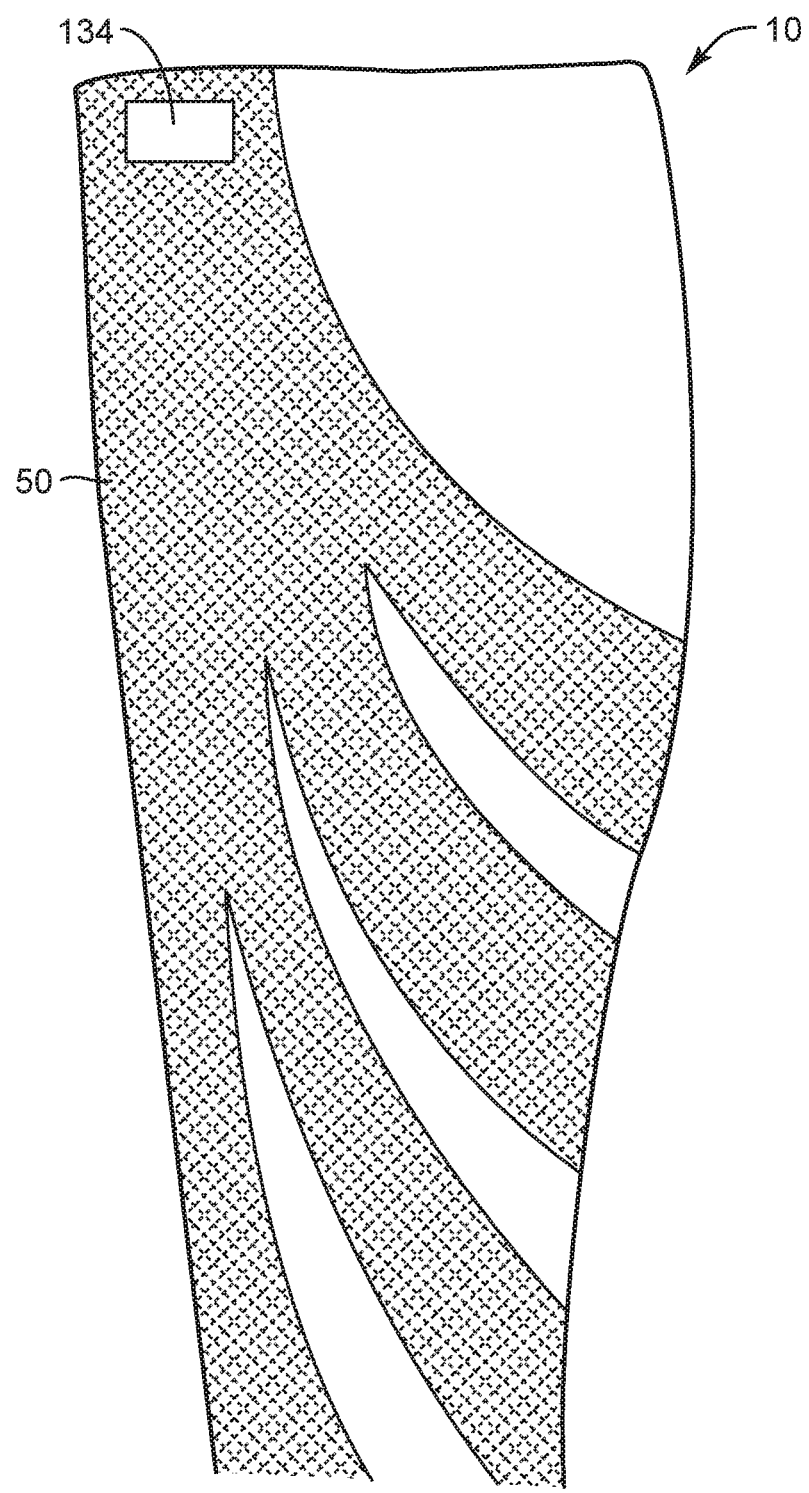

FIGS. 40A-43 illustrate various embodiments of gripping elements. Gripping elements other than those specifically illustrated in FIGS. 40A-43 may also be provided without departing from the spirit of the embodiments of the invention described herein. FIGS. 40A-40C illustrates various views of a sock having flaps, tassels, grips, and/or tabs 130 serving as the gripping elements. The flaps or tabs 130 extend beyond a portion of the sock generally defining a top edge of the sock, whereby it is relatively easy for the wearer or someone else to grasp each of the tabs 130 to apply the sequential superiorly directed force in accordance with the methods discussed herein. The flaps or tabs 130 shown in FIGS. 40A-40C represent a semi-circular extension of the lengthwise area 30 of the respective compression zones.

Where the flaps or tabs 130 of FIGS. 40A-40C are contiguous or solid in that there is no hole passing there through that could receive a finger, alternative gripping elements provide a hole for a finger to pass through to facilitate pulling up on the compression zones. FIGS. 41A-41C illustrate one such example where the gripping elements are upwardly extending loops 132. The loops 132 extend upwardly beyond a generally defined upper edge of the sock, whereby it is relatively easy for the wearer or for someone else to grasp the loops 132 to apply the sequential superiorly directed force in accordance with the methods discussed herein. FIGS. 42A-42C illustrate another example where the gripping element includes holes adapted to receive a human finger, in this case with holes 134 passing through each lengthwise area just below an upper edge of the sock. As is illustrated in FIGS. 42A-42C, the holes 134 may have any desired shape for functional or aesthetic purposes, such as square, round, oval, triangular, or any other desired shape. Another example of an element that could be used as a gripping element is a raised material disposed on the lengthwise areas 30, such as a heavily stitched line or arc that facilitates grasping and reduces slippage of the fingers after grasping the raised portion of the lengthwise area 30. FIG. 43 illustrates that where multiple lengthwise areas 30 converge to one of the unitary superior portions 50, a single one of the gripping elements such as the hole 134 may be provided as sufficient.

Figure 44A:
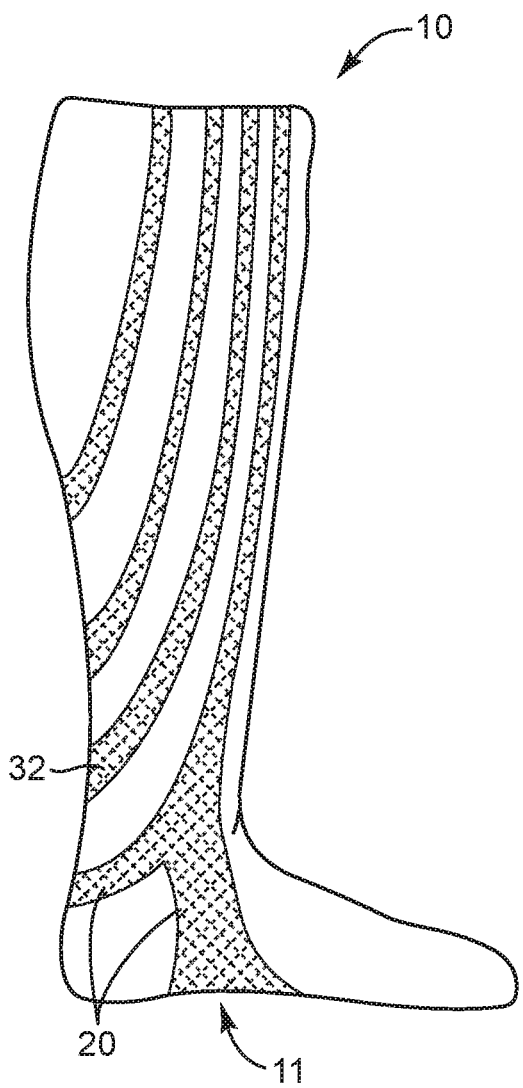
FIGS. 44A-44B illustrate some embodiments in which the functional sock comprises one or more arch support compression zones.
Figure 44B:
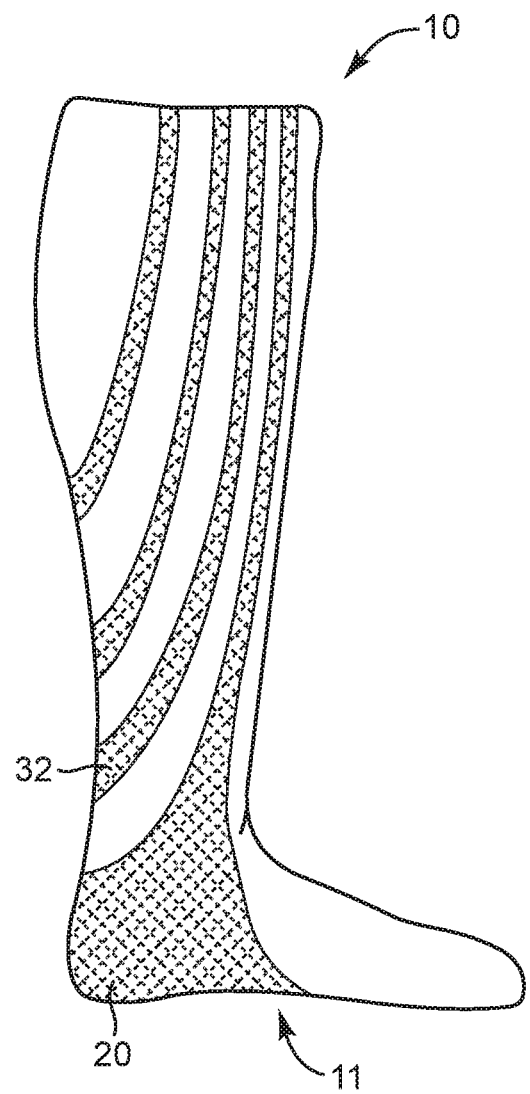

In addition to the foregoing, the described item of clothing (e.g., sock 10) can comprise any other suitable component or characteristic that allows it to function as intended. By way of non-limiting illustration, FIGS. 44A and 44B show some embodiments in which the sock comprises one or more compression zones that are configured to contact (and/or to apply pressure to) an arch portion 11 of a wearer's foot. Additionally, while such compression zones can be independent or combined with any other compression zones, FIGS. 44A and 44B show some embodiments in which such compression zones are formed or otherwise combined with the first compression zone 20.

Additionally, (as described herein) in some other examples: the superior portion of one or more of the targeted compression zones joins with its inferior portion to form an inverted T shape; the superior portions of two or more of the plurality of targeted compression zones join into a single unified superior portion proximate a most superior portion of the respective superior portions; adjacent zones of the plurality of targeted compression zones are joined by sections of a less-compressive material; and/or the plurality of targeted compression zones extend in a direction generally anterior-superior to posterior-inferior.

Embodiments of the invention such as those discussed herein may have many uses. The active step-by-step and level-by-level compression to provide improved venous return of the venous blood in the lower extremity back to the heart can be used in a variety of situations. For example, embodiments of the invention may be used during travel and flights, during extended sitting periods, during extended standing periods, during pregnancy, in case of puffiness of the legs, during fitness and exercise, during long walking periods, or for any other medical reason.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A system for providing targeted compression to a portion of a lower extremity to provide improved venous return characteristics, the system comprising:
   one or more articles of clothing comprising:
      a superior edge of the one or more articles of clothing defining a superior opening adapted to receive entry of a portion of a lower extremity into the one or more articles of clothing therethrough;
      a first compression zone comprising a first proximal end and a second proximal end that are each disposed at anterior locations of the superior edge of the one or more articles of clothing,
wherein the one or more articles of clothing are configured such that when a user wears the one or more articles of clothing on the lower extremity with the anterior locations of the one or more articles of clothing covering an anterior portion of the lower extremity, the first compression zone extends from the first proximal end, distally away from a core of the user, posteriorly across a posterior portion of the one or more articles of clothing, and proximally toward the core of the user and anteriorly to the second proximal end such that a distal-most portion of the first compression zone is disposed at the posterior portion of the one or more articles of clothing;
a second compression zone comprising a third proximal end and a fourth proximal end that are each disposed at anterior locations of the superior edge, wherein the second compression zone extends distally and posteriorly from the third proximal end, across the posterior portion of the one or more articles of clothing, and proximally and anteriorly to the fourth proximal end, wherein a distal-most portion of the second compression zone is located more distally on the one or more articles of clothing than is a distal-most portion of the first compression zone.

2. The system as recited in claim 1, wherein the one or more articles of clothing further comprise a third compression zone comprising a fifth proximal end and a sixth proximal end that are each disposed at anterior locations of the superior edge, wherein the third compression zone extends distally and posteriorly from the fifth proximal end, across the posterior portion of the one or more articles of clothing, and proximally and anteriorly to the sixth proximal end, wherein a distal-most portion of the third compression zone is located more distally on the one or more articles of clothing than is the distal-most portion of the second compression zone.

3. The system as recited in claim 1, wherein the system comprises a plurality of articles of clothing adapted to be at least partially layered over one another, wherein a first article of clothing comprises the first compression zone, and wherein a second article of clothing comprises the second compression zone.

4. The system as recited in claim 1, wherein the third proximal and fourth proximal ends of the second compression zone are disposed more anteriorly on the one or more articles of clothing than are the first and second ends of the first compression zone.

5. The system as recited in claim 1, wherein the one or more articles of clothing comprise a sock, and wherein the first proximal end and the second proximal end of the first compression zone are disposed at a cuff region of the sock.

6. The system as recited in claim 3, wherein the third and fourth proximal ends of the second compression zone are disposed at between zero and forty-five degrees around either side from a most-anterior portion of the one or more articles of clothing.

7. The system as recited in claim 1, wherein the first compression zone and the second compression zone respectively comprise a first compressive material and a second compressive material, and wherein a material that is less compressive than the first and the second compressive materials is disposed between at least a portion of the first compression zone and a portion of the second compression zone.

8. The system as recited in claim 1, wherein:
the one or more articles of clothing comprise a single sock,
the first compression zone and the second compression zone are disposed on the single sock, and
a vertical compression zone couples the first compression zone to the second compression zone at the posterior portion of the one or more articles of clothing.

9. The system as recited in claim 1, wherein the first compression zone comprises an arch-shaped strip of material.

10. The system as recited in claim 9, wherein the arch-shaped strip of material comprises at least one of a U-shape, a trapeze shape, a W-shape, a polygonal arch shape, an oval arch shape, a V-shaped arch, and an arch shape comprising arch segments of different shapes.

11. The system as recited in claim 1, wherein at least one of the first proximal end and the second proximal end of the first compression zone comprises a first gripping element adapted to facilitate manual application of a first proximally directed force to the first compression zone, and wherein at least one of the third proximal end and the fourth proximal end of the second compression zone comprises a second gripping element that is adapted to facilitate manual application of a second proximally directed force to the second compression zone.

12. The system as recited in claim 11, wherein the first gripping element comprises an element selected from the group consisting of:
a hole passing through a portion of the first compression zone;
a thickened portion of the first compression zone;
a tab coupled to the first compression zone; and
a flap coupled to the first compression zone.

13. The system as recited in claim 1, wherein the system further provides passive graduated compression, whereby:
the second compression zone is configured to provide more passive compression than the first compression zone.

14. The system as recited in claim 1, wherein the first compression zone comprises a plurality of compression levels along a posterior portion of the first compression zone, wherein a more distal portion of the posterior portion of the first compression zone is configured to provide more compression than a proximal portion of the posterior portion of the first compression zone.

15. The system as recited in claim 14, wherein the plurality of compression levels comprises a non-stepwise gradient of compression levels.

16. The system as recited in claim 1, wherein the first compression zone comprises a material adapted to provide additional functionality selected from the group consisting of:
a cooling effect;
a heating effect;
a lower-friction effect; and
a massaging effect.

17. The system as recited in claim 1, wherein the first and second proximal ends of the first compression zone and the third and fourth proximal ends of the second compression zone couple to a unitary superior element disposed at an anterior location of the one or more articles of clothing.

18. A method for providing targeted compression to portions of a lower extremity using the system as recited in claim 1, the method comprising:
placing at least one of the one or more articles of clothing as recited in claim 1 on the lower extremity;

applying a first proximally directed force to the second compression zone to provide increased compression in a first distal portion of the lower extremity; and subsequently applying a second proximally directed force to the first targeted compression zone to provide increased compression in a stepwise fashion to a second distal portion of the lower extremity, wherein the second distal portion of the lower extremity is proximal to the first distal portion of the lower extremity.

19. A system for providing targeted compression to a lower leg, the system comprising:

a first tubular item having:
- a first end having a superior edge defining a superior opening adapted to receive entry of a portion of a lower leg into the first tubular item therethrough;
- a second end that is configured to be disposed farther from a core of a user than is the first end when the first tubular item is worn by the user;
- an anterior portion that is configured to be worn over an anterior portion of the lower leg;
- a posterior portion that is configured to be worn over a posterior portion of the lower leg;
- a first compression strap; and
- a second compression strap, wherein the first compression strap has a third end and a fourth end that are each disposed at the anterior portion and terminating at the superior edge of the first end of the first tubular item, and wherein the first compression strap extends from its third end, towards the second end of the first tubular item, across the posterior portion of the first tubular item, and then back towards the first end of the first tubular item to the fourth end of the first compression strap, and wherein the second compression strap has a fifth end and a sixth end that are each disposed at the anterior portion and terminating at the superior edge of the first end of the first tubular item, and wherein the second compression strap extends from its fifth end, towards the second end of the first tubular item, across the posterior portion of the tubular item, and then back towards the first end of the tubular item to the sixth end of the second compression strap.

20. The system of claim 19, wherein the third and fourth ends of the first compression strap are disposed more anteriorly on the first tubular item than are the fifth and sixth ends of the second compression strap.

\* \* \* \* \*